US008618328B2

(12) United States Patent
Plenio et al.

(10) Patent No.: US 8,618,328 B2
(45) Date of Patent: Dec. 31, 2013

(54) CYCLOPENTADIENYL, INDENYL OR FLUORENYL SUBSTITUTED PHOSPHINE COMPOUNDS AND THEIR USE IN CATALYTIC REACTIONS

(75) Inventors: Herbert Plenio, Bensheim (DE); Christoph Fleckenstein, Freigericht-Somborn (DE); Renat Kadyrov, Frankfurt (DE); Juan Almena, Hanau (DE); Axel Monsees, Frankfurt (DE); Thomas Riermeier, Ober-Ramstadt (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/437,415

(22) Filed: Apr. 2, 2012

(65) Prior Publication Data

US 2012/0245348 A1    Sep. 27, 2012

Related U.S. Application Data

(62) Division of application No. 12/375,869, filed as application No. PCT/EP2007/058417 on Aug. 14, 2007, now abandoned.

(30) Foreign Application Priority Data

Aug. 31, 2006   (EP) ..................................... 06119870

(51) Int. Cl.
  *C07F 9/02*  (2006.01)
(52) U.S. Cl.
  USPC ............................................................ 568/8
(58) Field of Classification Search
  None
  See application file for complete search history.

(56) References Cited

U.S. PATENT DOCUMENTS

| | | |
|---|---|---|
| 6,657,027 B2 | 12/2003 | Ostoja-Starzewski |
| 6,849,754 B2 | 2/2005 | Deschler |
| 6,995,280 B2 | 2/2006 | Korth |
| 7,019,160 B2 | 3/2006 | Korth |
| 7,323,582 B2 | 1/2008 | Deschler |
| 7,332,619 B2 | 2/2008 | Korth |
| 7,339,067 B2 | 3/2008 | Korth |
| 7,371,881 B2 | 5/2008 | Frings |
| 7,518,009 B2 | 4/2009 | Korth |
| 7,772,349 B2 | 8/2010 | Friedel |
| 7,799,938 B2 | 9/2010 | Korth |
| 8,013,178 B2 | 9/2011 | Klockmann |
| 2004/0059073 A1 | 3/2004 | Starzewski |

FOREIGN PATENT DOCUMENTS

| | | |
|---|---|---|
| DE | 10114345 A1 | 9/2002 |
| EP | 1097158 | 5/2001 |
| WO | 9801487 | 1/1998 |
| WO | 0002887 | 1/2000 |
| WO | 0210178 | 2/2002 |

OTHER PUBLICATIONS

Fleckenstein et al. (Chem. Eur. J., 2007, 13, 2701).*
Toneri et al. (Macromolecules, 2001, 34, 1518).*
Stradiotto et al.: "A Catalytically active, charge-neutral Rh(I) zwitterion . . . " J. Am. Chem. Soc., vol. 125, 2003, pp. 5618-5619.
Krut'do D P et al.: "Regioselectivity of Reactions of Vinyl and Isopropenylcyclopentadien . . . " Russian Chemical Bulletin, Kluwer Academic Publishers, vol. 54, No. 2, Feb. 1, 2005—pp. 390-399.
Couret et al.: "Addition des germyl-et silylphosphines aux aldehydes et cetones . . . " J. Organomet. Chem, vol. 91, 1975 pp. 11-30, p. 28, line 38, p. 29, line 16.
Juztzi et al.: "Synthese and Dynamisches Verhalten . . . " Chem Ber. vol. 117, 1984, pp. 222-233.
Jutzi et al.: "Synthese and Struktur von . . . ", Chem Ber, vol. 110, 1977, pp. 1269-1276, compound 11—p. 1276, line 18-line 25.
Kazul'Kin et al.: "Zirconium Complexes Involving 2-Phosphorus-Substituted Indeny . . . ", Organometallics, vol. 24, 2005, pp. 3024-3035.
Dombrowski et al.: "Synthesis of a 4-methylene-6-phosphabicyclo . . . ", Chem Comm, 1996, pp. 1705-1706.

(Continued)

*Primary Examiner* — Johann R Richter
*Assistant Examiner* — Jennifer C Sawyer
(74) *Attorney, Agent, or Firm* — Smith, Gambrell & Russell, LLP

(57) ABSTRACT

Disclosed herein are phosphine compounds represented by the general formula (4):

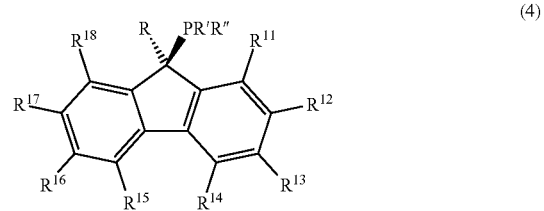

and corresponding phosphonium salts represented by the general formula (4a):

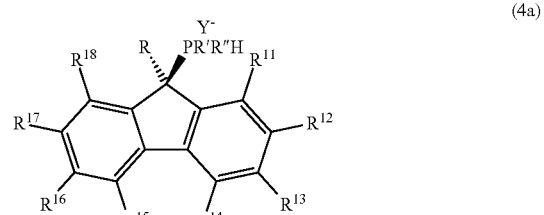

Also disclosed are processes for the preparation of these phosphines and phosphonium salts as well as their use as ligands in catalytic reactions.

13 Claims, No Drawings

(56) References Cited

OTHER PUBLICATIONS

Wile, Bradely M. et al.: "Neutral and Cationic Platinum II Complexes Supported by a P, N-Functionalized . . . ", Organometallics, 25(4), 1028-1035 Coden.

L. Baiget et al.: "New Halo Compounds of Si, P, As, and Sb Bearing a Bulky Substituted . . . ", Phosphorous Sulfur, Silicon, 178: 1949-1961, 2003.

Kolodyazhnyi, O.I., "Reaction of Phosphorylated Phosphorus (III) Carbon Acidswith . . . " 1980, 1885-6.

Kolodyazhnyi, O.I., "Reaction of Sterically Hindered Phosphines with Carbontetrahalides", 1981, 2466-80.

Blake C. Hamann and John F. Hartwig, "Sterically Hindered Chelating Alkyl Phosphines Provide Large . . . ", J. Am. Chem Soc: 1998, 120, 7369-7370.

Adam F. Littke and Gregory C. Fu.

Peter Jutzi and Hartmt Saleske, "Synthesis and Dynamic Behavior of Pentamethylcyclopentadienylphosphanes", Chem. Ber. 117, 222-233 (1984).

Peter Jutzi, et al., Journal of Organometallic Chemistry, 118 (1976) C8-C10.

Motoi Kawatsura and John F. Hartwig, "Simple, Highly Active Palladium Catalysts for Ketone and Malonate . . . ", J. Am Chem. Soc (1999), 121, 1473-1478.

David W. Old, et al. "A Highly Active Catalyst for Palladium-Catalyzed Cross-Coupling Reactions . . . ", J. Am Chem Soc. (1998), 120, 9722-9723.

Stephen Barlow, et al. "Synthesis and Structures of Organometallic Derivatives of . . . ", J. Chem. Soc., Dalton Trans., (1997) pp. 3887-3878.

Rainer Streubel et al. "Synthesis of the First Pentacarbonyltungsten (0) Complexes with . . . ", Z. Amorg Allg. Cem (2004), 630, 1215-1219.

Starzewski, O. et al. (1999) "Donor/Acceptor Metallocenes: A New Structure Principle in Catalytic Design" Angewandte Chemie, 38:2439-2443. Printed citation provided from European Office Action.

Holand, S. et al. (1988) "Introducing New Phosphorus Substituents in Terminal Phosphinidene Complexes. An Illustration with [(ethoxycarbonyl) phosphinidene]-, (tert-butoxyphosphinidene)-, and (fluorenylphosphinidene) pentacarbonyltungsten complexes" Organometallics 7:1796-1801. Printed citation provided from European Office Action.

European Office Action received in 07788423.7, mailed Jan. 4, 2012.

\* cited by examiner

CYCLOPENTADIENYL, INDENYL OR FLUORENYL SUBSTITUTED PHOSPHINE COMPOUNDS AND THEIR USE IN CATALYTIC REACTIONS

CROSS REFERENCE TO RELATED APPLICATION DATA

This application is a divisional of U.S. patent application Ser. No. 12/375,869, filed 30 Jan. 2009 now abandoned, which is a 371 National Phase entry of PCT/EP2007/058417, filed 14 Aug. 2007, and claims priority to EP 06119870.1, filed 31 Aug. 2006, all of which are relied on and incorporated herein by reference.

INTRODUCTION AND BACKGROUND

The present invention relates to new phosphine ligands, to their preparation and to their use in catalytic reactions, especially organic coupling reactions employing aryl, heteroaryl or vinyl halides and pseudohalides as educts.

Organic coupling reactions are an important tool to form carbon-carbon and carbon-heteroatom bonds. The popularity of coupling reactions is partly due to their tolerance against the presence of functional groups. This characteristic allows the use of coupling reactions in the synthesis of very complex molecules and thus, coupling reactions are widely used in the chemical and pharmaceutical industry, e.g. for the preparation of agricultural chemicals, pharmaceuticals, and dyestuffs, and, if vinyl compounds are coupled, to prepare monomers for polymerization reactions.

Suitable reactants for the coupling reactions are aryl, heteroaryl and vinyl halides, triflates, and other pseudohalides. The coupling reactions are catalyzed by transition metal compounds, typically palladium or nickel compounds. Palladium catalysts are generally advantageous in terms of the breadth of applicability of coupling substrates and in some cases the catalyst activity, while nickel catalysts have advantages in the area of the conversion of chloroaromatics and vinyl chlorides and the price of the metal. Palladium and nickel catalysts used to activate the aryl, heteroaryl and vinyl halides/pseudohalides are palladium(II) and/or nickel(II) as well as palladium (0) and/or nickel(0) complexes, although it is known that palladium(0)/nickel(0) compounds are the actual reaction catalysts. In particular, according to literature sources, coordinatively unsaturated 14-electron and 16-electron palladium (0)/nickel(0) complexes stabilized with donor ligands such as phosphines are formulated as active species.

Amongst the above-mentioned educts for coupling reactions, the iodides are the most reactive ones. It is even possible to use palladium or nickel compounds that are not stabilized by a phosphine or a similar donor ligand when iodides are employed as educts in coupling reactions. However, aryl and vinyl iodides are very expensive starting compounds and moreover produce stoichiometric amounts of iodine salt waste. The remaining educts, i.e. the aryl, heteroaryl and vinyl bromides, chlorides, triflates and other pseudohalides require the use of stabilizing and activating ligands in order to become effective in catalytic production.

Until some years ago, exclusively iodides, bromides, and triflates were used as educts in most of the catalyzed coupling reactions described. Obviously, organic chlorides were not employed as reactants although they should be the most appropriate reactants due to their low costs and great variety. Unfortunately, the chlorides proved to be generally not reactive under the reaction conditions used for coupling of iodides, bromides, and triflates. The low reactivity of chlorides is usually attributed to the strength of the C—Cl bond. Accordingly, the oxidative addition of the chlorides to the metal center of the catalyst (e.g. $Pd^0$) occurs only reluctantly; however, this is the crucial first step in metal-catalyzed coupling reactions. Only within the last years, some progress was made concerning the development of new palladium-based catalysts that are effective in the coupling of chlorides.

The catalyst systems described for coupling reactions often have satisfactory catalytic turnover numbers (TONs) only with uneconomic starting materials such as iodides and activated bromides. Otherwise, in the case of deactivated bromides and especially in the case of chlorides, it is generally necessary to add large amounts of catalyst, usually more than 1 mol %, to achieve industrially useful yields (>90%). In addition, because of the complexity of the reaction mixtures, simple catalyst recycling is not possible, so the recycling of the catalyst also incurs high costs, which are normally an obstacle to realization on the industrial scale. Furthermore, particularly in the preparation of active substances or active substance precursors, it is undesirable to work with large amounts of catalyst because of the catalyst residues left behind in the product. More recent active catalyst systems are based on cyclopalladized phosphines (W. A. Herrmann, C. Brossmer, K. Öfele, C.-P. Reisinger, T. Priermeier, M. Beller, H. Fischer, Angew. Chem. 1995, 107, 1989; Angew. Chem. Int. Ed. Engl. 1995, 34, 1844) or mixtures of bulky arylphosphines (J. P. Wolfe, S. L. Buchwald, Angew. Chem. 1999, 111, 2570; Angew. Chem. Int. Ed. Engl. 1999, 38, 2413) or tri-tert.-butylphosphine (A. F. Littke, G. C. Fu, Angew. Chem. 1998, 110, 3586; Angew. Chem. Int. Ed. Engl. 1998, 37, 3387) with palladium salts or palladium complexes.

However, even with these catalysts, cost-effective chlorides cannot generally be activated satisfactorily from the industrial point of view. Therefore, to achieve high yields, it is necessary to use comparatively large and hence very expensive amounts of catalyst. Unfortunately, the current noble metal prices are still high, so there is clearly a need for improving catalyst productivity. Therefore, despite all the catalyst developments in recent years, only a few industrially applicable reactions have so far been disclosed for the coupling of chlorides.

The properties of transition metal catalyst complexes are recognized to be influenced by both the characteristics of the metal and those of the ligands associated with the metal atom. For example, structural features of the ligands can influence reaction rate, regioselectivity, and stereoselectivity.

Trialkylphosphines with bulky substituents are highly useful ligands for transition metal complexes, especially palladium complexes, as catalysts in various types of coupling reactions. The main reasons for the favorable catalytic properties of trialkylphosphine palladium complexes are the electron-richness and the steric bulk of trialkylphosphine ligands, which favor the formation of low coordinate and highly active Pd complexes also observed with N-heterocyclic carbenes as Pd ligands in cross-coupling reactions. Prominent examples of phosphines are $PCy_3$, $P(tert.-Bu)_3$ and ligands of the $Ad_2PR$ type (Ad=1-adamantyl, R=$CH_2Ph$, n-Bu) (Beller et al., Angew. Chem. Int. Ed. 2000, 4153, and WO-A-02/10178). Especially $PtBu_3$ is highly useful; its utility for a wide range of different coupling reactions has been established.

A significant disadvantage of Pd catalysts based on bulky trialkylphosphines, primarily $(tert.-Bu)_3P$, is the lack of flexibility in the design of ligands and catalysts. Detailed structural and electronic modifications ("catalyst fine tuning") are difficult to realize and this could be the reason why in cross-coupling chemistry this class of ligands was "leader of the pack" only about five years ago. Today numerous other specialized and more powerful catalysts, often based on phosphines and N-heterocyclic carbenes as ligands for Pd are available. Examples of phosphines having a highly variable ligand backbone are the Buchwald type biphenyl based phosphines (S. Buchwald et al., J. Am. Chem. Soc. 1998, 9722, EP-A-1 097 158) and N-phenyl-2-pyrrole based phosphines (M. Beller et al., Chem. Comm. 2004, 38). These types of ligands exhibit a good performance in numerous coupling reactions because they allow a fine tuning of their steric and electronic properties.

One object of the present invention is to provide new phosphines preferably exhibiting crucial properties for good ligands such as electron-richness and efficient-donation as perfectly met in trialkylphosphines, but lacking the disadvantages of the trialkylphosphines, i.e. they should have a variable ligand backbone. The new phosphines should be useful as ligands in new catalyst systems that possess greater substrate flexibility, e.g., the ability to utilize cost-effective organic chlorides as educts, and are suitable for a great variety of industrial scale reactions, preferably coupling reactions, that produce the desired products in high yield, with high catalytic productivity, and/or with high purity.

SUMMARY OF INVENTION

The object is achieved by a phosphine compound represented by the general formula (1)

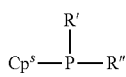

(1)

or a corresponding phosphonium salt represented by the general formula (1a)

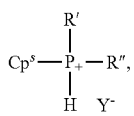

(1a)

wherein

R' and R" independently are selected from alkyl, cycloalkyl and 2-furyl radicals, or R' and R" are joined together to form with the phosphorous atom a carbon-phosphorous monocycle comprising at least 3 carbon atoms or a carbon-phosphorous bicycle; the alkyl radicals, cycloalkyl radicals, and carbon-phosphorous monocycle being unsubstituted or substituted by at least one radical selected from the group of alkyl, cycloalkyl, aryl, alkoxy, and aryloxy radicals;

$Cp^s$ is a partially substituted or completely substituted cyclopentadien-1-yl group, including substitutions resulting in a fused ring system, and wherein a substitution at the 1-position of the cyclopentadien-1-yl group is mandatory when the cyclopentadien-1-yl group is not part of a fused ring system or is part of an indenyl group; and $Y^-$ represents an anion;
excluding a phosphine compound represented by formula (A)

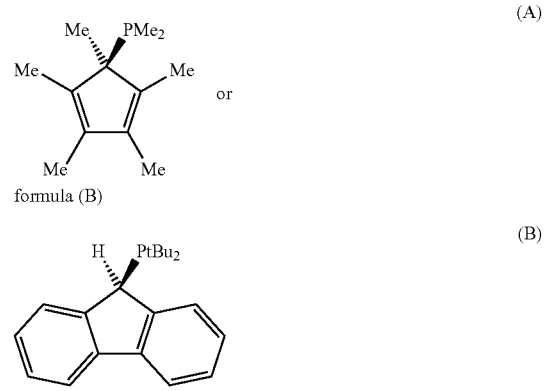

and their corresponding phosphonium salts (Aa) and (Ba), wherein Me represents a methyl radical and tBu represents a t-butyl radical.

The present invention is also directed to a coordination compound comprising (i) a phosphine compound represented by the general formula (1) wherein R', R", and $Cp^s$ are defined as above, and (ii) a transition metal selected from groups 8, 9, 10 and 11 of the Periodic Table of the Elements. A further aspect of the present invention is the use of said coordination compound as a catalyst or a part of a catalyst system for the preparation of an organic compound.

Yet another aspect of the present invention is the use of a phosphine compound represented by the general formula (1) or a corresponding phosphonium salt represented by the general formula (1a) wherein R', R", $Cp^s$ and $Y^-$ are defined as above, in combination with a transition metal compound as a catalyst or a part of a catalyst system for the preparation of an organic compound wherein the transition metal is selected from groups 8, 9, 10, and 11 of the Periodic Table of the Elements.

The present invention is further directed to process for the preparation of said phosphine compound comprising the steps of: deprotonating a compound according to the formula $HCp^s$ by the use of a strong base and reacting the resulting anion with a phosphinous halide according to the formula R'R"PX to form the phosphine compound R'R"P$Cp^s$, wherein $Cp^s$, R' and R" are defined as above and X is Cl or Br. The present invention is also directed to an alternative process for the preparation of said phosphine compound comprising the steps of: deprotonating a compound according to the formula $HCp^s$ by the use of a strong base and reacting the resulting anion with a phosphonous dihalide according to the formula $R'PX_2$ to form the phosphinous halide according to the formula $Cp^sR'PX$, and alkylating the phosphinous halide with an appropriate organometallic alkylation agent to introduce the R" group and to form the phosphine compound R'R"P$Cp^s$, wherein $Cp^s$, R' and R" are defined as above and X is Cl or Br.

Within the present application the following abbreviations are used to represent a specific radical:
Me=methyl; Et=ethyl; iPr=isopropyl; nPr=n-propyl; tBu=tert.-butyl; nBu=n-butyl; Cy=cyclohexyl; Neo-Pn=neopentyl; Ad=adamantly; Bn=benzyl; Ph=phenyl, and Cp=cyclopentadien-1-yl.

DETAILED DESCRIPTION OF INVENTION

The $Cp^s$ group is a monocycle (i.e. a cyclopentadienyl group) or a multicycle (e.g. an indenyl group when one benzene ring is fused to the cyclopentadienyl group or a fluorenyl group when two benzene rings are fused to the cyclopentadienyl group).

Phosphine compounds comprising an unsubstituted cyclopentadienyl group or an unsubstituted indenyl group as one substituent as well as transition metal complexes comprising those phosphines as ligands are known from the literature (Kolodyazhnyi, O. I., "Reaction of phosphorylated phosphorus(III) carbon acids with carbon tetrahalides" in Zhurnal Obshchei Khimii (1980), 50(8), 1885-6; Kolodyazhnyi, O. I., "Reaction of sterically hindered phosphines with carbon tetrahalides" in Zhurnal Obshchei Khimii (1981), 51(11), 2466-80; and Fallis, Kathleen A.; Anderson, Gordon K.; Rath, Nigam P., "Synthesis of two isomers of (diphenylphosphino) indene and their platinum(II) complexes" in Organometallics (1992), 11(2), 885-8). However, the use of these transition metal complexes in catalytic reactions has not been described. Only, metallocene type coordination compounds, e.g. a ferrocene type coordination compound, wherein one or two cyclopentadienyl dialkyl or diarylphosphine ligands are bound to the metal atom, e.g. Fe, via their delocalized π-electrons in an $\eta^5$-bonding mode and their use as part of a catalyst system are disclosed in the prior art (Dubbaka, Srinivas Reddy; Vogel, Pierre, "Palladium-Catalyzed Suzuki-Miyaura Cross-Couplings of Sulfonyl Chlorides and Boronic Acids" in Organic Letters (2004), 6(1), 95-98; Kawatsura, Motoi; Hartwig, John F., "Simple, Highly Active Palladium Catalysts for Ketone and Malonate Arylation Dissecting the Importance of Chelation and Steric Hindrance" in Journal of the American Chemical Society (1999), 121(7), 1473-1478; Hamann, Blake C.; Hartwig, John F., "Sterically Hindered Chelating Alkyl Phosphines Provide Large Rate Accelerations in Palladium-Catalyzed Amination of Aryl Iodides, Bromides, and Chlorides, and the First Amination of Aryl Tosylates" in Journal of the American Chemical Society (1998), 120(29), 7369-7370). In those metallocene type compounds the cyclopentadienyl dialkyl or diaryl phosphine ligands formally are aromatic anions; hence, the electronic structure of those compounds is completely different to that in a coordination compound according to the present invention.

A phosphine compound according to formula (A) above comprising a pentamethylcyclopentadienyl group as one substituent is also known from the prior art (Jutzi, Peter; Saleske, Hartmut; Nadler, Doris, "The synthesis of thermally stable pentamethylcyclopentadienyl-substituted phosphorus compounds" in Journal of Organometallic Chemistry (1976), 118 (1), C8-C10; and Jutzi, Peter; Saleske, Hartmut, "Synthesis and dynamic behavior of pentamethylcyclopentadienylphosphines" in Chemische Berichte (1984), 117(1), 222-33). However, neither its use as phosphine ligand in transition metal complexes nor its use in catalytic reactions has been mentioned.

Another group of known compounds comprising a pentamethylcyclopentadienyl-substituted phosphorous atom are P-pentamethylcyclopentadienyl-substituted 1H-phosphirenes that are employed as ligands in tungsten complexes (Streubel, Rainer; Bodea, Maren; Schiemann, Udo; Wismach, Cathleen; Jones, Peter G.; Monsees, Axel, "Synthesis of the first pentacarbonyltungsten(0) complexes with P-pentamethylcyclopentadienyl-substituted 1H-phosphirene ligands: Crystal structure of [cyclic][{Me$_5$C$_5$PCH:CPh}W(CO)$_5$]", Zeitschrift für Anorganische and Allgemeine Chemie (2004), 630(8-9), 1215-1219). However, the use of these tungsten complexes in catalytic reactions has not been disclosed.

Only few phosphine compounds comprising a fluorenyl group as one substituent have been described in the literature. The publication by L. Baiget et al. in Phosphorous Sulfur 2003, 178, 1949 only refers to fluorenyl diarylphosphines. O. I. Kolodyazhnyi, J. Gen. Chem. USSR 1981, 51, 2125 discloses fluorenyl di-t.-butylphosphine according to formula (B), its preparation and its conversion to a P-ylid. Again, these references are silent about the use of these phosphine compounds as phosphine ligands in transition metal complexes or their use in catalytic reactions.

It was in fact surprising and it was the merit of the present inventors to have found out that the phosphine compounds according to the present invention can be used as ligands in transition metal complexes that may function as highly efficient catalysts.

In formulae (1)

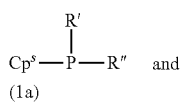

R' and R" may independently be selected from alkyl, preferably $C_1$ to $C_{18}$ alkyl, more preferably $C_1$ to $C_5$ alkyl, most preferably $C_3$ to $C_5$ alkyl; cycloalkyl, preferably $C_5$ to $C_{12}$ cycloalkyl, more preferably $C_5$ to $C_{10}$ cycloalkyl, most preferably $C_6$ to $C_8$ cycloalkyl; and 2-furyl. The alkyl radicals may be branched or unbranched. Preferred alkyl radicals are selected from isopropyl, n-butyl, t-butyl, and neopentyl. Most preferred is isopropyl. The cycloalkyl radicals may be monocyclic or multicyclic, such as adamantyl and norbornyl. Preferred cycloalkyl radicals are cyclohexyl and adamantyl. Preferably, R' and R" represent the same radicals, more preferably both are isopropyl or cyclohexyl. All the foregoing radicals represented by R' and R" are unsubstituted or may be substituted by at least one radical selected from the group of alkyl, cycloalkyl, aryl, alkoxy, and aryloxy radicals. Preferably, the radicals represented by R' and R" are unsubstituted.

In an alternative embodiment R' and R" are joined together to form with the phosphorous atom a carbon-phosphorous monocycle comprising at least 3 carbon atoms or a carbon-phosphorous bicycle. The carbon-phosphorous monocycle is typically unsubstituted, but may also be substituted by at least one radical selected from the group of alkyl, cycloalkyl, aryl, alkoxy, and aryloxy radicals. Preferably, R' and R" are joined together to form a [3.3.1]- or [4.2.1]-phobyl radical with the phosphorous atom as depicted below.

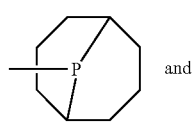

[3.3.1]-phobyl

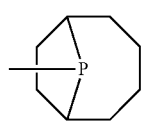

[4.2.1]-phobyl

In the first class of phosphine compounds according to the present invention Cp$^s$ in formulae (1) and (1a) is a monocycle, i.e. a partially substituted or completely substituted cyclopentadien-1-yl group. Preferably, the phosphine compound and its corresponding phosphonium salt according to this embodiment are represented by formulae (2) and (2a):

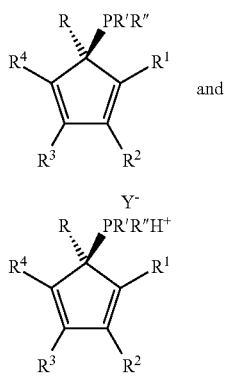

wherein
R is selected from the group consisting of aliphatic, heteroaliphatic, aromatic, alicyclic, heterocyclic radicals, heteroatom-containing radicals comprising an aromatic, alicyclic, or heterocyclic radical and an additional heteroatom linking the aromatic, alicyclic, or heterocyclic radical atom with the carbon atom of the cyclopentadienyl group, all the foregoing radicals being unsubstituted or substituted by further carbon and/or heteroatoms; and organosilyl radicals;
$R^1$, $R^2$, $R^3$, and $R^4$ independently are selected from the group consisting of hydrogen; aliphatic, heteroaliphatic, aromatic, alicyclic, heterocyclic radicals, heteroatom-containing radicals comprising an aromatic, alicyclic, or heterocyclic radical and an additional heteroatom linking the aromatic, alicyclic, or heterocyclic radical atom with the carbon atom of the cyclopentadienyl group, all the foregoing radicals being unsubstituted or substituted by further carbon and/or heteroatoms; halogens; and heteroatom-containing groups.

Within the context of the present invention, aliphatic radicals include alkyl, alkenyl, and alkynyl radicals; the radicals may be branched or unbranched. Heteroaliphatic radicals include alkyl, alkenyl, and alkynyl radicals additionally comprising at least one heteroatom, e.g. oxygen or sulfur, within their backbone or as linking atom; the radicals may be branched or unbranched. Alicyclic radicals include cycloalkyl, cycloalkenyl, and cycloalkynyl radicals; the term "alicyclic" also encompasses multicyclic systems. Aromatic radicals include monocyclic and multicyclic systems. Heterocyclic radicals include alicyclic radicals containing at least one heteroatom within the ring structure and aromatic radicals containing at least one heteroatom within the ring structure. "Unsubstituted" means substituted by only hydrogen atoms. "Substituted by further carbon atoms" means that at least one further carbon atom is bonded to the radical. Said carbon atom may be part of a hydrocarbyl group, e.g. aliphatic radicals may be substituted by aromatic radicals forming aralkyl radicals, and vice versa aromatic radicals may be substituted by aliphatic radicals forming alkylaryl radicals. Said carbon atom may also be part of a group comprising heteroatom(s), e.g. —CN, a carboxylic acid group, including the salt forms, or a carboxylic acid ester group. "Substituted by heteroatoms" means that at least one heteroatom is bonded to the radical. The heteroatom may be a single atom, such as a halogen atom, or may be bonded to further atoms thus forming a small group (e.g. —OH) or larger group (e.g. —NO₂). A "heteroatom-containing group" is any group that comprises at least one heteroatom, including groups that impart functionality and/or water-solubility to the molecule. Examples of heteroatom-containing groups are —SO₃H, —OSO₂Ph, —CN, —PO₃H₂, —OP(O)Ph₂, —NO₂, organosilyl, e.g. —SiMe₃ and SiPhMe₂.

With respect to formulae (2) and (2a) R is preferably selected from the group consisting of alkyl, cycloalkyl, aryl, aralkyl, alkenyl, alkynyl, alkoxy, and alkylsilyl radicals that are unsubstituted or substituted by further carbon and/or heteroatoms. More preferably, R is selected from the group consisting of methyl, ethyl, n-propyl, isopropyl, n-octadecyl, benzyl, and phenyl radicals that are unsubstituted or substituted, preferably unsubstituted. Even more preferably, R is an unbranched alkyl radical or a benzyl radical. Most preferably R is a methyl or ethyl radical with methyl being even more preferred.

With respect to formulae (2) and (2a) $R^1$, $R^2$, $R^3$, and $R^4$ are preferably independently selected from the group consisting of hydrogen; alkyl, cycloalkyl, aryl, and alkoxy radicals that are unsubstituted or substituted; halogens; and heteroatom-containing groups. More preferably, $R^1$, $R^2$, $R^3$, and $R^4$ are independently selected from the group consisting of hydrogen, a methyl radical, a methoxy radical, and —SO—H. Even more preferably, $R^1$, $R^2$, $R^3$, and $R^4$ are independently selected from hydrogen and methyl radicals. Most preferably $R^1$, $R^2$, $R^3$, and $R^4$ are each a methyl radical.

Specific examples of cyclopentadienyl-substituted phosphine compounds according to formulae (2) and (2a) are compounds wherein the radicals R, R', R", $R^1$, $R^2$, $R^3$, and $R^4$ are defined as in the following table:

| No. | R | R' | R" | $R^1$ | $R^2$ | $R^3$ | $R^4$ |
|---|---|---|---|---|---|---|---|
| 14/14a | Me | Cy | Cy | Me | Me | Me | Me |
| 15/15a | Me | iPr | iPr | Me | Me | Me | Me |
| | Me | tBu | tBu | Me | Me | Me | Me |
| | Me | Ad | Ad | Me | Me | Me | Me |
| | Ph | Cy | Cy | Ph | Ph | Ph | Ph |
| | Ph | iPr | iPr | Ph | Ph | Ph | Ph |
| | Ph | tBu | tBu | Ph | Ph | Ph | Ph |
| | Ph | Ad | Ad | Ph | Ph | Ph | Ph |
| | Me | Neo-Pn | Neo-Pn | Me | Me | Me | Me |
| | Me | Cy | nBu | Me | Me | Me | Me |
| | Me | tBu | nBu | Me | Me | Me | Me |

For the ease of preparation, the most preferred cyclopentadienyl-substituted phosphine compounds according to formulae (2) and (2a) are those wherein R, $R^1$, $R^2$, $R^3$, and $R^4$ are each a methyl radical. Examples of these pentamethylcycopentadienyl-substituted phosphine compounds are:
(1,2,3,4,5-pentamethyl-2,4-cyclopentadien-1-yl)dicyclhexylphosphine (Cp*PCy₂) (14),

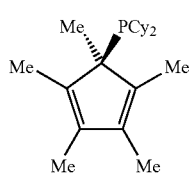

(1,2,3,4,5-pentamethyl-2,4-cyclopentadien-1-yl)dicy-
clhexylphosphine (Cp*PiPr$_2$) (15),

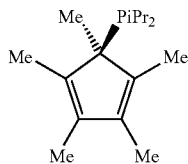

and their corresponding phosphonium salts Cp*PCy$_2$.H$^+$Y$^-$
(14a) and Cp*PiPr$_2$.H$^+$Y$^-$ (15a), wherein Cp* represents a
1,2,3,4,5-pentamethyl-2,4-cyclopentadien-1-yl radical.

In the second class of phosphine compounds according to
the present invention Cp$^s$ in formulae (1) and (1a) is a bicycle,
i.e. a partially substituted or completely substituted ind-2-en-
1-yl or ind-2-en-2-yl group, preferably a partially substituted
or completely substituted ind-2-en-1-yl group. More prefer-
ably, the phosphine compound and its corresponding phos-
phonium salt according to this embodiment are represented
by formulae (3) and (3a):

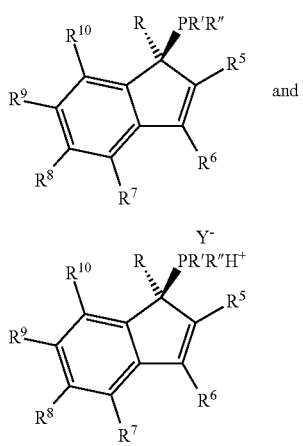

wherein
R is selected from the group consisting of aliphatic, het-
eroaliphatic, aromatic, alicyclic, heterocyclic radicals, and
aromatic, alicyclic, and heteroatom-containing radicals com-
prising an aromatic, alicyclic, or heterocyclic radical and an
additional heteroatom linking the aromatic, alicyclic, or het-
erocyclic radical atom with the carbon atom of the indenyl
group, all the foregoing radicals being unsubstituted or sub-
stituted by further carbon or heteroatoms; and organosilyl
radicals;
$R^5$, $R^6$, $R^7$, $R^8$, $R^9$, and $R^{10}$ independently are selected from
the group consisting of hydrogen; aliphatic, heteroaliphatic,
aromatic, alicyclic, heterocyclic radicals, heteroatom-con-
taining radicals comprising an aromatic, alicyclic, or hetero-
cyclic radical and an additional heteroatom linking the aro-
matic, alicyclic, or heterocyclic radical atom with the carbon
atom of the indenyl group, all the foregoing radicals being
unsubstituted or substituted by further carbon and/or heteroa-
toms; halogens; and heteroatom-containing groups.

With respect to formulae (3) and (3a) R is preferably
selected from the group consisting of alkyl, cycloalkyl, aryl,
aralkyl, alkenyl, alkynyl, alkoxy, and alkylsilyl radicals that
are unsubstituted or substituted by further carbon and/or het-
eroatoms. More preferably, R is selected from the group
consisting of methyl, ethyl, n-propyl, isopropyl, n-octadecyl,
benzyl, and phenyl radicals that are unsubstituted or substi-
tuted, preferably unsubstituted. Even more preferably, R is an
unbranched alkyl radical or a benzyl radical. Most preferably
R is a methyl or ethyl radical with methyl being even more
preferred.

With respect to formulae (3) and (3a) $R^5$, $R^6$, $R^7$, $R^8$, $R^9$,
and $R^{10}$ are preferably independently selected from the group
consisting of hydrogen, alkyl, cycloalkyl, aryl, and alkoxy
radicals that are unsubstituted or substituted; halogens, and
heteroatom-containing groups. More preferably, $R^5$, $R^6$, $R^7$,
$R^8$, $R^9$, and $R^{10}$ are independently selected from the group
consisting of hydrogen, a methyl radical, a methoxy radical,
and —SO$_3$H. Most preferably, $R^5$, $R^6$, $R^7$, $R^8$, $R^9$, and $R^{10}$ are
independently selected from the group consisting of hydro-
gen, a methyl radical, and a methoxy radical.

Specific examples of indenyl-substituted phosphine com-
pounds according to formulae (3) and (3a) are compounds
wherein the radicals R, R', R", $R^5$, $R^6$, $R^7$, $R^8$, $R^9$, and $R^{10}$ are
defined as in the following table:

| No. | R | R' | R" | $R^5$ | $R^6$ | $R^7$ | $R^8$ | $R^9$ | $R^{10}$ |
|---|---|---|---|---|---|---|---|---|---|
| 17/17a | Me | iPr | iPr | Me | Me | H | H | H | H |
|  | Me | iPr | iPr | Me | Me | Me | Me | Me | Me |
| 19/19a | Me | iPr | iPr | Me | Me | Me | H | H | Me |
| 21/21a | Me | iPr | iPr | Me | Me | OMe | H | H | OMe |
|  | Me | iPr | iPr | Me | Me | Me | SO$_3$H | H | Me |
|  | Me | iPr | iPr | Me | Me | iPr | H | H | iPr |
| 16/16a | Me | Cy | Cy | Me | Me | H | H | H | H |
|  | Me | Cy | Cy | Me | Me | Me | Me | Me | Me |
| 18/18a | Me | Cy | Cy | Me | Me | Me | H | H | Me |
| 20/20a | Me | Cy | Cy | Me | Me | OMe | H | H | OMe |
|  | Me | Cy | Cy | Me | Me | Me | SO$_3$H | H | Me |
|  | Me | Cy | Cy | Me | Me | iPr | H | H | iPr |
|  | Me | tBu | nBu | Me | Me | H | H | H | H |
|  | Me | tBu | nBu | Me | Me | Me | Me | Me | Me |
|  | Me | tBu | nBu | Me | Me | Me | H | H | Me |
|  | Me | tBu | nBu | Me | Me | OMe | H | H | OMe |
|  | Me | tBu | nBu | Me | Me | Me | SO$_3$H | H | Me |
|  | Me | tBu | nBu | Me | Me | i-Pr | H | H | iPr |
|  | Bn | iPr | iPr | Me | Me | H | H | H | H |
|  | Bn | iPr | iPr | Me | Me | Me | Me | Me | Me |
|  | Bn | iPr | iPr | Me | Me | Me | H | H | Me |
|  | Bn | iPr | iPr | Me | Me | OMe | H | H | OMe |
|  | Bn | iPr | iPr | Me | Me | Me | SO$_3$H | H | Me |
|  | Bn | iPr | iPr | Me | Me | iPr | H | H | iPr |
|  | Bn | Cy | Cy | Me | Me | H | H | H | H |
|  | Bn | Cy | Cy | Me | Me | Me | Me | Me | Me |
|  | Bn | Cy | Cy | Me | Me | Me | H | H | Me |
|  | Bn | Cy | Cy | Me | Me | OMe | H | H | OMe |
|  | Bn | Cy | Cy | Me | Me | Me | SO$_3$H | H | Me |
|  | Bn | Cy | Cy | Me | Me | iPr | H | H | iPr |
|  | Bn | tBu | nBu | Me | Me | H | H | H | H |
|  | Bn | tBu | nBu | Me | Me | Me | Me | Me | Me |
|  | Bn | tBu | nBu | Me | Me | Me | H | H | Me |
|  | Bn | tBu | nBu | Me | Me | OMe | H | H | OMe |
|  | Bn | tBu | nBu | Me | Me | Me | SO$_3$H | H | Me |
|  | Bn | tBu | nBu | Me | Me | iPr | H | H | iPr |

In a preferred embodiment R, $R^5$ and $R^6$ in formulae (3) or
(3a) are each a methyl radical, more preferably $R^7$, $R^8$, $R^9$ and
$R^{10}$ are independently selected from the group consisting of
hydrogen, a methyl radical and a methoxy radical. In this
embodiment it is advantageous that $R^7$, $R^8$, $R^9$ and $R^{10}$ are
either each hydrogen or $R^8$ and $R^9$ are each hydrogen and $R^7$
and $R^{10}$ are non-hydrogen radicals. Examples of this embodi-
ment of indenyl-substituted phosphine compounds are:

(1,2,3-trimethylind-2-en-1-yl)dicyclohexylphosphine (1,2,3-Me₃IndPCy₂) (16),

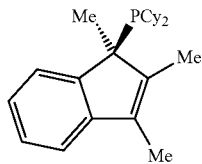

(1,2,3-trimethylind-2-en-1-yl)diisopropylphosphine (1,2,3-Me₃IndPiPr₂) (17),

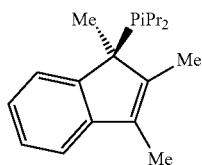

(1,2,3,4,7-pentamethylind-2-en-1-yl)dicyclohexylphosphine (1,2,3,4,7-Me₅IndPCy₂) (18),

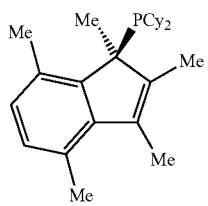

(1,2,3,4,7-pentamethylind-2-en-1-yl)diisopropylphosphine (1,2,3,4,7-Me₅IndPiPr₂) (19),

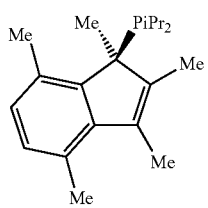

(4,7-dimethoxy-1,2,3-trimethylind-2-en-1-yl)dicyclohexylphosphine (4,7-(MeO)₂-1,2,3-Me₃IndPCy₂) (20),

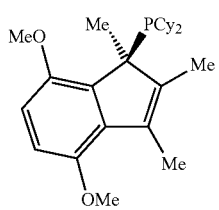

(4,7-dimethoxy-1,2,3-trimethylind-2-en-1-yl)diisopropylphosphine (4,7-(MeO)₂-1,2,3-Me₃IndPiPr₂) (21),

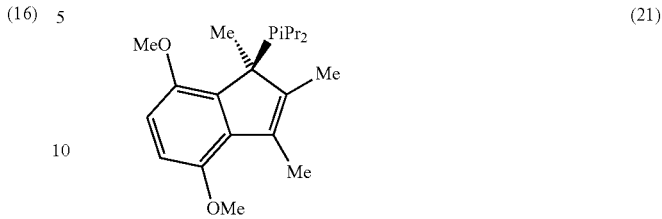

and their corresponding phosphonium salts
1,2,3-Me₃IndPCy₂.H⁺Y⁻ (16a),
1,2,3-Me₃IndPiPr₂.H⁺Y⁻ (17a),
1,2,3,4,7-Me₅IndPCy₂.H⁺Y⁻ (18a),
1,2,3,4,7-Me₅IndPiPr₂.H'Y (19a),
4,7-(MeO)₂-1,2,3-Me₃IndPCy₂.H⁺Y⁻ (20a), and
4,7-(MeO)₂-1,2,3-Me₃IndPiPr₂.H⁺Y⁻ (21a),
wherein Ind represents an ind-2-en-1-yl radical and Cy, iPr, and Me have the meanings defined above.

In the third class of phosphine compounds according to the present invention Cp$^s$ in formulae (1) and (1a) is a tricycle, i.e. an unsubstituted, partially substituted or completely substituted fluoren-9-yl group, including substitutions resulting in an enlarged fused ring system. Preferably, the phosphine compound and its corresponding phosphonium salt according to this embodiment are represented by formulae (4) and (4a):

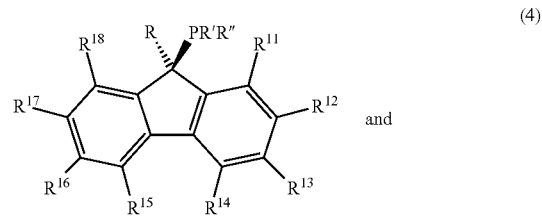

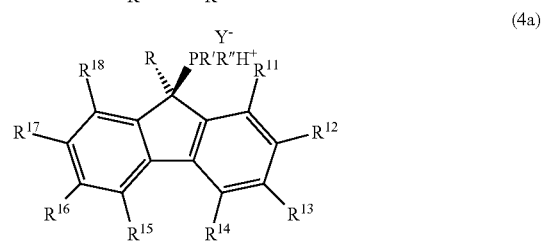

wherein
R is selected from the group consisting of hydrogen; aliphatic, heteroaliphatic, aromatic, alicyclic, heterocyclic radicals, and heteroatom-containing radicals comprising an aromatic, alicyclic, or heterocyclic radical and an additional heteroatom linking the aromatic, alicyclic, or heterocyclic radical atom with the carbon atom of the fluorenyl group, all the foregoing radicals being unsubstituted or substituted by further carbon and/or heteroatoms; and organosilyl radicals; $R^{11}$, $R^{12}$, $R^{13}$, $R^{14}$, $R^{15}$, $R^{16}$, $R^{17}$, and $R^{18}$ independently are selected from the group consisting of hydrogen; aliphatic, heteroaliphatic, aromatic, alicyclic, heterocyclic radicals, heteroatom-containing radicals comprising an aromatic, alicyclic, or heterocyclic radical and an additional heteroatom linking the aromatic, alicyclic, or heterocyclic radical atom with the carbon atom of the fluorenyl group, all the foregoing radicals being unsubstituted or substituted by further carbon and/or heteroatoms; halogens, and heteroatom-containing groups.

With respect to formulae (4) and (4a) R is preferably selected from the group consisting of alkyl, cycloalkyl, aryl, aralkyl, alkenyl, alkynyl, alkoxy, and alkylsilyl radicals that are unsubstituted or substituted by further carbon and/or heteroatoms. More preferably, R is selected from the group consisting of methyl, ethyl, n-propyl, isopropyl, n-octadecyl, benzyl, and phenyl radicals that are unsubstituted or substituted, preferably unsubstituted. Even more preferably, R is an unbranched alkyl radical or a benzyl radical. Most preferably R is a methyl or ethyl radical with ethyl being even more preferred.

With respect to formulae (4) and (4a) $R^{11}$, $R^{12}$, $R^{13}$, $R^{14}$, $R^{15}$, $R^{16}$, $R^{17}$, and $R^{18}$ are preferably independently selected from the group consisting of hydrogen, alkyl, cycloalkyl, aryl, and alkoxy radicals that are unsubstituted or substituted; halogens, and heteroatom-containing groups. More preferably, $R^{11}$, $R^{12}$, $R^{13}$, $R^{14}$, $R^{15}$, $R^{16}$, $R^{17}$, and $R^{18}$ are independently selected from the group consisting of hydrogen, a methyl radical, a methoxy radical, and —$SO_3H$. Even more preferably, $R^{11}$, $R^{12}$, $R^{13}$, $R^{14}$, $R^{15}$, $R^{16}$, $R^{17}$, and $R^{18}$ are independently selected from the group consisting of hydrogen, a methyl radical, and a methoxy radical. Still more preferably, $R^{14}$ and $R^{15}$ are each hydrogen and $R^{11}$, $R^{12}$, $R^{13}$, $R^{16}$, $R^{17}$, and $R^{18}$ are independently selected from hydrogen and methyl radicals. Still more preferably $R^{13}$, $R^{14}$, $R^{15}$, and $R^{16}$ are each hydrogen. Most preferably and $R^{11}$, $R^{12}$, $R^{13}$, $R^{14}$, $R^{15}$, $R^{16}$, $R^{17}$, $R^{18}$ are each hydrogen.

In another embodiment of the present invention $R^{12}$ and/or $R^{17}$ in formulae (4) or (4a) are a halogen or a heteroatom-containing group, preferably both are Br or one of them is —$SO_3H$, the remaining radicals of $R^{11}$, $R^{12}$, $R^{13}$, $R^{14}$, $R^{15}$, $R^{16}$, $R^{17}$, and $R^{18}$ are each hydrogen.

Specific examples of fluorenyl-substituted phosphine compounds according to formulae (4) and (4a) are compounds wherein the radicals R, R', R", $R^{11}$, $R^{12}$, $R^{13}$, $R^{14}$, $R^{15}$, $R^{16}$, $R^{17}$, and $R^{18}$ are defined as in the following table:

| No. | R | R' | R" | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|---|---|
| 8/8a | Me | Cy | Cy | H | H | H | H | H | H | H | H |
| 5/5a | Me | iPr | iPr | H | H | H | H | H | H | H | H |
| 9/9a | Et | Cy | Cy | H | H | H | H | H | H | H | H |
| 6/6a | Et | iPr | iPr | H | H | H | H | H | H | H | H |
| 22/22a | iPr | Cy | Cy | H | H | H | H | H | H | H | H |
| 23/23a | iPr | iPr | iPr | H | H | H | H | H | H | H | H |
| 24/24a | nPr | Cy | Cy | H | H | H | H | H | H | H | H |
| 25/25a | H | tBu | tBu | H | H | H | H | H | H | H | H |
| 11/11a | $C_{18}H_{37}$ | Cy | Cy | H | H | H | H | H | H | H | H |
| 7/7a | $C_{18}H_{37}$ | iPr | iPr | H | H | H | H | H | H | H | H |
| 10/10a | Bn | Cy | Cy | H | H | H | H | H | H | H | H |
| 26/26a | Bn | iPr | iPr | H | H | H | H | H | H | H | H |
| 27/27a | Bn | tBu | nBu | H | H | H | H | H | H | H | H |
| 28/28a | Et | tBu | nBu | H | H | H | H | H | H | H | H |
| 12/12a | Et | Cy | Cy | Me | H | H | H | H | H | H | H |
| 29/29a | Et | Cy | Cy | Me | H | Me | H | H | H | H | Me |
| 30/30a | Ph | iPr | iPr | H | H | H | H | H | H | H | H |
| 13/13a | Et | Cy | Cy | H | $SO_3H$ | H | H | H | H | H | H |
| 31/31a | Et | iPr | iPr | H | Br | H | H | H | H | Br | H |
| | Me | iPr | iPr | Me | H | H | H | H | H | H | Me |
| | Me | iPr | iPr | iPr | H | H | H | H | H | H | iPr |
| | Me | iPr | iPr | OMe | H | H | H | H | H | H | OMe |
| | Me | iPr | iPr | H | Br | H | H | H | H | Br | H |
| | Me | iPr | iPr | Me | Br | H | H | H | H | Br | Me |
| | Me | iPr | iPr | iPr | Br | H | H | H | H | Br | iPr |
| | Me | iPr | iPr | OMe | Br | H | H | H | H | Br | OMe |
| | Me | iPr | iPr | H | $SO_3H$ | H | H | H | H | H | H |
| | Me | iPr | iPr | Me | $SO_3H$ | H | H | H | H | H | Me |
| | Me | iPr | iPr | iPr | $SO_3H$ | H | H | H | H | H | iPr |
| | Me | iPr | iPr | OMe | $SO_3H$ | H | H | H | H | H | OMe |
| | Me | iPr | iPr | H | $SO_3H$ | H | H | H | H | $SO_3H$ | H |
| | Me | iPr | iPr | Me | $SO_3H$ | H | H | H | H | $SO_3H$ | Me |
| | Me | iPr | iPr | iPr | $SO_3H$ | H | H | H | H | $SO_3H$ | iPr |
| | Me | iPr | iPr | OMe | $SO_3H$ | H | H | H | H | $SO_3H$ | OMe |
| | Me | iPr | iPr | Me | H | H | H | H | H | H | H |
| | Me | iPr | iPr | iPr | H | H | H | H | H | H | H |
| | Me | iPr | iPr | OMe | H | H | H | H | H | H | H |
| | Me | iPr | iPr | Me | H | H | H | H | Me | H | Me |
| | Me | Cy | Cy | Me | H | H | H | H | H | H | Me |
| | Me | Cy | Cy | iPr | H | H | H | H | H | H | iPr |
| | Me | Cy | Cy | OMe | H | H | H | H | H | H | OMe |
| | Me | Cy | Cy | H | Br | H | H | H | H | Br | H |
| | Me | Cy | Cy | Me | Br | H | H | H | H | Br | Me |
| | Me | Cy | Cy | iPr | Br | H | H | H | H | Br | iPr |
| | Me | Cy | Cy | OMe | Br | H | H | H | H | Br | OMe |
| | Me | Cy | Cy | H | $SO_3H$ | H | H | H | H | H | H |
| | Me | Cy | Cy | Me | $SO_3H$ | H | H | H | H | H | Me |
| | Me | Cy | Cy | iPr | $SO_3H$ | H | H | H | H | H | iPr |
| | Me | Cy | Cy | OMe | $SO_3H$ | H | H | H | H | H | OMe |
| | Me | Cy | Cy | H | $SO_3H$ | H | H | H | H | $SO_3H$ | H |
| | Me | Cy | Cy | Me | $SO_3H$ | H | H | H | H | $SO_3H$ | Me |
| | Me | Cy | Cy | iPr | $SO_3H$ | H | H | H | H | $SO_3H$ | iPr |

-continued

| No. | R | R' | R" | R11 | R12 | R13 | R14 | R15 | R16 | R17 | R18 |
|---|---|---|---|---|---|---|---|---|---|---|---|
|  | Me | Cy | Cy | OMe | SO3H | H | H | H | H | SO3H | OMe |
|  | Me | Cy | Cy | Me | H | H | H | H | H | H | H |
|  | Me | Cy | Cy | iPr | H | H | H | H | H | H | H |
|  | Me | Cy | Cy | OMe | H | H | H | H | H | H | H |
|  | Me | Cy | Cy | Me | H | H | H | H | Me | H | Me |
|  | Me | tBu | nBu | H | H | H | H | H | H | H | H |
|  | Me | tBu | nBu | Me | H | H | H | H | H | H | Me |
|  | Me | tBu | nBu | iPr | H | H | H | H | H | H | iPr |
|  | Me | tBu | nBu | OMe | H | H | H | H | H | H | OMe |
|  | Me | tBu | nBu | H | Br | H | H | H | H | Br | H |
|  | Me | tBu | nBu | Me | Br | H | H | H | H | Br | Me |
|  | Me | tBu | nBu | iPr | Br | H | H | H | H | Br | iPr |
|  | Me | tBu | nBu | OMe | Br | H | H | H | H | Br | OMe |
|  | Me | tBu | nBu | H | SO3H | H | H | H | H | H | H |
|  | Me | tBu | nBu | Me | SO3H | H | H | H | H | H | Me |
|  | Me | tBu | nBu | iPr | SO3H | H | H | H | H | H | iPr |
|  | Me | tBu | nBu | OMe | SO3H | H | H | H | H | H | OMe |
|  | Me | tBu | nBu | H | SO3H | H | H | H | H | SO3H | H |
|  | Me | tBu | nBu | Me | SO3H | H | H | H | H | SO3H | Me |
|  | Me | tBu | nBu | iPr | SO3H | H | H | H | H | SO3H | iPr |
|  | Me | tBu | nBu | OMe | SO3H | H | H | H | H | SO3H | OMe |
|  | Me | tBu | nBu | Me | H | H | H | H | H | H | H |
|  | Me | tBu | nBu | iPr | H | H | H | H | H | H | H |
|  | Me | tBu | nBu | OMe | H | H | H | H | H | H | H |
|  | Me | tBu | nBu | Me | H | H | H | H | Me | H | Me |
|  | Et | iPr | iPr | Me | H | H | H | H | H | H | Me |
|  | Et | iPr | iPr | iPr | H | H | H | H | H | H | iPr |
|  | Et | iPr | iPr | OMe | H | H | H | H | H | H | OMe |
|  | Et | iPr | iPr | Me | Br | H | H | H | H | Br | Me |
|  | Et | iPr | iPr | iPr | Br | H | H | H | H | Br | iPr |
|  | Et | iPr | iPr | OMe | Br | H | H | H | H | Br | OMe |
|  | Et | iPr | iPr | H | SO3H | H | H | H | H | H | H |
|  | Et | iPr | iPr | Me | SO3H | H | H | H | H | H | Me |
|  | Et | iPr | iPr | iPr | SO3H | H | H | H | H | H | iPr |
|  | Et | iPr | iPr | OMe | SO3H | H | H | H | H | H | OMe |
|  | Et | iPr | iPr | H | SO3H | H | H | H | H | SO3H | H |
|  | Et | iPr | iPr | Me | SO3H | H | H | H | H | SO3H | Me |
|  | Et | iPr | iPr | iPr | SO3H | H | H | H | H | SO3H | iPr |
|  | Et | iPr | iPr | OMe | SO3H | H | H | H | H | SO3H | OMe |
|  | Et | iPr | iPr | Me | H | H | H | H | H | H | H |
|  | Et | iPr | iPr | iPr | H | H | H | H | H | H | H |
|  | Et | iPr | iPr | OMe | H | H | H | H | H | H | H |
|  | Et | iPr | iPr | Me | H | H | H | H | Me | H | Me |
|  | Et | Cy | Cy | Me | H | H | H | H | H | H | Me |
|  | Et | Cy | Cy | iPr | H | H | H | H | H | H | iPr |
|  | Et | Cy | Cy | OMe | H | H | H | H | H | H | OMe |
|  | Et | Cy | Cy | H | Br | H | H | H | H | Br | H |
|  | Et | Cy | Cy | Me | Br | H | H | H | H | Br | Me |
|  | Et | Cy | Cy | iPr | Br | H | H | H | H | Br | iPr |
|  | Et | Cy | Cy | OMe | Br | H | H | H | H | Br | OMe |
|  | Et | Cy | Cy | Me | SO3H | H | H | H | H | H | Me |
|  | Et | Cy | Cy | iPr | SO3H | H | H | H | H | H | iPr |
|  | Et | Cy | Cy | OMe | SO3H | H | H | H | H | H | OMe |
|  | Et | Cy | Cy | H | SO3H | H | H | H | H | SO3H | H |
|  | Et | Cy | Cy | Me | SO3H | H | H | H | H | SO3H | Me |
|  | Et | Cy | Cy | iPr | SO3H | H | H | H | H | SO3H | iPr |
|  | Et | Cy | Cy | OMe | SO3H | H | H | H | H | SO3H | OMe |
|  | Et | Cy | Cy | iPr | H | H | H | H | H | H | H |
|  | Et | Cy | Cy | OMe | H | H | H | H | H | H | H |
|  | Et | Cy | Cy | Me | H | H | H | H | Me | H | Me |
|  | Et | tBu | nBu | Me | H | H | H | H | H | H | Me |
|  | Et | tBu | nBu | iPr | H | H | H | H | H | H | iPr |
|  | Et | tBu | nBu | OMe | H | H | H | H | H | H | OMe |
|  | Et | tBu | nBu | H | Br | H | H | H | H | Br | H |
|  | Et | tBu | nBu | Me | Br | H | H | H | H | Br | Me |
|  | Et | tBu | nBu | iPr | Br | H | H | H | H | Br | iPr |
|  | Et | tBu | nBu | OMe | Br | H | H | H | H | Br | OMe |
|  | Et | tBu | nBu | H | SO3H | H | H | H | H | H | H |
|  | Et | tBu | nBu | Me | SO3H | H | H | H | H | H | Me |
|  | Et | tBu | nBu | iPr | SO3H | H | H | H | H | H | iPr |
|  | Et | tBu | nBu | OMe | SO3H | H | H | H | H | H | OMe |
|  | Et | tBu | nBu | H | SO3H | H | H | H | H | SO3H | H |
|  | Et | tBu | nBu | Me | SO3H | H | H | H | H | SO3H | Me |
|  | Et | tBu | nBu | iPr | SO3H | H | H | H | H | SO3H | iPr |
|  | Et | tBu | nBu | OMe | SO3H | H | H | H | H | SO3H | OMe |
|  | Et | tBu | nBu | Me | H | H | H | H | H | H | H |
|  | Et | tBu | nBu | iPr | H | H | H | H | H | H | H |
|  | Et | tBu | nBu | OMe | H | H | H | H | H | H | H |

-continued

| No. | R | R' | R" | R¹¹ | R¹² | R¹³ | R¹⁴ | R¹⁵ | R¹⁶ | R¹⁷ | R¹⁸ |
|---|---|---|---|---|---|---|---|---|---|---|---|
| | Et | tBu | nBu | Me | H | H | H | H | Me | H | Me |
| | Bn | iPr | iPr | Me | H | H | H | H | H | H | Me |
| | Bn | iPr | iPr | iPr | H | H | H | H | H | H | iPr |
| | Bn | iPr | iPr | OMe | H | H | H | H | H | H | OMe |
| | Bn | iPr | iPr | H | Br | H | H | H | H | Br | H |
| | Bn | iPr | iPr | Me | Br | H | H | H | H | Br | Me |
| | Bn | iPr | iPr | iPr | Br | H | H | H | H | Br | iPr |
| | Bn | iPr | iPr | OMe | Br | H | H | H | H | Br | OMe |
| | Bn | iPr | iPr | H | SO₃H | H | H | H | H | H | H |
| | Bn | iPr | iPr | Me | SO₃H | H | H | H | H | H | Me |
| | Bn | iPr | iPr | iPr | SO₃H | H | H | H | H | H | iPr |
| | Bn | iPr | iPr | OMe | SO₃H | H | H | H | H | H | OMe |
| | Bn | iPr | iPr | H | SO₃H | H | H | H | H | SO₃H | H |
| | Bn | iPr | iPr | Me | SO₃H | H | H | H | H | SO₃H | Me |
| | Bn | iPr | iPr | iPr | SO₃H | H | H | H | H | SO₃H | iPr |
| | Bn | iPr | iPr | OMe | SO₃H | H | H | H | H | SO₃H | OMe |
| | Bn | iPr | iPr | Me | H | H | H | H | H | H | H |
| | Bn | iPr | iPr | iPr | H | H | H | H | H | H | H |
| | Bn | iPr | iPr | OMe | H | H | H | H | H | H | H |
| | Bn | iPr | iPr | Me | H | H | H | H | Me | H | Me |
| | Bn | Cy | Cy | Me | H | H | H | H | H | H | Me |
| | Bn | Cy | Cy | iPr | H | H | H | H | H | H | iPr |
| | Bn | Cy | Cy | OMe | H | H | H | H | H | H | OMe |
| | Bn | Cy | Cy | H | Br | H | H | H | H | Br | H |
| | Bn | Cy | Cy | Me | Br | H | H | H | H | Br | Me |
| | Bn | Cy | Cy | iPr | Br | H | H | H | H | Br | iPr |
| | Bn | Cy | Cy | OMe | Br | H | H | H | H | Br | OMe |
| | Bn | Cy | Cy | H | SO₃H | H | H | H | H | H | H |
| | Bn | Cy | Cy | Me | SO₃H | H | H | H | H | H | Me |
| | Bn | Cy | Cy | iPr | SO₃H | H | H | H | H | H | iPr |
| | Bn | Cy | Cy | OMe | SO₃H | H | H | H | H | H | OMe |
| | Bn | Cy | Cy | H | SO₃H | H | H | H | H | SO₃H | H |
| | Bn | Cy | Cy | Me | SO₃H | H | H | H | H | SO₃H | Me |
| | Bn | Cy | Cy | iPr | SO₃H | H | H | H | H | SO₃H | iPr |
| | Bn | Cy | Cy | OMe | SO₃H | H | H | H | H | SO₃H | OMe |
| | Bn | Cy | Cy | Me | H | H | H | H | H | H | H |
| | Bn | Cy | Cy | iPr | H | H | H | H | H | H | H |
| | Bn | Cy | Cy | OMe | H | H | H | H | H | H | H |
| | Bn | Cy | Cy | Me | H | H | H | H | Me | H | Me |
| | Bn | tBu | nBu | Me | H | H | H | H | H | H | Me |
| | Bn | tBu | nBu | iPr | H | H | H | H | H | H | iPr |
| | Bn | tBu | nBu | OMe | H | H | H | H | H | H | OMe |
| | Bn | tBu | nBu | H | Br | H | H | H | H | Br | H |
| | Bn | tBu | nBu | Me | Br | H | H | H | H | Br | Me |
| | Bn | tBu | nBu | iPr | Br | H | H | H | H | Br | iPr |
| | Bn | tBu | nBu | OMe | Br | H | H | H | H | Br | OMe |
| | Bn | tBu | nBu | H | SO₃H | H | H | H | H | H | H |
| | Bn | tBu | nBu | Me | SO₃H | H | H | H | H | H | Me |
| | Bn | tBu | nBu | iPr | SO₃H | H | H | H | H | H | iPr |
| | Bn | tBu | nBu | OMe | SO₃H | H | H | H | H | H | OMe |
| | Bn | tBu | nBu | H | SO₃H | H | H | H | H | SO₃H | H |
| | Bn | tBu | nBu | Me | SO₃H | H | H | H | H | SO₃H | Me |
| | Bn | tBu | nBu | iPr | SO₃H | H | H | H | H | SO₃H | iPr |
| | Bn | tBu | nBu | OMe | SO₃H | H | H | H | H | SO₃H | OMe |
| | Bn | tBu | nBu | Me | H | H | H | H | H | H | H |
| | Bn | tBu | nBu | iPr | H | H | H | H | H | H | H |
| | Bn | tBu | nBu | OMe | H | H | H | H | H | H | H |
| | Bn | tBu | nBu | Me | H | H | H | H | Me | H | Me |
| | Ph | iPr | iPr | Me | H | H | H | H | H | H | Me |
| | Ph | iPr | iPr | iPr | H | H | H | H | H | H | iPr |
| | Ph | iPr | iPr | OMe | H | H | H | H | H | H | OMe |
| | Ph | iPr | iPr | H | Br | H | H | H | H | Br | H |
| | Ph | iPr | iPr | Me | Br | H | H | H | H | Br | Me |
| | Ph | iPr | iPr | iPr | Br | H | H | H | H | Br | iPr |
| | Ph | iPr | iPr | OMe | Br | H | H | H | H | Br | OMe |
| | Ph | iPr | iPr | H | SO₃H | H | H | H | H | H | H |
| | Ph | iPr | iPr | Me | SO₃H | H | H | H | H | H | Me |
| | Ph | iPr | iPr | iPr | SO₃H | H | H | H | H | H | iPr |
| | Ph | iPr | iPr | OMe | SO₃H | H | H | H | H | H | OMe |
| | Ph | iPr | iPr | H | SO₃H | H | H | H | H | SO₃H | H |
| | Ph | iPr | iPr | Me | SO₃H | H | H | H | H | SO₃H | Me |
| | Ph | iPr | iPr | iPr | SO₃H | H | H | H | H | SO₃H | iPr |
| | Ph | iPr | iPr | OMe | SO₃H | H | H | H | H | SO₃H | OMe |
| | Ph | iPr | iPr | Me | H | H | H | H | H | H | H |
| | Ph | iPr | iPr | iPr | H | H | H | H | H | H | H |
| | Ph | iPr | iPr | OMe | H | H | H | H | H | H | H |
| | Ph | iPr | iPr | Me | H | H | H | H | Me | H | Me |
| | Ph | Cy | Cy | H | H | H | H | H | H | H | H |

-continued

| No. | R | R' | R" | R¹¹ | R¹² | R¹³ | R¹⁴ | R¹⁵ | R¹⁶ | R¹⁷ | R¹⁸ |
|---|---|---|---|---|---|---|---|---|---|---|---|
| | Ph | Cy | Cy | Me | H | H | H | H | H | H | Me |
| | Ph | Cy | Cy | iPr | H | H | H | H | H | H | iPr |
| | Ph | Cy | Cy | OMe | H | H | H | H | H | H | OMe |
| | Ph | Cy | Cy | H | Br | H | H | H | H | Br | H |
| | Ph | Cy | Cy | Me | Br | H | H | H | H | Br | Me |
| | Ph | Cy | Cy | iPr | Br | H | H | H | H | Br | iPr |
| | Ph | Cy | Cy | OMe | Br | H | H | H | H | Br | OMe |
| | Ph | Cy | Cy | H | SO₃H | H | H | H | H | H | H |
| | Ph | Cy | Cy | Me | SO₃H | H | H | H | H | H | Me |
| | Ph | Cy | Cy | iPr | SO₃H | H | H | H | H | H | iPr |
| | Ph | Cy | Cy | OMe | SO₃H | H | H | H | H | H | OMe |
| | Ph | Cy | Cy | H | SO₃H | H | H | H | H | SO₃H | H |
| | Ph | Cy | Cy | Me | SO₃H | H | H | H | H | SO₃H | Me |
| | Ph | Cy | Cy | iPr | SO₃H | H | H | H | H | SO₃H | iPr |
| | Ph | Cy | Cy | OMe | SO₃H | H | H | H | H | SO₃H | OMe |
| | Ph | Cy | Cy | Me | H | H | H | H | H | H | H |
| | Ph | Cy | Cy | iPr | H | H | H | H | H | H | H |
| | Ph | Cy | Cy | OMe | H | H | H | H | H | H | H |
| | Ph | Cy | Cy | Me | H | H | H | H | Me | H | Me |
| | Ph | tBu | nBu | H | H | H | H | H | H | H | H |
| | Ph | tBu | nBu | Me | H | H | H | H | H | H | Me |
| | Ph | tBu | nBu | iPr | H | H | H | H | H | H | iPr |
| | Ph | tBu | nBu | OMe | H | H | H | H | H | H | OMe |
| | Ph | tBu | nBu | H | Br | H | H | H | H | Br | H |
| | Ph | tBu | nBu | Me | Br | H | H | H | H | Br | Me |
| | Ph | tBu | nBu | iPr | Br | H | H | H | H | Br | iPr |
| | Ph | tBu | nBu | OMe | Br | H | H | H | H | Br | OMe |
| | Ph | tBu | nBu | H | SO₃H | H | H | H | H | H | H |
| | Ph | tBu | nBu | Me | SO₃H | H | H | H | H | H | Me |
| | Ph | tBu | nBu | iPr | SO₃H | H | H | H | H | H | iPr |
| | Ph | tBu | nBu | OMe | SO₃H | H | H | H | H | H | OMe |
| | Ph | tBu | nBu | H | SO₃H | H | H | H | H | SO₃H | H |
| | Ph | tBu | nBu | Me | SO₃H | H | H | H | H | SO₃H | Me |
| | Ph | tBu | nBu | iPr | SO₃H | H | H | H | H | SO₃H | iPr |
| | Ph | tBu | nBu | OMe | SO₃H | H | H | H | H | SO₃H | OMe |
| | Ph | tBu | nBu | Me | H | H | H | H | H | H | H |
| | Ph | tBu | nBu | iPr | H | H | H | H | H | H | H |
| | Ph | tBu | nBu | OMe | H | H | H | H | H | H | H |
| | Ph | tBu | nBu | Me | H | H | H | H | Me | H | Me |

The bromine radicals (e.g. in phosphine compound no. 31) allow an easy introduction of additional functional groups.

Especially preferred are the following fluorenyl-substituted phosphine compounds:

(9-methylfluoren-9-yl)diisopropylphosphine (9-MeFlu-PiPr₂) (5),

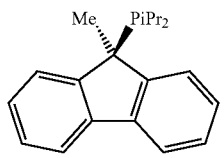

(5)

(9-ethylfluoren-9-yl)diisopropylphosphine (9-EtFluPiPr₂) (6),

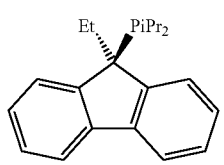

(6)

(9-benzylfluoren-9-yl)diisopropylphosphine (9-BnFluPiPr₂) (26),

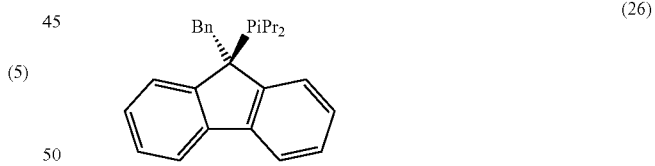

(26)

(9-octadecylfluoren-9-yl)diisopropylphosphine (9-C₁₈H₃₇FluPiPr₂) (7),

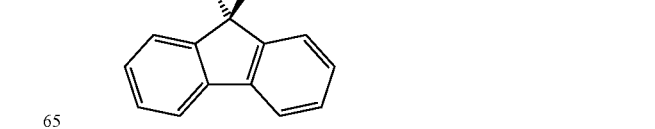

(7)

(9-methylfluoren-9-yl)dicyclohexylphosphine (9-MeF-luPCy₂) (8),

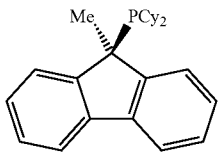
(8)

(9-ethylfluoren-9-yl)dicyclohexylphosphine (9-EtFluPCy₂) (9),

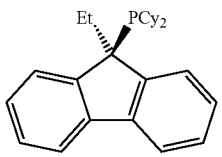
(9)

(9-benzylfluoren-9-yl)dicyclohexylphosphine (9-BnF-luPCy₂) (10),

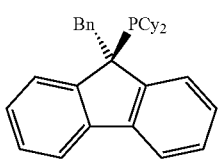
(10)

(9-octadecylfluoren-9-yl)dicyclohexylphosphine (9-C₁₈H₃₇FluPCy₂) (11)

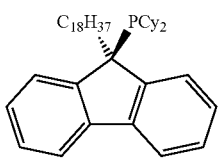
(11)

(1-methyl-9-ethylfluoren-9-yl)dicyclohexylphosphine (9-Et-1-MeFluPCy₂) (12),

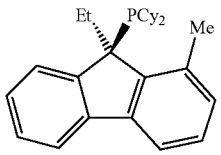
(12)

(9-ethyl-2-sulfofluoren-9-yl)dicyclohexylphosphine (2-SO₃H-9-EtFluPCy₂) (13),

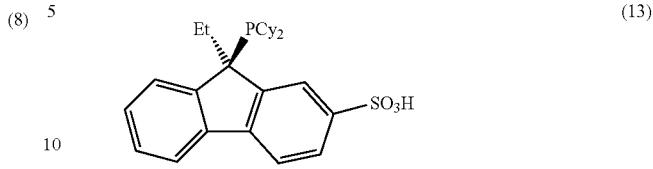
(13)

and their corresponding phosphonium salts
9-MeFluPiPr₂.H⁺Y⁻ (5a),
9-EtFluPiPr₂.H⁺Y⁻ (6a),
9-BnFluPiPr₂.H⁺Y⁻ (26a),
9-C₁₈H₃₇FluPiPr₂.H⁺Y⁻ (7a),
9-MeFluPCy₂.H⁺Y⁻ (8a),
9-EtFluPCy₂.H⁺Y⁻ (9a),
9-BnFluPCy₂.H⁺Y⁻ (10a),
9-C₁₈H₃₇FluPCy₂.H⁺Y⁻ (11a),
9-Et-1-MeFluPCy₂.H⁺Y⁻ (12a), and
9-Et-2-SO₃HFluPCy₂.H⁺Y⁻ (13a).
wherein Flu represents a fluoren-9-yl radical, and Et, Bn, Cy, iPr, and Me have the meanings defined above.

In all the preceding formulae Y⁻ represents an anion, preferably a non-coordinating, non-basic anion such as BF₄⁻.

A general route for the preparation of the new phosphine compounds is as follows: A compound according to the formula HCp$^s$ having the desired substitutions, typically a substituted cyclopentadiene, a substituted indene, or an unsubstituted or substituted fluorene, is first reacted with a strong base, typically n-BuLi, to abstract a proton and a resonance stabilized carbanion is formed. Next, the anion is reacted with a phosphinous halide according to the formula R'R"PX, wherein R' and R" are defined as above and X is Cl or Br, preferably Cl, to result in the respective Cp$^s$-substituted phosphine which is conveniently converted into the respective phosphonium salts for easier storage and handling (e.g. by reacting with HBF₄). This method is advantageously used to prepare phosphine compounds wherein R' and R" in formulae (1) or (1a) are the same radicals as the corresponding phosphinous halides are easily available.

Depending on the desired substituents at the Cp$^s$ ring system it is required in some cases to prepare first a cyclopentadienyl-, indenyl- or fluorenyl-substituted phosphine compound and then perform the appropriate reactions to result in the desired substitutions at the Cp$^s$ ring system. An example is the preparation of a sulfonated fluorenyl-substituted phosphine wherein a fluorenyl-substituted phosphonium salt is reacted with sulfuric acid to introduce an —SO₃ group at the fluorenyl radical.

Another modification of the general method becomes necessary when the R' and R" radicals are different and the corresponding phosphinous halide R'R"PX is not readily available. A compound according to the formula HCp$^s$ having the desired substitutions, typically a substituted cyclopentadiene, a substituted indene, or an unsubstituted or substituted fluorene, is first reacted with a strong base, typically n-BuLi, to abstract a proton and a resonance stabilized carbanion is formed. Next, the anion is reacted with a phosphonous dihalide according to the formula R'PX₂ wherein R' is defined as above and X is Cl or Br, preferably Cl, to result in the phosphinous halide according to the formula Cp$^s$R'PX as intermediate product. Cp$^s$R'PX can easily be converted to the desired phosphine R'R"PCp$^s$ by simple alkylation with an appropriate organometallic reagent, such as R"MgX or R"Li wherein R" is a defined above.

All three classes of new phosphine compounds are good ligands in metal complexes. The present inventors believe that e.g. the 9-fluorenyl group as well as the 1-indenyl group acts a an electron-rich alkyl substituent. Moreover, the close proximity of 6-systems seems to facilitate the stabilization of low coordinated metal species. However, the easy availability of the simpler cyclopentadienes, especially the pentamethyl-cyclopentadiene, makes phosphines prepared from these starting compounds also very attractive for economical reasons.

One aspect of the present invention is a coordination compound comprising a phosphine compound as described before (including phosphine compounds according to formulae (A) and (B)) and a transition metal selected from groups 8, 9, 10, and 11 of the Periodic Table of the Elements. Said coordination compounds are effective catalysts or effective parts of catalyst systems for organic synthesis. Said coordination compounds can either be prepared in advance and then used for catalytic reactions or can be formed in situ by adding the phosphine compound or its corresponding phosphonium salt in combination with an appropriate transition metal precursor compound. Thus, another aspect of the present invention is the use the phosphine compound (including phosphine compounds according to formulae (A) and (B)) or its corresponding phosphonium salt (including phosphonium salts according to formulae (Aa) and (Ba)) in combination with a transition metal compound as a catalyst or a part of a catalyst system for the preparation of an organic compound, wherein the transition metal is selected from groups 8, 9, 10, and 11 of the Periodic Table of the Elements. The in situ formation of the catalytically active coordination compound comprising the phosphine compound according to the invention as ligand is often more convenient; however it may also be advantageous to prepare the catalytically active coordination compound comprising the phosphine compound according to the invention as ligand directly and then use it for catalytic applications as this increases the initial catalytic activity in some instances. If it is referred to the "present catalyst" or "catalyst according to the invention" both alternative routes are included.

The transition metal is preferably selected from Pd, Ni, Pt, Rh, Ir, Ru, Co, Fe, Cu, and Au, more preferably it is Pd or Ni and most preferably it is Pd.

Examples of palladium compounds that can be used together with the phosphine compounds according to the invention in order to form in situ the catalytically active coordination compound comprising the phosphine compound as a ligand are palladium(II) acetate, palladium(II) chloride, palladium(II) bromide, sodium tetrachloropalladate (II), palladium (II) acetylacetonate, palladium(0) dibenzylidenacetone complexes, palladium(0) tetrakis(triphenylphosphine), palladium(0) bis(tri-o-tolylphosphine), palladium(II) propionate, palladium(II) (cyclooctadiene-1,5) dichloride, palladium(0)-diallyl ether complexes, palladium (II) nitrate, palladium(II) chloride bis(acetonitrile), palladium(II) chloride bis(benzonitrile) and other palladium(0) and palladium(II) complexes.

Generally, for catalytic applications, the phosphine ligand is used in excess relative to the transition metal. The ratio of transition metal to ligand is preferably from 1:1 to 1:1000. Ratios of transition metal to ligand of 1:1 to 1:100 are particularly preferred. The exact transition metal/ligand ratio to be used depends on the specific application and also on the amount of catalyst used. Thus, in general, it is conventional to use lower transition metal/ligand ratios in the case of very low transition metal concentrations (<0.01 mol %) than in the case of transition metal concentrations of between 0.5 and 0.01 mol % of transition metal.

The present phosphine compounds and their corresponding phosphonium salts are thermally very stable. It is thus possible to use the catalysts according to the invention at reaction temperatures of up to 250° C. or more. The catalysts are preferably used at temperatures of 20 to 200° C.; it has proved advantageous in many cases to work at temperatures of 30 to 180° C., preferably of 40 to 160° C. The ligands can also be used in pressure reactions without loss of activity, the operating pressure conventionally being up to only 100 bar, but preferably in the normal pressure range of up to 60 bar.

The present catalysts are preferably used in couplings reactions wherein a C—C or C-heteroatom bond is formed. However, it is obvious to those skilled in the art that other transition metal-catalyzed reactions, such as the metathesis or hydrogenation of double bonds or carbonyl compounds can also be catalyzed by the present catalysts.

An overview of Pd catalyzed coupling reactions illustrative for reactions that can be catalyzed by the catalysts according to the present invention, i.e. Pd complexes comprising the present phosphine compounds as ligands (prepared in advance or formed in situ), is disclosed in "Palladiumkatalysierte Kupplungen von Arylchloriden", by A. F. Littke and G. C. Fu, Angew. Chem. 2002, 114, 4350-4386.

Examples of C—C coupling reactions are:

(a) Suzuki cross-coupling (also known as Suzuki-Miyaura cross-coupling) of organoboron compounds with aryl, heteroaryl or vinyl halides/pseudohalides: Typically, the organoboron compound is boronic acid of the formula R$^a$—B(OH)$_2$, wherein R$^a$ is an aryl, alkenyl, or alkyl radical, or, although less preferred, a corresponding boronic acid ester. The reaction is conducted in the presence of the Pd complex and a base. The Suszuki cross-coupling is significant to couple aryl and heteroaryl boronic acid with aryl and heteroaryl halides, respectively, resulting in the formation of biaryl compounds.

(b) Stille cross-coupling of organotin compounds with carbon electrophiles comprising a halogen or pseudohalogen as leaving group: Preferably, the carbon electrophile is an aryl, heteroaryl or vinyl halide/pseudohalide, although other electrophiles, such as acid halides, may be used. Typically, the organotin compound has the formula R$^b$Sn(R$^c$)$_3$, wherein the R$^c$ radicals being not transferred are usually butyl or methyl radicals and the R$^b$ radical can be varied broadly, preferably it is an aryl, heteroaryl, alkenyl, alkynyl, or alkyl radical. The reaction is conducted in the presence of the Pd complex. Stille cross-coupling is a popular tool in the synthesis of complex natural products.

(c) Hiyama cross-coupling of organosilanes with aryl, heteroaryl or vinyl halides/pseudohalides: Typically, the organosilane has the formula R$^d$SiZ, wherein Z represents three radicals that are not transferred, e.g. MeCl$_2$, Me$_3$, and (OMe)$_3$, and R$^d$ is, for example, a vinyl, akynyl, or aryl radical. The reaction is conducted in the presence of the Pd catalyst. The Hiyama cross-coupling is an interesting alternative to the Stille cross-coupling as organosilicon compounds are non-toxic.

(d) Negishi cross-coupling of organozinc compounds with aryl, heteroaryl or vinyl halides/pseudohalides: Typically, the organozinc compound has the formula R$^e$ZnX or R$^e$$_2$Zn, wherein X is a halogen or a phenyl radical and R$^e$ is, for example, an aryl, heteroaryl, or alkyl radical. The reaction is conducted in the presence of the Pd catalyst. The Negishi cross-coupling is an effective method for the formation of C—C bonds as organozinc compounds are readily accessible and show a high tolerance against functional groups.

(e) Kumada cross-coupling of Grignard compounds with aryl, heteroaryl or vinyl halides/pseudohalides: In the Grignard compound according to formula R$^f$MgX the R$^f$ radical may be an aryl, heteroaryl, or alkyl radical and X is a halogen. The reaction is conducted in the presence of a Pd or Ni catalyst. The Kumada cross-coupling has reached a high significance in organic synthesis as it has been known for a long time. However, contrary to the coupling reactions mentioned above, its applicability is restricted as Grignard compounds do not tolerate a lot of functional compounds.

(f) Sonogashira cross-coupling of terminal alkynes with aryl, heteroaryl or vinyl halides/pseudohalides: In the terminal alkyne according to formula H—C≡C—R$^f$ the R$^f$ radical can be varied broadly, even including organosilyl radicals. The reaction is conducted in the presence of the Pd catalyst and a Cu cocatalyst, typically CuI.

(g) α-Arylation of enolates and other stabilized carbanions with aryl or heteroaryl halides/pseudohalides: The compounds to be arylated include carbonyl compounds, such as ketones and esters, and nitro compounds. The reaction is conducted in the presence of the Pd catalyst and a base.

(h) Cyanation of aryl or heteroaryl halides/pseudohalides: Typically, the cyanation agent is an inorganic cyanide, such as $Zn(CN)_2$ or KCN. The reaction is conducted in the presence of the Pd catalyst.

(i) Carbonylation of aryl or heteroaryl halides/pseudohalides: An aryl or heteroaryl halide/pseudohalide is reacted with CO and a compound according to the formula HNu, wherein Nu is H ("reductive carbonylation"), —OR, —NR$_2$ or a similar radical. The reaction is conducted in the presence of the Pd catalyst and a base. The Pd catalyzed carbonylation is an effective method for the synthesis of carbonyl compounds, such as aldehydes, esters, and amides, and is of high interest to the chemical industry as its products are valuable intermediate products for the preparation of herbicides and pharmaceuticals.

(j) Heck coupling of aryl, heteroaryl or vinyl halides/pseudohalides to olefins. The reaction is conducted in the presence of the Pd catalyst and a base. As the olefin substrate tolerates a lot of different functionalities, such as ester, ether, carboxy, cyano, and hydroxyl groups, the Heck coupling is one of the most important methods to form C—C bonds.

An example of a C—N coupling reaction is the Buchwald-Hartwig coupling of an aryl or heteroaryl halide/pseudohalide with an amine (Buchwald-Hartwig amination). The amine component can be varied broadly, it includes various secondary and primary alkyl (including cycloalkyl) amine and anilines. The reaction is conducted in the presence of the Pd catalyst and a base. The Buchwald-Hartwig amination is an effective tool for the synthesis of aniline derivatives that play an important role in the preparation of pharmaceuticals, agro chemicals, and in photography.

An example of a reaction resulting in the formation of a C—O bond is the coupling of an aryl or heteroaryl halide/pseudohalide with an alcohol. The Pd catalyzed C—O coupling may be used for substrates that do not couple in the absence of the Pd catalyst under "normal" conditions of the well-known electrophilic substitution. Preferably, the alkoxide employed is NaOtBu or a phenoxide. The reaction is conducted in the presence of the Pd catalyst (and a base, in case the alcohol is employed instead of the alkoxide). The resulting diaryl and arylalkyl ethers play an important role in the synthesis of pharmaceuticals and natural products.

The term "pseuodhalogen" or "pseudohalide" has the standard meaning accepted in the art. Non-limiting examples of pseudohalogens/pseudohalides are —COCl, —SO$_2$Cl, —N$_2$X, —OP(O)(OR)$_2$, —OSO$_2$CF$_3$ (—OTf, triflate), and —OSO$_2$Tol (—OTs, tosylate). The preferred pseudohalides used in the above coupling reactions are the triflates.

The above-mentioned coupling reactions are preferably conducted by using the corresponding chlorides, bromides, or triflates as starting materials, more preferably the corresponding chlorides or bromides are used.

It is understood that the above list of coupling reactions is not limiting and it is immediately evident to the person skilled in the art that the present catalysts can be used in similar coupling reactions.

A further example of a reaction that can be catalyzed the by the catalysts according to the present invention is the dehydrohalogenation, especially dehydrochlorination, of aryl and heteroaryl halides, preferably chlorides and bromides. The dehalogenation of aryl and heteroaryl halides is not only important for the organic synthesis but also for environmental chemistry as the dechlorination of polychlorinated biphenyls (PCB) and related chlorinated arenes represents a mechanism to detoxicate these persistent harmful substances. Although the heterogeneous Pd catalyzed dehalogenation has been used for may years, the new phosphine compounds used as ligands in homogeneous transition metal complexes, preferably Pd complexes, offer a new perspective to dehalogenate aryl and heteroaryl halides under mild conditions.

It is a matter of fact that a transition metal complex comprising a specific phosphine compound as a ligand has not the same effectiveness as catalyst in all different types of reactions with all different types of substrates. A significant advantage of the new phosphine compounds is that they have a variable backbone they allows "catalyst fine tuning", i.e. detailed structural and electronic modifications in order to adapt the ligand to the intended use. Especially the fluorenyl-substituted phosphine compounds can be varied readily: Substituents at the 1- and 8-positions ($R^{11}$ and $R^{18}$) allow to modulate the steric bulk close to the phosphorous atom and the 2- and 7-positions ($R^{12}$ and $R^{17}$) allow the easy introduction of the various functional groups. It is within the ordinary skill of an organic chemist to conduct some routine experiments in order to find out which specific phosphine compound according to the present invention will be the appropriate ligand in a transition metal catalyst to function as an highly effective catalyst for the preparation of a selected product. In general, reactions using the present catalysts produce the desired products in high yield, with high catalytic productivity, and/or with high purity. In many cases, the new catalysts possess the ability to employ the less reactive, but cost-effective chlorides.

The following examples illustrate the preparation of the new phosphine compounds and/or their corresponding phosphonium salts. The exemplary use of some of the synthesized compounds in various coupling reactions is also illustrated.

EXAMPLES

All chemicals were purchased as reagent grade from commercial suppliers and used without further purification, unless otherwise noted. THF was distilled over potassium and benzophenone under an argon atmosphere, diethylether was distilled over sodium/potassium alloy and benzophenone under an argon atmosphere. Diisopropylamine was dried over potassium hydroxide, dioxane was dried over calcium hydride. Proton ($^1$H NMR), carbon ($^{13}$C NMR) and phosphorus ($^{31}$P NMR) nuclear magnetic resonance spectra were recorded on Bruker DRX 500 at 500 MHz, 125.75 MHz and 202.46, respectively or on Bruker DRX 300 at 300 MHz and 75.07 MHz respectively. The chemical shifts are given in parts per million (ppm) on the delta scale (δ) and are referenced to tetramethylsilane (δ=0 ppm), $^1$H NMR and 65% aq. H$_3$PO$_4$. (δ=0 ppm). $^{31}$P NMR. Abbreviations for NMR data: s=singlet; d=doublet; t=triplet; q=quartet; dd=doublet of doublets; dt=doublet of triplets; dq=doublet of quartets; tt=triplet of triplets; m=multiplet. IR-spectra were recorded on Perkin Elmer 1600 series FT-IR. Mass spectra were recorded on a Finigan MAT 95 magnetic sector spectrometer. Thin layer chromatograpy (TLC) was performed using Fluka silica gel 60 F 254 (0.2 mm) on aluminum plates. Silica gel columns for chromatography were prepared with E. Merck silica gel 60 (0.063-0.20 mesh ASTM). Fluorene was purchased from Aldrich and used as received.

The radicals R, R$_1$, R$_2$, etc. do not have the same meanings as defined in the general part of the description, but the meanings as evident from the examples.

A. PREPARATION OF PHOSPHINE COMPOUNDS

I. Preparation of Cyclopentadienyl Phosphonium Salts

General procedure for the synthesis of Cp* phosphonium salts:

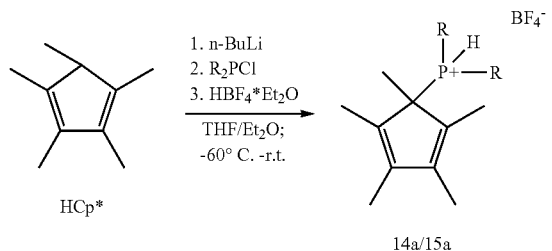

Synthesis of Cp*PCy$_2$.HBF$_4$ (14a)

In a 250 ml Schlenk flask pentamethylcyclopentadiene (HCp*) (2.9 g, 21.3 mmol) was dissolved in diethylether, abs (100 ml) and treated with n-BuLi (8.1 ml, 2.5 M in hexane, 20.3 mmol) at −60° C. The mixture was stirred for 4 h at ambient temperature, to give a thick white suspension. THF, abs (100 ml) was added and the suspension was quenched with Cy$_2$PCl (3.93 g, 16.9 mmol) at −60° C. The reaction mixture was stirred at ambient temperature overnight, then filtered over a small pad of Celite® filter aid using a Schlenk technique. The clear, colorless filtrate was then quenched with HBF$_4$.Et$_2$O (2.7 ml, 19.9 mmol) which led to precipitation of the phosphonium salt as a white solid about 3 minutes after the addition of the acid. The solid was separated via suction filtration, washed with Et$_2$O, and the volatiles removed in vacuo to afford 14a as a white solid (3.7 g, 52%).

$^1$H NMR (500 MHz, CDCl$_3$) δ [ppm] 6.06 (dt, $^1$J=470 Hz, $^3$J=4 Hz 1H, PH), 2.15-2.07 (m, 2H, CH), 2.03-1.99 (m, 2H, CH$_2$), 1.98 (s, 6H, CH$_3$), 1.89 (d, $^4$J(PH)=3.5 Hz, 6H, CH$_3$), 1.89-1.85 (m, 6H, CH$_2$), 1.73-1.56 (m, 6H, CH$_2$), 1.51 (d, $^3$J(PH)=17.5 Hz, 3H, CH$_3$), 1.32-1.25 (m, 6H, CH$_2$); $^{13}$C{$^1$H} NMR (125.75 MHz, CDCl$_3$) δ [ppm] 142.7 (d, $^{P-C}$J=6.8 Hz), 134.8, 55.1 (d, $^{P-C}$J=28.3 Hz), 30.3, 30.0, 29.6 (d, $^{P-C}$J=3.5 Hz), 28.5 (d, $^{P-C}$J=3.4 Hz), 26.9 (d, $^{P-C}$J=11.9 Hz), 26.7 (d, $^{P-C}$J=13.6 Hz), 25.0, 17.3 (d, $^{P-C}$J=3.3 Hz), 11.4 (d, $^{P-C}$J=22.1 Hz); $^{31}$P{$^1$H} NMR (202.45 MHz, CDCl$_3$) δ [ppm] 26.7; $^{31}$P NMR (202.45 MHz, CDCl$_3$) δ [ppm] 26.7 (d, $^{P-H}$J=471.5 Hz).

Synthesis of Cp*PiPr$_2$.HBF$_4$ (15a)

In a 250 ml Schlenk flask pentamethylcyclopentadiene (HCp*) (2.79 g, 20.5 mmol) was dissolved in diethylether, abs (175 ml) and treated with n-BuLi (7.8 ml of a 2.5 M solution in hexane, 19.5 mmol) at −60° C. The mixture was stirred for 4 h at ambient temperature (magnetic stirrer), to result in a thick white suspension. THF, abs (50 ml) was added, followed by iPr$_2$PCl (2.48 g, 16.25 mmol) at −60° C. The reaction mixture was stirred at ambient temperature overnight, filtered over a small pad of Celite®. The clear, colorless filtrate was quenched with HBF$_4$.Et$_2$O (2.76 ml, 20.3 mmol) which led to precipitation of the phosphonium salt as a white solid. The solid was separated via suction filtration, washed with Et$_2$O, and the volatiles removed in vacuo to afford 15a as a white solid (5.2 g, 94%).

$^1$H NMR (500 MHz, CDCl$_3$) δ [ppm] 6.21 (dt, $^1$J=468.5 Hz, $^3$J=4.5 Hz 1H, PH), 2.52-2.43 (m, 2H, CH), 2.00 (s, 6H, CH$_3$), 1.89 (d, $^4$J(PH)=3.0 Hz, 6H, CH$_3$), 1.51 (d, $^3$J(PH)= 17.5 Hz, 3H, CH$_3$), 1.47 (dd, $^3$J(PH)=18.5 Hz, $^3$J=7.0 Hz, 6H, CH$_3$), 1.38 (dd, $^3$J(PH)=18 Hz, $^3$J=7.5 Hz, 6H, CH$_3$); $^{13}$C{$^1$H} NMR (125.75 MHz, CDCl$_3$) δ [ppm] 143.2 (d, $^{P-C}$J=6.7 Hz), 135.0, 55.2 (d, $^{P-C}$J=29.2 Hz), 20.8 (d, $^{P-C}$J=38.4 Hz), 20.1 (d, $^{P-C}$J=2.5 Hz), 18.8 (d, $^{P-C}$J=3.3 Hz), 18.1 (d, $^{P-C}$J=3.4 Hz), 11.8 (d, $^{P-C}$J=39.4 Hz); $^{31}$P{$^1$H} NMR (202.45 MHz, CDCl$_3$) δ [ppm] 34.9; $^{31}$P NMR (202.45 MHz, CDCl$_3$) δ [ppm] 34.9 (d, $^{P-H}$J=469.3 Hz).

II. Preparation of Indenyl Derivatives and Precursors

Synthesis of Tigloyl Chloride (33)

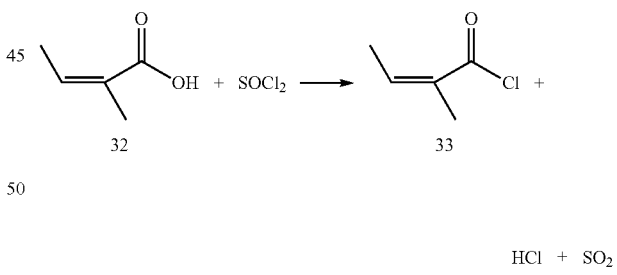

Tiglic acid (32) (100.0 g, 1.00 mol) and thionyl chloride (178.4 g, 1.5 mol) were placed in a 500 ml round bottomed flask fitted with a magnetic stirring apparatus and a reflux condenser. The mixture was refluxed until the development of HCl gas was completed. Then the reflux condenser was replaced by a distillation head. Excess of thionyl chloride was removed at 100-130° C. at ambient pressure, followed by tigloyl chloride (33) (106.32 g, 1.06 mol, 89%) as a colorless liquid at 140-145° C. The $^1$H NMR spectrum was identical with the literature (T. E. Ready, J. C. W. Chien, M. D. Rausch, J. Org. Chem. 1999 583, 11-27; B. B. Snider, Q. Che, Org. Lett. 2004, 6, 17, 2877-2880).

$^1$H NMR (200 MHz, CDCl$_3$): δ [ppm] 7.33 (q, $^3$J=6.3 Hz, 1H, CH), 1.93 (d, $^3$J=9.7 Hz, 3H, CH$_3$CH), 1.91 (s, 3H, CH$_3$).

Synthesis of 2,3-dimethyl-1-indanone (34)

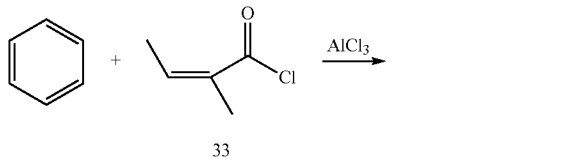

Under an argon atmosphere benzene (335 ml, 3.74 mol) and aluminum trichloride (90.78 g, 0.68 mol) were introduced into a 1 liter three necked round bottomed flask fitted with a magnetic stirring apparatus, an addition funnel and a reflux condenser. The stirred orange mixture was cooled to 7° C. and tigloyl chloride (33) (40 g, 0.34 mol) was added dropwise via an addition funnel. After completion of the addition, the mixture was allowed to come to room temperature and then refluxed overnight. Then the reaction mixture was allowed to come to room temperature and poured onto mixture of ice (300 g) and conc. HCl (50 ml). The organic layer was separated and washed with a saturated solution of sodium bicarbonate (3×100 ml), then dried over magnesium sulfate and filtered. The excess benzene was removed under reduced pressure to afford (34) (50.02 g, 92%) as a yellow liquid. The $^1$H NMR spectrum was identical with the literature (T. E. Ready, J. C. W. Chien, M. D. Rausch, J. Org. Chem. 1999 583, 11-27; J. Sarrazin, A. Tallec, Tetrahedron Letters, 1977, 18, 1579-1582; M. Hiscock, G. B. Porter, J. Chem. Soc. (B), 1971, 1631-1634). $^1$H NMR (200 MHz, CDCl$_3$): δ [ppm] 7.76-7.34 (m, 4H, arom), 2.94 (dq, $^3$J=4.9 Hz, $^3$J=7.0 Hz, 1H, H-position 2), 2.24 (dq, $^3$J=7.3 Hz, $^3$J=4.7 Hz, 1H, H-position 3), 1.46 (d, $^3$J=6.9 Hz, 3H, CH$_3$-position 2), 1.32 (d, $^3$J=7.3 Hz, 3H, CH$_3$-position 3).

Synthesis of 2,3,4,7-tetramethyl-1-indanone (35)

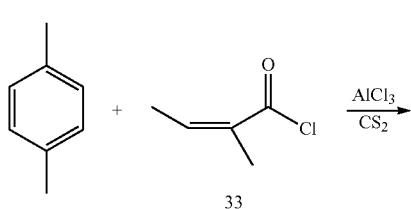

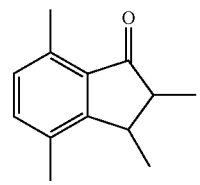

Under an argon atmosphere AlCl$_3$ (64 g, 0.48 mol) and CS$_2$ (250 ml) were placed in a 1 liter three necked round bottomed flask fitted with a magnetic stirring apparatus, an addition funnel, an inner thermometer and a reflux condenser. A mixture of tigloyl chloride (33) (42 g, 0.35 mol) and p-xylene (42.8 ml, 0.35 mol) was added over a period of 1 h at −10° C. under vigorous stirring. After 2 h stirring at −10° C. the mixture was allowed to come to ambient temperature and was stirred at that temperature overnight. The brown reaction mixture was then refluxed for 3 h, after cooling to ambient temperature the reaction mixture was poured carefully onto a mixture of concentrated HCl (300 ml) and ice (500 g). Then the mixture was transferred into a separation funnel, the lower CS$_2$ layer was separated and the aqueous layer extracted with diethyl ether (3×100 ml). The combined organic layers were dried over magnesium sulfate, filtered, and the solvents removed in a rotary evaporator to give a red brown liquid. This residue was rectified using a 35 cm Vigreux column to afford 2,3,4,7-tetramethyl-1-indanone (35) (34 g, 52%, 95-100° C., 1.5-1.2 mbar) as a pale yellow liquid. (35) was found to be a mixture of the two isomers of 2,3,4,7-tetramethyl-1-indanone (35a to 35b approximately 3:1). The $^1$H NMR spectrum was identical with the literature (S. Barlow, D. R. Cary, M. J. Drewitt, D. O'Hare, J. Chem. Soc. Dalton Trans. 1997 3867-3878).

$^1$H NMR: (300 MHz, CDCl$_3$): δ [ppm] 35a δ 7.23 (d, $^3$J=7.5 Hz, 1H, arom), 7.02 (d, $^3$J=7.5 Hz, 1H, arom), 2.96 (qd, $^3$J=7.2 Hz, $^3$J=2.4 Hz, 1H, CH-position 2), 2.59 (s, 3H, benzylic CH$_3$), 2.37 (s, 3H, benzylic CH$_3$), 2.25 (qd, $^3$J=7.5 Hz, $^3$J=2.4, 1H, CH-position 3), 1.34 (d, $^3$J=7 Hz, 3H, CHCH$_3$-position 2), 1.26 (d, $^3$J=7.2 Hz, 3H, CHCH$_3$-position 3); 35b δ 7.22 (d, $^3$J=7.5 Hz, 1H, arom), 7.01 (d, $^3$J=7.5 Hz, 1H, arom), 3.48 (qui, $^3$J=7.2 Hz, 1H, CH-position 2), 2.77 (qui, $^3$J=7.5 Hz, 1H, CH-position 3), 2.59 (s, 3H, benzylic CH$_3$), 2.37 (s, 3H, benzylic CH$_3$), 1.24 (d, $^3$J=7.5 Hz, 3H, CHCH$_3$-position 2), 1.09 (d, $^3$J=7.2 Hz, 3H, CHCH$_3$-position 3).

Synthesis of 4,7-dimethoxy-2,3-dimethyl-1-indanone (36)

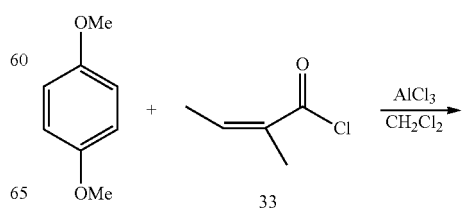

Synthesis of 1,2,3-trimethylindene (37)

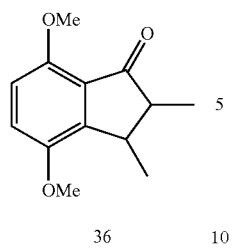

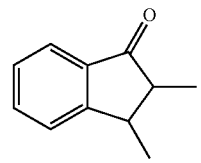

AlCl$_3$ (64 g, 0.48 mol) and CH$_2$Cl$_2$ (250 ml) (dried with magnesium sulfate) were placed under an argon atmosphere in a 500 ml three necked round bottomed flask fitted with a magnetic stirring apparatus, an addition funnel, an inner thermometer and a reflux condenser. A mixture of tigloyl chloride (33) (42 g, 0.35 mol) and 1,4-dimethoxybenzene (48.4 g, 0.35 mol, dissolved in CH$_2$Cl$_2$ (75 ml)) was added over a period of 1 h at −10° C. under vigorous stirring. After 2 h stirring at −2° C. to −5° C. the mixture was allowed to come to ambient temperature and was stirred overnight. The dark red mixture was then refluxed for 2 h, after cooling to ambient temperature the reaction mixture was poured carefully onto a mixture of concentrated HCl (300 ml) and ice (500 g). Then the resulting yellow mixture was transferred to a separation funnel, the lower CH$_2$Cl$_2$ layer was isolated and the aqueous layer extracted with diethyl ether (3×100 ml). The combined organic layers were dried over magnesium sulfate, filtered, and the solvents removed under reduced pressure to give a dark brown liquid. This residue was distilled using a 15 cm Vigreux column to obtain an orange-yellow light viscous liquid (110-115° C., 0.8 mbar). The liquid was purified via column chromatography [(SiO$_2$, 25×9 cm) eluent: cyclohexane:ethylacetate (1:1)] to afford 2,3-dimethyl-4,7-dimethoxy-1-indanone (36) (9.53 g, 12%), R$_f$ 0.35 (cyclohexane:ethylacetate (5:1)) as an orange liquid. The liquid was found to be a mixture of the two isomers of 4,7-dimethoxy-2,3-dimethyl-1-indanone (36a to 36b approximately 4:1).

$^1$H NMR: (500 MHz, CDCl$_3$): 36a δ [ppm] 7.01 (d, $^3$J=8.0 Hz, 1H, arom), 6.74 (d, $^3$J=8.5 Hz, 1H, arom), 3.89 (s, 3H, O—CH$_3$), 3.84 (s, 3H, O—CH$_3$), 2.97 (qd, $^3$J=7.0 Hz, $^3$J=3.0 Hz, 1H, CH-position 2), 2.22 (qd, $^3$J=7.5 Hz, $^3$J=3.0 Hz, 1H, CH-position 3), 1.40 (d, $^3$J=7.0 Hz, 3H, CHCH$_3$), 1.26 (d, $^3$J=7.5 Hz, 3H, CHCH$_3$); 36b δ [ppm] 6.99 (d, $^3$J=9.0 Hz, $^1$H, arom), 6.72 (d, $^3$J=7.5 Hz, 1H, arom), 3.89 (s, 3H, O—CH$_3$), 3.86 (s, 3H, O—CH$_3$), 3.53 (pseudoquintet, $^3$J=7.5 Hz, 1H, CH-position 2), 2.74 (qui, $^3$J=7.5 Hz, 1H, CH-position 3), 1.20 (d, $^3$J=7.0 Hz, 3H, CHCH$_3$-position 2) 1.16 (d, $^3$J=7.0 Hz, 3H, CHCH$_3$-position 3); $^{13}$C{$^1$H} (125.77 MHz, CDCl$_3$): δ [ppm] 36a 207.2, 151.8, 150.9, 148.2, 124.8, 117.5, 109.8, 56.0, 55.8, 51.6, 39.8, 19.5, 16.2; 36b 206.5, 151.5, 150.3, 149.3, 124.8, 116.9, 109.7, 56.0, 55.8, 47.1, 34.5, 16.1, 14.2; HRMS: Calcd.: 220.1099, found: 220.10909.

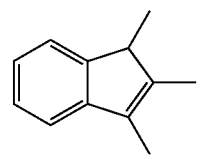

In a 1 liter three necked round bottomed flask fitted with a magnetic stirring apparatus and a reflux condenser 2,3-dimethyl-1-indanone (34) (19.2 g, 0.12 mol) was dissolved in dry diethyl ether (300 ml) under an argon atmosphere. Methyllithium (46.3 ml, 3 M solution in diethoxymethane, 0.14 mol) was added dropwise via a syringe and the mixture was refluxed overnight. The mixture was cooled to 0° C. and a solution of saturated ammonium chloride (100 ml) was added dropwise through the top of the condenser. The mixture was transferred into a separation funnel, the organic layer was washed with water (3×100 ml), dried over magnesium sulfate and filtered. The ether was removed under reduced pressure to afford the raw 1,2,3-trimethyl-1-indanol (19.34 g, 92%) as a yellow liquid which was used for the next step without further purification. Toluene (300 ml) was added to the raw 1,2,3-trimethyl-1-indanol (19.34 g, 0.11 mol) and the solution was transferred into a 500 ml round bottomed flask fitted with a Dean-Stark trap and a magnetic stirring apparatus. p-Toluene sulfonic acid (50 mg, 0.26 mmol) was added and the solution refluxed overnight. After completion of the removal of the water the excess toluene was removed via distillation through the Dean-Stark arm, the residue was cooled to ambient temperature, diluted with diethyl ether (100 ml), washed with a saturated solution of sodium bicarbonate (3×100 ml), dried over magnesium sulfate and filtered. After removal of the solvent in vacuo, the liquid was purified via column-chromatography [(SiO$_2$, 50×9 cm) eluent: cyclohexane:ethylacetate (10:1)] to afford two fractions: 1,2,3-Trimethylindene (37) (8.92 g, 51%) as a pale yellow liquid R$_f$ 0.41; (34) (7.94 g, 45%) (starting material) was obtained as a dark yellow liquid.

$^1$H NMR: (500 MHz, CDCl$_3$): δ [ppm] 7.34-7.10 (m, 4H, arom), 3.17 (q, $^3$J=7.5 Hz, 1H, H-position 1), 2.01 (q, $^5$J=1.0 Hz, 3H, CH$_3$-position 2), 1.97 (q, $^5$J=1.0 Hz, 3H, CH$_3$-position 3), 1.26 (d, $^3$J=7.5 Hz, 3H, CH$_3$-position 1); $^{13}$C{$^1$H}

NMR (125.77 MHz, CDCl$_3$) δ [ppm] 148.6, 146.6, 143.5, 131.4, 126.7, 124.2, 122.5, 118.3, 47.3, 16.1, 12.3, 10.5.

Synthesis of 1,2,3,4,7-pentamethylindene (38)

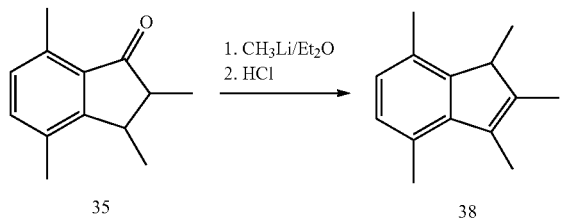

In a 1 liter three necked round bottomed flask fitted with a magnetic stirring apparatus and a reflux condenser 2,3,4,7-tetramethyl-1-indanone (35) (19.52 g, 0.1 mol) was dissolved in dry diethyl ether (300 ml) under an argon atmosphere. The mixture was cooled with ice and methyllithium (45 ml, 3 M solution in diethoxymethane, 0.135 mol) was added dropwise via a syringe, then the mixture was refluxed for 3 h. When the yellow reaction mixture had cooled a mixture of concentrated HCl (20 ml) and H$_2$O (60 ml) was added via an addition funnel. The resulting mixture was transferred to a separation funnel and extracted with diethyl ether (3×200 ml). The combined organic layers were stirred overnight with 15 ml concentrated HCl. After this time the reaction mixture was carefully adjusted to pH 7 with a saturated aqueous solution of sodium carbonate. The reaction mixture was transferred into a separation funnel. The organic layer was washed with H$_2$O (3×100 ml), dried over MgSO$_4$, filtered and the solvent removed under reduced pressure to give a yellow liquid. This residue was purified via column-chromatography [(SiO$_2$, 25×9 cm) eluent: cyclohexane] to afford 1,2,3,4,7-pentamethylindene (38) (8.35 g, 44%) as a yellow liquid; then (35) (starting material) (9.60 g, 49%) (eluent: cyclohexane:ethylacetate (10:1)) as a yellow liquid.

$^1$H NMR: (500 MHz, CDCl$_3$): δ [ppm] 6.88 (d, $^3$J=7.5 Hz, 1H, arom), 6.78 (d, $^3$J=8.0 Hz, 1H, arom), 3.15 (q, $^3$J=7.5 Hz, 1H, CH), 2.54 (s, 3H, benzylic CH$_3$), 2.35 (s, 3H, benzylic CH$_3$), 2.19 (q, $^5$J=1.0 Hz, 3H, CH$_3$-position 2), 1.94 (q, $^5$J=1.0 Hz, 3H, CH$_3$-position 3) 1.23 (d, $^3$J=7.5 Hz, 3H, CHCH$_3$); $^{13}$C{H$_1$} NMR (125.77 MHz, CDCl$_3$) δ [ppm] 146.8, 143.3, 143.2, 132.1, 129.9, 129.6, 127.5, 125.6, 46.3, 20.0, 18.6, 14.7, 14.1, 12.0.

Synthesis of 4,7-dimethoxy-1,2,3-trimethylindene (39)

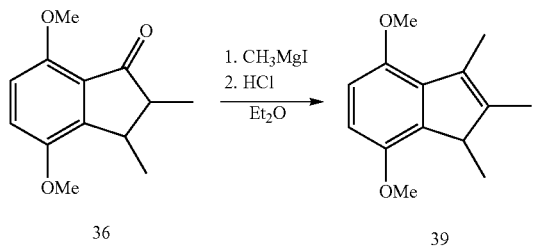 [SMILES: "Et2O" ; COc1ccc(OC)c2c1C(=O)C(C)C2C ; COc1ccc(OC)c2c1C(C)=C(C)C2C]

Diethyl ether (100 ml) and magnesium turnings (0.96 g, 39 mmol) were placed in a 250 ml three necked round bottomed flask fitted with a magnetic stirring apparatus and a reflux condenser. Under an argon atmosphere a solution of CH$_3$I (2.66 ml, 43 mmol) in degassed and dried diethyl ether (50 ml) was added via an addition funnel. The resulting grey solution was stirred for 45 min before addition of dry light petroleum (b.p. 80-110° C.) (20 ml). The ether was then removed under reduce pressure to yield a grey suspension. The resulting mixture was cooled with ice and a solution of 2,3-dimethyl-4,7-dimethoxy-1-indanone (36) (7 g, 32 mmol) in pentane (50 ml) was added dropwise over a period of 40 min, then the mixture was refluxed for 3 h. Then the yellow reaction mixture was cooled to 0° C. and a mixture of HCl (10 ml) and H$_2$O (40 ml) was added via an addition funnel. The resulting solution was transferred into a separation funnel and extracted with diethyl ether (3×50 ml). The combined organic layers were then washed with 0.25 M aqueous sodium thiosulfate (3×30 ml). The organic layers were filtered into a round bottomed flask, 15 ml concentrated HCl were added and the mixture was stirred at ambient temperature overnight. Then pH 7 was adjusted by addition of a saturated aqueous solution of sodium carbonate. The mixture was transferred into a separation funnel. The organic layer was washed with water (3×100 ml), dried over MgSO$_4$, filtered and the solvent removed under reduced pressure.

The residual liquid was purified via column chromatography [(SiO$_2$, 35×9 cm), initial eluent: cyclohexane:ethylacetate (100:2))] to afford two fractions: 1,2,3-trimethyl-4,7-dimethoxyindene (39) (4.63 g, 66%) as a yellow liquid R$_f$ 0.42; (Change of eluents to cyclohexane:ethylacetate (2:1)): 4,7-dimethoxy-2,3-dimethyl-1-indanone (36) (starting material) R$_f$ 0.35 (cyclohexane:ethylacetate) (5:1)) as a pale yellow liquid.

$^1$H NMR: (500 MHz, CDCl$_3$): δ [ppm] 6.70 (d, $^3$J=8.5 Hz, 1H, arom), 6.56 (d, $^3$J=9 Hz, 1H, arom), 3.80 (s, 3H, O—CH$_3$), 3.78 (s, 3H, O—CH$_3$) 3.23 (q, $^3$J=7.5 Hz, 1H, CH), 2.17 (s, 3H, CH$_3$), 1.90 (s, 3H, CH$_3$) 1.23 (d, $^3$J=7 Hz, 3H, CHCH$_3$); $^{13}$C{$^1$H} NMR (125.77 MHz, CDCl$_3$) δ [ppm] 150.6, 149.1, 142.9, 137.2, 135.7, 131.1, 111.1, 107.5, 56.7, 56.0, 46.4, 14.7, 13.4, 12.0. HRMS: Calcd.: 218.1306, found: 218.13110.

III. Preparation of Indenyl Phosphonium Salts

Synthesis of 1,2,3-trimethylindenyl-dicyclohexyl-phosphonium-trifluoroborate (16a)

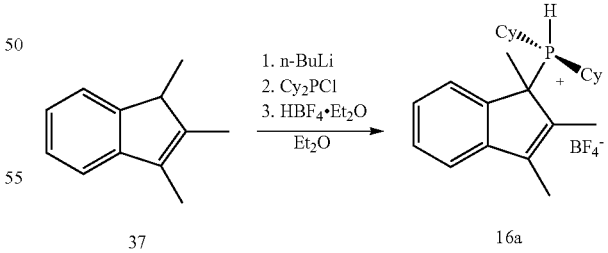

In a 100 ml Schlenk 1,2,3-trimethylindene (37) (2.44 g, 15.4 mmol) was dissolved in Et$_2$O (50 ml) under an argon atmosphere. The mixture was cooled to −60° C. (N$_2$/Isopropanol) and n-BuLi (5.9 ml, 2.5 M solution in hexane, 14.7 mmol) was added. The solution was stirred for 10 min at −60° C., then for 3 hours at ambient temperature. A white precipitate was formed. Then the mixture was cooled to −60° C. and Cy$_2$PCl (2.7 ml, 12 mmol) was added. The mixture was allowed to come to room temperature, stirred for additional 2 h and the formed LiCl was removed by filtration over a pad of Celite® under Schlenk conditions. The resulting slightly yellowish filtrate was treated dropwise with HBF$_4$.Et$_2$O (2 ml, 14.9 mmol) to give a white precipitate which was separated via filtration and dissolved in 10 ml acetonitrile. After filtration the clear filtrate was dropped into Et$_2$O (900 ml, vigorously stirred). The formed white precipitate was separated via suction filtration. Removal of the volatiles in vacuo afforded (16a) as a white solid (2.82 g, 53%).

$^1$H NMR: (500 MHz, CDCl$_3$): δ [ppm] 7.64 (d, $^3$J=7.5 Hz, 1H, arom), 7.48 (t, $^3$J=7.5 Hz, 1H, arom), 7.40-7.35 (m, 2H, arom), 6.36 (dt, $^1$J(P)=475 Hz, $^4$J=3.5 Hz, 1H, P—H), 2.34-2.26 (m, 1H, —CH), 2.16 (d, $^4$J(P)=4.0 Hz, 3H, CH$_3$-position 2), 2.14 (s, 3H, CH$_3$-position 3), 2.09-1.14 (m, 21H, CH$_2$ and —CH), 1.81 (d, $^3$J(P)=17.5 Hz, 3H, CH$_3$-position 1);

$^{13}$C{$^1$H} (125.77 MHz, CDCl$_3$): δ [ppm] 145.2, 141.8, 138.8 (d, J=7.8), 137.8 (d, J=2.9 Hz), 129.8, 126.7, 123.4, 120.0, 51.6 (d, J=32.2 Hz), 31.0, 30.7 (d, J=10.8 Hz), 30.5, 29.8 (d, J=3 Hz), 29.0 (d, J=3.5 Hz), 28.2 (d, J=3.3 Hz), 28.1 (d, J=3.1 Hz), 26.9 (d, J=6.0 Hz), 26.8 (d, J=5.8 Hz), 26.6, 26.5, 24.9 (d, J=3.8 Hz), 19.6, 11.2, 10.7; $^{31}$P {$^1$H} (202.46 MHz, CDCl$_3$): δ [ppm] 29.2; $^{31}$P (202.46 MHz, CDCl$_3$): δ [ppm] 29.2 (d, J=473.7 Hz).

Synthesis of 1,2,3-tetramethylindenyl-diisopropyl-phosphonium-trifluoroborate (17a)

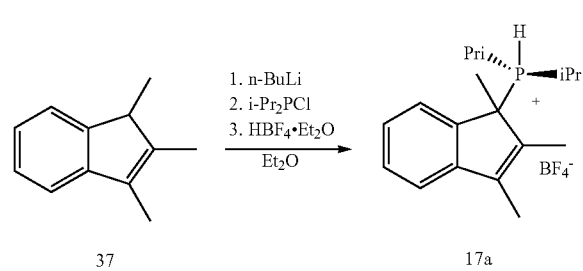

In a 250 ml Schlenk flask fitted with stirring apparatus 1,2,3-trimethylindene (37) (5.14 g, 32.5 mmol) was dissolved in Et$_2$O (100 ml) under an argon atmosphere. The mixture was cooled to −60° C. (N$_2$/Isopropanol) and n-BuLi (12.38 ml, 2.5M solution in hexane, 31 mmol) was added. The solution was stirred for 10 min at −60° C., then for 3 hours at ambient temperature. A white precipitate was formed. Then the mixture was cooled to −60° C. and iPr$_2$PCl (4.1 ml, 25.8 mmol) was added. The mixture was allowed to come to room temperature, stirred for additional 2 h and the formed LiCl was removed by filtration over a pad of Celite® under Schlenk conditions. The resulting slightly yellowish filtrate was treated dropwise with HBF$_4$.Et$_2$O (4.42 ml, 32 mmol) to give a white precipitate which was separated via filtration and dissolved in 10 ml acetonitrile. After filtration the clear filtrate was dropped into Et$_2$O (900 ml, vigorously stirred). The formed white precipitate was separated via suction filtration. Removal of the volatiles in vacuo afforded (17a) as a white solid (8.53 g, 91%)

$^1$H NMR: (500 MHz, CDCl$_3$): δ [ppm] 7.68 (d, $^3$J=8.0 Hz, 1H, arom), 7.48 (t, $^3$J=7.5 Hz, 1H, arom), 7.39-7.35 (m, $^2$H, arom), 6.44 (dt, $^1$J(P)=473, $^3$J=4.0 Hz, 1H, P—H), 2.69 (m, 1H, —CH), 2.41 (m, 1H, —CH), 2.16 (s, 3H, CH$_3$-position 3), 2.15 (d, $^3$J=3.5 Hz, 3H, CH$_3$-position 2), 1.81 (d, $^3$J(P)=17 Hz, 3H, CH$_3$-position 1), 1.44 (ddd, $^3$J(P)=96.0 Hz, $^3$J=18.5 Hz, $^3$J=7.5 Hz, 6H, CH$_3$) 1.13 (ddd, $^3$J(P)=91.0 Hz, $^3$J=18.0 Hz, J=7.0 Hz, 6H, CH$_3$); $^{13}$C{$^1$H} (125.77 MHz, CDCl$_3$): δ [ppm] 145.1 (d, J=3.8 Hz), 141.6, 138.9 (d, J=8.0 Hz), 137.7 (d, J=3.8 Hz), 129.8, 126.7, 123.5 (d, J=3.5 Hz), 120.2, 51.5 (d, J=32.6 Hz), 21.1 (d, J=6.7 Hz), 20.8 (d, J=5.6 Hz), 19.9 (d, J=11.5 Hz), 19.1 (d, J=2.1 Hz), 18.2 (d, J=2.3 Hz), 17.7 (d, J=2.3 Hz), 11.1, 10.8; $^{31}$P {$^1$H} (202.46 MHz, CDCl$_3$): δ [ppm] 36.6; $^{31}$P (202.46 MHz, CDCl$_3$): δ [ppm] 36.6 (d, J=472.9 Hz).

Synthesis of 1,2,3,4,7-pentamethylindenyl-diisopropyl-phosphonium-trifluoroborate (19a)

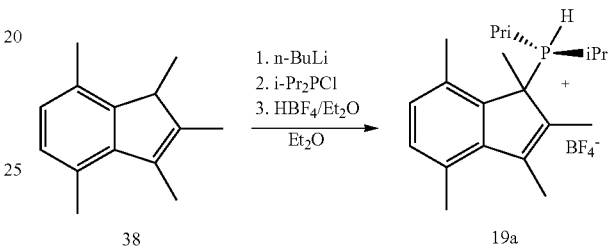

In a 100 ml Schlenk flask 1,2,3,4,7-pentamethylindene (38) (3.0 g, 16 mmol) was dissolved in Et$_2$O (50 ml) under an argon atmosphere. The mixture was cooled to −60° C. (N$_2$/Isopropanol) and n-BuLi (16.1 ml, 2.5M solution in hexane, 15 mmol) was added. The solution was stirred for 10 min at −60° C., then for 3 hours at ambient temperature. A white precipitate was formed. The mixture was cooled to −60° C. and iPr$_2$PCl (2.0 ml, 12.8 mmol) was added. The mixture was allowed to come to room temperature, stirred for additional 2 h and the formed LiCl was removed by filtration over a pad of Celite® under Schlenk conditions. The resulting slightly yellowish filtrate was treated dropwise with HBF$_4$.Et$_2$O (2.2 ml, 16 mmol) to give a white precipitate separated via filtration and dissolved in 10 ml chloroform. After filtration the clear filtrate was dropped into Et$_2$O (900 ml, vigorously stirred). The formed white precipitate was separated via suction filtration. Removal of the volatiles in vacuo afforded (19a) as a white solid (4.23 g, 84%). $^1$H NMR: (500 MHz, CDCl$_3$): δ [ppm] 7.09 (d, $^3$J=8.0 Hz, 1H, arom), 6.97 (d, $^3$J=8.0 Hz, 1H, arom) 6.41 (dq, $^1$J(P)=468 Hz, $^3$J=5.3 Hz, 1H, P—H), 2.84-2.75 (m, 1H, —CH), 2.59 (s, 3H, —CH$_3$ benzylic), 2.58 (s, 3H, —CH$_3$ benzylic), 2.31 (d, $^4$J=4.5 Hz, 3H, CH$_3$-position 2), 2.23-2.14 (m, 1H, —CH), 2.13 (s, 3H, CH$_3$-position 3), 1.89 (d, $^3$J(P)=17 Hz, 3H, CH$_3$-position 1), 1.50 (ddd, $^3$J(P)= 107 Hz, $^3$J=18.5 Hz, J=7.0 Hz, 6H, CH$_3$) 1.12 (ddd, $^3$J(P)= 96.5 Hz, $^3$J=18.5 Hz, J=7.0 Hz, 6H, CH$_3$); $^{13}$C{$^1$H} (125.77 MHz, CDCl$_3$): δ [ppm] 143.3, 141.4 (d, J=9.2 Hz), 140.6, 136.2 (d, J=6.3 Hz), 133.6, 132.2 (d, J=2.1 Hz), 130.2, 130.0, 52.9 (d, J=29.2 Hz), 22.1 (d, J=3.6 Hz), 21.8, 20.6, 20.4 (d, J=2.3 Hz), 20.2, 19.1 (d, J=1.8 Hz), 18.9 (d, J=1.9 Hz), 18.7 (d, J=1.8 Hz), 18.1 (d, J=3.1 Hz), 15.2, 12.3; $^{31}$P{$^1$H} (202.46 MHz, CDCl$_3$): δ [ppm] 34.0; $^{31}$P (202.46 MHz, CDCl$_3$): δ [ppm] 34.0 (d, J=463 Hz).

Synthesis of 1,2,3,4,7-pentamethylindenyl-dicyclohexyl-phosphonium-trifluoroborate (18a)

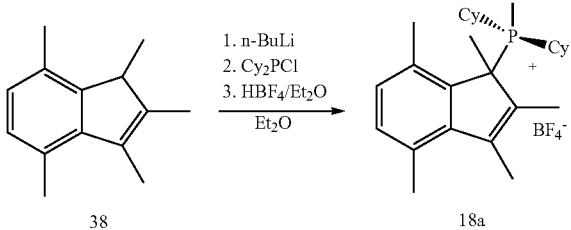

In a 100 ml Schlenk flask 1,2,3,4,7-pentamethylindene (38) (3.0 g, 16 mmol) was dissolved in Et$_2$O (50 ml) under an argon atmosphere. The mixture was cooled to −60° C. (N$_2$/Isopropanol) and n-BuLi (6.1 ml, 2.5 M solution in hexane, 15 mmol) was added. The solution was stirred for 10 min at −60° C., then for 3 hours at ambient temperature. A white precipitate was formed. Then the mixture was cooled to −60° C. and Cy$_2$PCl (2.8 ml, 12.7 mmol) was added. The mixture was allowed to come to room temperature, stirred for additional 2 h at ambient temperature and the formed LiCl was removed by filtration over a pad of Celite® under Schlenk conditions. The resulting slightly yellowish filtrate was treated dropwise with HBF$_4$.Et$_2$O (2.2 ml, 16 mmol) to give a white precipitate which was separated via filtration and dissolved in 10 ml chloroform. After filtration the clear filtrate was dropped into Et$_2$O (700 ml, vigorously stirred). The formed white precipitate was separated via suction filtration. Removal of the volatiles in vacuo afforded (18a) as a white solid (4.12 g, 69%).

$^1$H NMR: (500 MHz, CDCl$_3$): δ [ppm] 7.10 (d, $^3$J=8.0 Hz, 1H, arom), 6.97 (d, $^3$J=8.0 Hz, 1H, arom), 6.30 (dq, $^1$J(P)=470 Hz, J=3.5 Hz, 1H, P—H), 2.58 (s, 3H, —CH$_3$ benzylic), 2.58 (s, 3H, —CH$_3$ benzylic), 2.46-2.39 (m, 1H, —CH), 2.31 (d, $^4$J(P)=4.5 Hz, 3H, CH$_3$-position 2), 2.11 (s, 3H, CH$_3$-position 3), 1.89 (d, $^3$J(P)=16.5 Hz, 3H, CH$_3$-position 1), 1.86-0.93 (m, 21H, —CM and —CH); $^{13}$C{$^1$H} (125.77 MHz, CDCl$_3$): δ [ppm] 143.0, 140.9 (d, J=9.3), 140.3, 136.0 (d, J=4.9 Hz), 133.1, 131.9 (d, J=4.0), 129.7, 129.6, 52.8 (d, J=29.2 Hz), 31.5 (d, J=7.2 Hz), 31.2, 29.6 (d, J=3.5 Hz), 29.1 (d, J=3.3 Hz), 28.2 (d, J=3.5 Hz), 27.9 (d, J=3.8 Hz), 27.0 (d, J=11.9 Hz), 26.8, 26.7, 26.6 (d, J=13.1), 25.0, 24.8, 20.2, 19.8, 18.1, 14.8, 11.9; $^{31}$P {$^1$H} (202.46 MHz, CDCl$_3$): δ [ppm] 25.5; $^{31}$P (202.46 MHz, CDCl$_3$): δ [ppm] 25.5 (d, J=472.3 Hz).

Synthesis of 4,7-dimethoxy-1,2,3-trimethylindenyl-dicyclohexyl-phosphonium-trifluoroborate (20a)

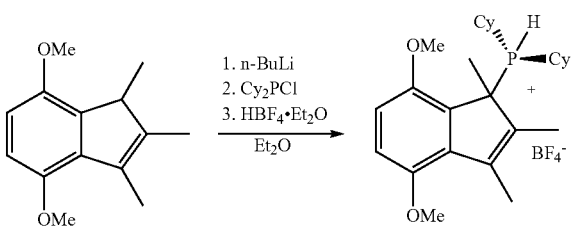

In a 100 ml Schlenk flask 4,7-dimethoxy-1,2,3-trimethylindene (39) (1.7 g, 7.79 mmol) was dissolved in Et$_2$O (50 ml) under an argon atmosphere. The mixture was cooled to −60° C. (N$_2$/Isopropanol) and n-BuLi (3 ml, 2.5 M solution in hexane, 7.43 mmol) was added. A white precipitate was formed. The solution was stirred for 10 min at −60° C., stirred for 3 hours at ambient temperature. Then the mixture was cooled to −60° C. and Cy$_2$PCl (1.3 ml, 6.19 mmol) was added. The mixture was allowed to come to room temperature, then for additional 2 h at ambient temperature and the formed LiCl was removed by filtration over a pad of Celite® under Schlenk-conditions. The resulting slightly yellowish filtrate was treated dropwise with HBF4.Et$_2$O (1 ml, 7.79 mmol) to give a white precipitate which was separated via filtration and dissolved in 10 ml chloroform. After filtration the clear filtrate was dropped into Et$_2$O (700 ml, vigorously stirred). The formed white precipitate was separated via suction filtration. Removal of the volatiles in vacuo afforded (20a) as a white solid (1.72 g, 55%).

$^1$H NMR: (500 MHz, CDCl3): δ [ppm] 6.93 (dd, $^3$J=9.0 Hz J=1.5 Hz, 1H, arom), 6.77 (d, $^3$J=9.0 Hz, 1H, arom), 6.24 (ddd, $^1$J(P)=472.5, $^3$J=5.5 Hz, J=2.5 Hz, 1H, P—H), 3.92 (s, 3H, O—CH$_3$), 3.84 (s, 3H, O—CH$_3$), 2.60-2.49 (m, 1H, —CH), 2.28 (dd, $^4$J(P)=4.0 Hz, J=1.0 Hz, 3H, —CH$_3$-position 2), 2.18-2.11 (m, 1H, —CH), 2.06 (s, 3H, —CH$_3$-position 3), 1.76 (d, $^3$J(P)=16.5 Hz, 3H, CH$_3$-position 1), 2.04-1.01 (m, 20H, —CH$_2$); $^{13}$C{$^1$H} (125.77 MHz, CDCl3): δ [ppm] 149.7 (d, J=1.9 Hz), 149.5, 138.9 (d, J=7.0), 136.9 (d, J=3.0 Hz), 134.2 (d, J=2.8), 129.7, 113.8, 109.1, 56.3, 55.7, 51.6 (d, J=32.2 Hz), 32.3, 32.0, 30.6, 30.3, 29.3 (d, J=3.3 Hz), 29.2 (d, J=5.3 Hz), 28.2 (d, J=3.3 Hz), 27.7 (d, J=3.1 Hz), 27.0 (d, J=13.1 Hz), 26.9 (d, J=14.2 Hz), 25.1, 24.9, 17.8, 13.6, 10.7; $^{31}$P{$^1$H} (202.46 MHz, CDCl3): δ [ppm] 25.4; $^{31}$P (202.46 MHz, CDCl3): δ [ppm] 25.4 (d, J=471.1 Hz).

Synthesis of 4,7-dimethoxy-1,2,3-trimethylindenyl-diisopropyl-phosphonium-trifluoroborate (21a)

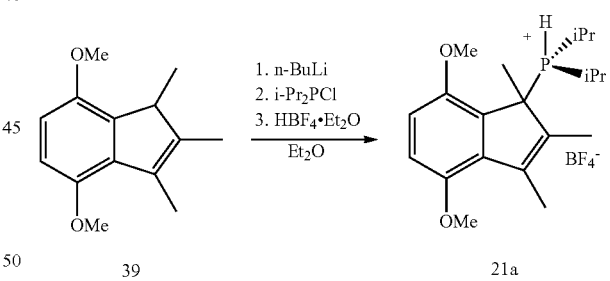

In a 100 ml Schlenk flask 4,7-dimethoxy-1,2,3-trimethylindene (39) (1.7 g, 7.79 mmol) was dissolved in Et$_2$O (50 ml) under an argon atmosphere. The mixture was cooled to −60° C. (N$_2$/isopropanol) and n-BuLi (3 ml, 2.5 M solution in hexane, 7.43 mmol) was added. The solution was stirred for 10 min at −60° C., then for 3 hours at ambient temperature. A white precipitate was formed. Then the mixture was cooled to −60° C. and iPr$_2$PCl (1 ml, 6.24 mmol) was added. The mixture was allowed to come to room temperature, stirred for additional 2 h at ambient temperature and the formed LiCl was removed by filtration over a pad of Celite® under Schlenk conditions. The resulting slightly yellowish filtrate was treated dropwise with HBF$_4$-Et$_2$O (1 ml, 7.72 mmol) to give a white precipitate which was separated via filtration and dissolved in 10 ml chloroform. After filtration the clear filtrate was dropped into Et$_2$O (700 ml, vigorously stirred). The formed white precipitate was separated via suction filtration. Removal of the volatiles in vacuo afforded (21a) as a white solid (1.73 g, 66%).

$^1$H NMR: (500 MHz, CD$_3$CN): δ [ppm] 7.13 (dd, $^3$J=9.0 Hz, J=1.5 Hz, 1H, arom), 6.99 (d, $^3$J=9.0 Hz, 1H, arom), 6.39 (dq, $^1$J(P)=465.5 Hz, $^3$J=3.0 Hz, 1H, P—H), 3.99 (s, 3H, O—CH$_3$), 3.87 (s, 3H, O—CH$_3$), 3.10-3.00 (m, 1H, —CH), 2.62-2.51 (m, 1H, CH), 2.30 (dd, $^4$J(P)=5.0 Hz, J=1.0 Hz, 3H, —CH$_3$-position 2), 2.13 (s, 3H, —CH$_3$-position 3), 1.86 (d, $^3$J(P)=16.5 Hz, 3H, CH$_3$-position 1), 1.45 (ddd, $^3$J(P)=100 Hz, $^3$J=19 Hz, $^3$J=7.0 Hz, 6H, CH$_3$), 1.18 (ddd, $^3$J(P)=72.5 Hz, $^3$J=17.5 Hz, $^3$J=7 Hz, 6H, CH$_3$); $^{13}$C{$^1$H} (125.77 MHz, CD$_3$CN): δ [ppm] 150.8 (d, J=2.1 Hz), 150.4, 139.7 (d, J=9.0 Hz), 137.6 (d, J=3.4 Hz), 134.7 (d, J=3.5 Hz), 130.5, 115.0, 110.5, 56.6, 56.1, 52.4 (d, J=31.8 Hz), 23.4 (d, J=35.8 Hz), 21.3 (d, J=39.5 Hz), 19.9 (d, J=2.64 Hz), 19.5 (d, J=1.9 Hz), 19.0 (d, J=2.9 Hz), 18.3 (d, J=2.0 Hz), 17.7 (d, J=2.3 Hz), 13.8, 10.8; $^{31}$P {$^1$H} (202.46 MHz, benzene d$_6$): δ [ppm] 33.0; $^{31}$P (202.46 MHz, benzene d$_6$): δ [ppm] 33.0 (d, J=464.8 Hz).

IV. Preparation of Fluorenyl Derivatives (i) Preparation of 9-Substituted Fluorenes General procedure for the synthesis of 9-substituted fluorenes:

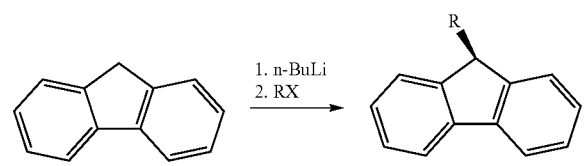

To a solution of fluorene (30 mmol) in THF (60 ml), abs, 40 mmol of n-BuLi (2.5 M in hexane) were added at –60° C. The solution immediately turned brownish and was stirred for 1.5 h at room temperature. After cooling to –60° C. again, the reaction mixture was quenched with alkylhalide RX (45 mmol, 1.5 equiv.), stirred for 10 min at –60° C., then additional 2 h at room temperate. 100 ml water were added to the reaction mixture which was then extracted with diethylether (3×100 ml). The combined organic phases were subsequently washed with an aqueous solution of Na$_2$S$_2$O$_3$, brine and dried over MgSO$_4$. After filtration and removal of the volatiles under vacuum the crude product was purified via filtration on a short silica gel pad (5 cm, eluent: cyclohexane) and concentrated under vacuum resulting in the pure 9-substituted fluorenes typically in near quantitative yield.

The following 9-substituted fluorenes were prepared according to the above general procedure:

9-Methylfluorene (40)

Fluorene (15.0 g, 90.4 mmol), n-BuLi (48.1 ml, 120 mmol, 2.5 M in hexane), RX=iodomethane (19.3 g, 136 mmol). 40 was isolated as a yellowish waxy solid (16.2 g, quant.). The analytical data were identical to those in the literature (M. A. Schmidt, H. G. Alt, W. Milius, J. Organomet. Chem. 1996, 525, 15).

$^1$H NMR (500 MHz, CDCl$_3$) δ [ppm] 7.74 (d, $^3$J=7.5 Hz, 2H, ar), 7.49-7.48 (m, 2H, ar), 7.34-7.28 (m, 4H, ar), 3.92 (q, $^3$J=7.5 Hz, 1H, 9HFlu), 1.50 (d, $^3$J=5.5 Hz, $^3$J=7.5 Hz, 3H, CH$_3$); $^{13}$C{$^1$H} NMR (125.77 MHz, CDCl$_3$) δ [ppm] 149.4, 141.0, 127.4 (2×), 124.5, 120.3, 42.9, 18.6.

9-Ethylfluorene (41)

Fluorene (5.0 g, 30.1 mmol), n-BuLi (16 ml, 40 mmol, 2.5 M in hexane), RX=iodoethane (7.04 g, 45.1 mmol). 41 was isolated as yellow oil (5.7 g, 97%).

Analytical data were identical to those in the literature (K. D. Bartle, P. M. G. Bavin, D. W. Jones, R. L'Amie, Tetrahedron 1970, 26, 911).

$^1$H NMR (500 MHz, CDCl$_3$) δ [ppm] 7.73 (d, $^3$J=10.0 Hz, 2H, ar), 7.50-7.48 (m, 2H, ar), 7.36-7.27 (m, 4H, ar), 3.94 (t, $^3$J=6.0 Hz, 1H, 9HFlu), 2.07 (dq, $^3$J=5.5 Hz, $^3$J=7.0 Hz, 2H, CH$_2$), 0.71 (t, $^3$J=7.5 Hz 3H, CH$_3$); $^{13}$C{$^1$H} NMR (125.77 MHz, CDCl$_3$) δ [ppm] 147.2, 141.3, 126.8, 126.7, 124.3, 119.7, 48.5, 25.7, 9.7.

9-Isopropylfluorene (42)

Fluorene (15.0 g, 90.4 mmol), n-BuLi (48.1 ml, 120 mmol, 2.5 M in hexane), RX=2-iodopropane (14.0 ml, 139.6 mmol). 42 was isolated as a yellowish solid (18.7 g, quant.). The analytical data were identical with these to be found in the literature (M. A. Schmidt, H. G. Alt, W. Milius, J. Organomet. Chem. 1996, 525, 15).

$^1$H NMR (500 MHz, CDCl$_3$) δ [ppm] 7.73 (d, $^3$J=7.5 Hz, 2H, ar), 7.52-7.51 (m, 2H, ar), 7.37-7.25 (m, 4H, ar), 3.91 (d, $^3$J=3.0 Hz, 1H, 9HFlu), 2.59-2.52 (m, 1H, CH), 0.84 (d, $^3$J=7.0 Hz 6H, CH$_3$); $^{13}$C{$^1$H} NMR (125.77 MHz, CDCl$_3$) δ [ppm] 146.7, 142.1, 127.3, 127.1, 125.2, 120.0, 54.2, 32.6, 19.5 (CH$_3$, 2×).

9-n-Propylfluorene (43)

Fluorene (15.0 g, 90.4 mmol), n-BuLi (48.1 ml, 120 mmol, 2.5 M in hexane), RX=1-iodopropane (20.8 g, 122.3 mmol). 43 was isolated as a yellowish solid (18.6 g, quant.). The analytical data were identical to those found in the literature (A. Mathieu, Bull. Soc. Chim. Fr. 1971, 1526).

$^1$H NMR (500 MHz, CDCl$_3$) δ [ppm] 7.73 (d, $^3$J=7.0 Hz, 2H, ar), 7.51-7.49 (m, 2H, ar), 7.36-7.27 (m, 4H, ar), 3.97 (t, $^3$J=6.0 Hz, 1H, 9HFlu), 1.99-1.94 (m, 2H, CH$_2$), 1.27-1.19 (m, 2H, CH$_2$), 0.86 (t, $^3$J=7.5 Hz 3H, CH$_3$); $^{13}$C{$^1$H} NMR (125.77 MHz, CDCl$_3$) δ [ppm] 147.7, 141.1, 126.8, 126.7, 124.4, 119.8, 47.4, 35.4, 19.0, 14.4.

9-n-Octadecylfluorene (44)

Fluorene (7.0 g, 42.1 mmol), n-BuLi (17.35 ml, 43.4 mmol, 2.5 M in hexane), RX=1-bromooctadecane (14.53 g, 43.6 mmol). Following the usual workup 44 was isolated as a white solid (15.5 g, 88%), R$_f$ 0.73 (cyclohexane).

$^1$H NMR (300 MHz, CDCl$_3$) δ [ppm] 7.76-7.73 (m, 2H, ar), 7.52-7.49 (m, 2H, ar), 7.38-7.27 (m, 4H, ar), 3.96 (t, $^3$J=6.0 Hz, 1H, 9HFlu), 3.02-1.95 (m, 2H, CH$_2$), 1.31-1.14 (m, 32H, CH$_2$), 0.88 (t, $^3$J=6.6 Hz 3H, CH$_3$); $^{13}$C{$^1$H} NMR (75.42 MHz, CDCl$_3$) δ [ppm] 147.7, 141.1, 126.8, 126.7, 124.3, 119.8, 47.5, 33.1, 31.9, 30.0, 29.7 (CH$_2$, 7×), 29.6 (CH$_2$, 3×), 29.4, 29.3, 25.7, 22.7, 14.1.

9-Benzylfluorene (45)

Fluorene (19.0 g, 114 mmol), n-BuLi (54.9 ml, 137 mmol, 2.5 M in hexane), RX=benzylchloride (17.03 ml, 148 mmol). After the usual workup 45 was isolated and recrystallized from heptane to give a white solid (25.8 g, 88.4%). The analytical data were identical to these in the literature (E. H. Licht, H. G. Alt, M. M. Karim, J. Organomet. Chem. 2000, 599, 275).

$^1$H NMR (500 MHz, CDCl$_3$) δ [ppm] 7.72 (d, $^3$J=8 Hz, 2H, ar), 7.37-7.13 (m, 11H, ar), 3.10 (d, $^3$J=7.5 Hz); $^{13}$C{$^1$H} NMR (125.77 MHz, CDCl$_3$) δ [ppm] 146.8, 140.8, 139.8, 129.5, 128.3, 127.1, 126.6, 126.4, 124.8, 119.8, 48.7, 40.1.

(ii) Preparation of 1-methyl-9-ethyl-fluorene (48)

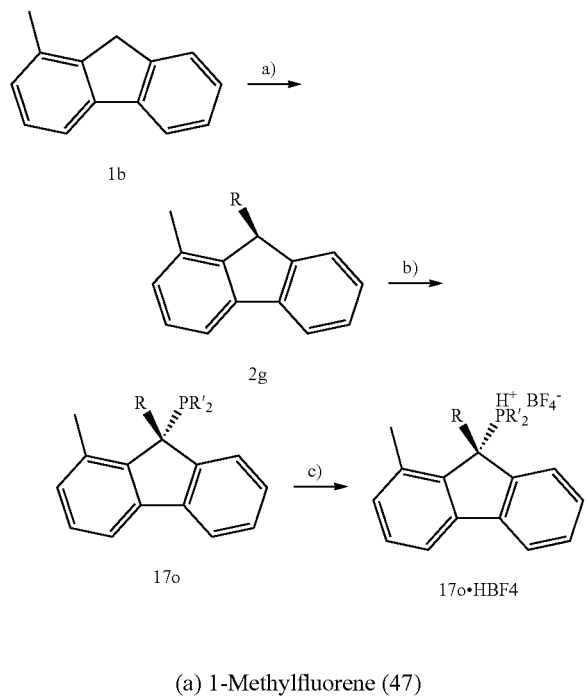

(a) 1-Methylfluorene (47)

1-Methylfluoren-9-one (46) was prepared according to Mortier et al. (D. Tilly, S. S. Samanta, A.-S. Castanet, A. De, J. Mortier, Eur. J. Org. Chem. 2005, 174). 1-Methylfluoren-9-one (46) was reduced according to the general procedure of Carruthers et al. (W. Carruthers, D. Whitmarsh, J. Chem. Soc. Perkin Trans, I 1973, 1511). 1-Methylfluoren-9-one (46) (6.8 g, 35 mmol) was dissolved in 450 ml propionic acid. Red phosphorus (7.4 g) and 100 ml concentrated HI were added and the reaction mixture was refluxed for 24 h. Quantitative conversion was shown by TLC. The reaction mixture was diluted with 500 ml water, neutralized with NaOH and extracted with Et$_2$O (4×125 ml). The combined organic layers were washed with brine (2×125 ml), dried over MgSO$_4$, filtered and the volatiles removed in vacuo to afford 6.1 g (97%) 47 as a white solid. The analytical data were consistent with the literature (G. L. Grunewald, A. E. Carter, D. J. Sall, J. A. Monn, J. Med. Chem. 1988, 31, 60 and M. J. Shapiro, J. Org. Chem. 1978, 43, 3769).

$^1$H NMR (500 MHz, acetone-d$_6$) δ [ppm] 7.82 (d, $^3$J=8.0 Hz 1H, ar), 7.67 (d, $^3$J=7.5 Hz 1H, ar), 7.58-7.56 (m, 1H, ar), 7.36-7.34 (m, 1H, ar), 7.30-7.26 (m, 2H, ar), 7.12-7.10 m, 1H, ar), 3.78 (s, 2H, 9HFlu), 2.39 (s, 3H, CH3); $^{13}$C{$^1$H} NMR (125.77 MHz, acetone-d$_6$) δ [ppm] 144.4, 143.3, 143.3, 142.5, 135.5, 128.9, 128.4, 127.9, 127.9, 126.3, 121.2, 118.6, 36.6, 19.2.

(b) 1-Methyl-9-ethyl-fluorene (48)

The substitution reaction at the 9-position was performed according to the general procedure for the synthesis of 9-substituted fluorenes described above in item IV(i). 1-Methylfluorene (47) (3.01 g, 16.7 mmol) was used instead of fluorene, n-BuLi (8.06 ml, 20 mmol, 2.5 M in hexane), RX=1-iodoethane (3.39 g, 21.7 mmol). 48 was isolated to give a colorless oil (3.33 g, 95%).

$^1$H NMR (500 MHz, acetone-d$_6$) δ [ppm] 7.79-7.77 (m, 1H, ar), 7.64 (d, $^3$J=7.5 Hz, 1H, ar), 7.55-7.53 (m, 1H, ar), 7.34-7.24 (m, 3H, ar), 7.10-7.08 (m, 1H, ar), 4.11 (t, $^3$J=4.5 Hz, 1H, 9HFlu), 2.46 (s, 3H, CH$_3$), 2.26-2.20 (m, 2H, CH$_2$), 0.35 (t, $^3$J=7.5 Hz 3H, CH$_3$); C{$^1$H} NMR (125.75 MHz, acetone-d$_6$) δ [ppm] 148.0, 145.4, 142.6, 142.4, 135.2, 129.4, 128.0, 127.7, 127.6, 124.9, 120.4, 118.1, 48.5, 24.3, 19.2, 8.3.

(iii) Preparation of 1,3,8-trimethyl-9-ethyl-fluorene (55)

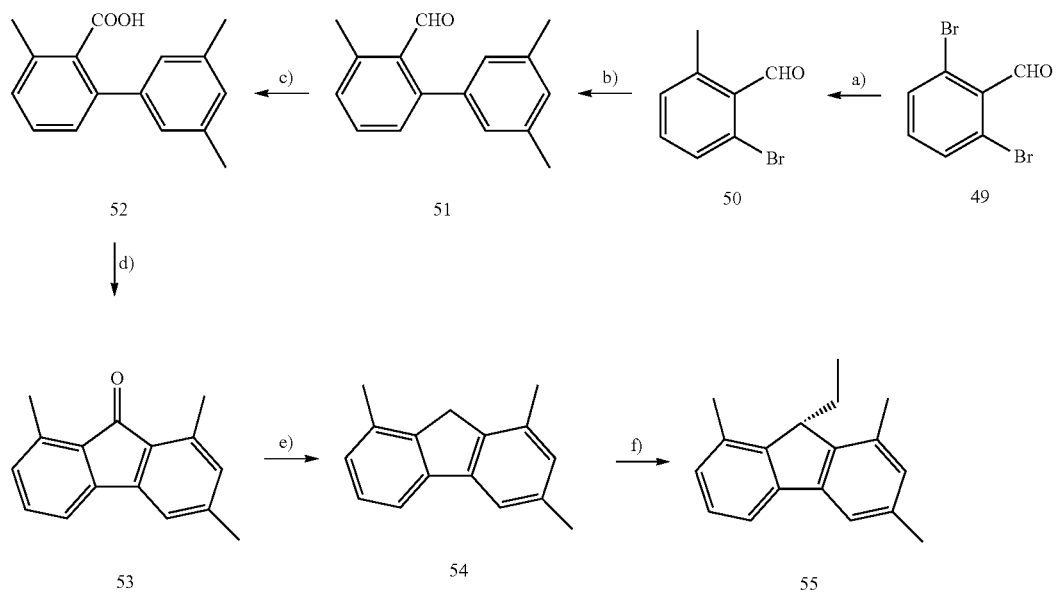

Reagents and conditions: a) 1,3-propanediol, $ZrCl_4$; n-BuLi, MeI, $H_2SO_4$;
b) $Pd(OAc)_2$, SIMES, $Cs_2CO_3$, 3,5-$Me_2$-$C_6H_3B(OH)_2$, dioxane; c $NaClO_2$, $H_2O_2$;
d) $H_2SO_4$; e) HI, $P_{red}$, propionic acid; f) n-BuLi, EtI, THF, −60° C.

(a) 2-Bromo-6-methyl-benzaldehyde (50)

Ortho-lithiation of 1,3-dibromobenzene using the protocol of Servatovski et al. (S. Lilinski. J. Servatowski, J. Org. Chem. 2003, 68, 5384) and subsequent quenching with DMF resulted in 2,6-dibromobenzaldehyde (49) which was protected as an acetal and treated with n-BuLi, followed by quenching the lithiated intermediate with methyliodide to yield the desired deprotected 2-bromo-6-methylbenzaldehyde (50) in nearly quantitative yields:

2,6-Dibromobenzaldehyde (49) (10.0 g, 37.9 mmol) was dissolved in 160 ml dry $CH_2Cl_2$. Propanediol (6.4 ml, 88.5 ml), triethylorthoformate (6.83 ml, 41 mmol) and anhydrous $ZrCl_4$ (1.0 g) were added at ambient temperature and stirred overnight. Then NaOH (50 ml of a 10% solution) was added and stirred for an additional hour. The organic phase was separated, the aqueous phase was extracted with $Et_2O$ (2×40 ml). The combined organic phases were washed with water (3×60 ml), dried over $MgSO_4$ and the volatiles were removed in vacuo to afford 12 g (98%) 2-(2,6-Dibromophenyl)-1,3-dioxane (acetal) as a slightly yellow solid.

$^1$H NMR (500 MHz, $CDCl_3$) δ [ppm] 7.55 (d, $^3J$=8.0 Hz 2H, ar), 7.00 (t, $^3J$=8.0 Hz 1H, ar), 6.19 (s, 1H, CH), 4.33-4.29 (m, 2H, $CH_2$), 4.02-3.97 (m, 2H, $CH_2$), 2.44-2.34 (m, 1H, $CH_2$), 1.44-1.40 (m, 1H, $CH_2$); $^{13}C\{^1H\}$ NMR (125.77 MHz, $CDCl_3$) δ [ppm] 133.9, 132.5, 129.8, 122.9, 101.6, 66.7, 24.1. The acetal (10.1 g, 31.25 mmol) was dissolved in THF, abs. (200 ml). At −78° C. n-BuLi (15.1 ml, 2.5 M in hexane, 37.8 mmol) was added within 25 min, followed by 90 min additional stirring at that temperature. Then the reaction mixture was treated with methyliodide (5.99 g, 42.2 mmol) and stirred for 25 min at −78° C. Next the reaction mixture was allowed to warm to ambient temperature within 1.5 h. The resulting solution was quenched with HCl (290 ml of a 5 N solution) and stirred for 1.5 h at ambient temperature. The complete deprotection of the aldehyde was checked via GC analysis. Then the reaction mixture was subsequently extracted with diethylether (4×100 ml), the combined organic layers were washed with a 10% solution of sodium thiosulfate (100 ml), water (100 ml), dried over $MgSO_4$, filtered and the volatiles removed in vacuo. The resulting slightly yellow solid was purified via Kugelrohr distillation to afford 50 (5.97 g, 96%) as white crystals. $R_f$ 0.56 (cyclohexane:ethylacetate 10:1).

$^1$H NMR (500 MHz, $CDCl_3$) δ [ppm] 10.52 (s, 1H, CHO), 7.52-7.50 (m, 1H, ar), 7.26 (t, $^3J$=7.0 Hz 1H, ar), 7.22-7.20 (m, 2H, ar), 2.58 (s, 3H, $CH_3$); $^{13}C\{^1H\}$ NMR (125.77 MHz, $CDCl_3$) δ [ppm] 194.6, 142.7, 133.6, 131.8, 131.7, 131.4, 128.3, 21.2.

(b) 3,3',5'-Trimethyl-biphenyl-carbaldehyde (51)

(via Suzuki coupling): In a 250 ml Schlenk flask dioxane, abs (60 ml), $Pd(OAc)_2$ (175 mg), SIMES (N,N'-bis(2,4,6-trimethylphenyl)-imidazolinium chloride, 777 mg) and $Cs_2CO_3$ (12.4 g) were stirred for 45 min at 80° C. until a grey solution had formed. Benzaldehyde 50 (3.1 g, 15.6 mmol) and 3,5-dimethylphenylboronic acid were added and the mixture stirred for 2 h at 80° C. (quantitative conversion, GC). The reaction mixture was allowed to cool to ambient temperature and treated with NaOH (100 ml of a 1 N solution) and diethylether (200 ml) and transferred into a separation funnel. The aqueous phase was extracted with $Et_2O$ (2×100 ml), the combined organic layers were subsequently washed with NaOH (100 ml, 1 N), brine (100 ml), dried over MgSO4, and the volatiles removed in vacuo. The resulting brown oil was purified by filtration over a short pad of silica gel (10×5 cm, eluent: cyclohexane/ethylacetate 20:1) to afford 51 (3.1 g, 89%) as a yellow oil. $R_f$ 0.66 (cyclohexane:ethylacetate (10:1)). The product was used without any further purification.

$^1$H NMR (300 MHz, $CDCl_3$) δ [ppm] 9.96 (s, 1H, CHO), 7.44 (t, $^3J$=7.8 Hz 1H, ar), 7.25 (d, $^3J$=3.6 Hz 2H, ar), 7.04 (s, 1H, ar), 6.95, (s, 2H, ar), 2.65 (s, 3H, $CH_3$), 2.36 (s, 6H, $CH_3$); $^{13}C\{^1H\}$ NMR (75.4 MHz, $CDCl_3$) δ [ppm] 195.0, 140.0, 139.0, 138.0, 132.7, 132.2, 131.9, 131.0, 129.7, 128.6, 128.2, 21.7, 21.4; IR (KBr): ν=3436 (br), 2920, 2858, 2765, 1689, 1677, 1600, 1584, 1463, 1191.

(c) 3,3',5'-Trimethyl-biphenyl-carboxylic Acid (52)

The aldehyde 51 (2.75 g, 11.5 mmol) was dissolved in acetonitrile (18 ml, technical grade). $NaH_2PO_4$ (0.453 g, dissolved in 5.5 ml $H_2O$) and $H_2O_2$ (1.93 ml of a 30% solution) was added. The reaction mixture was cooled to 0° C. (with ice/water) and $NaClO_2$ (2.2 g, dissolved in 19 ml water) was added within 60 min via a syringe. The solution was allowed to warm to ambient temperature and was stirred for additional 3.5 h. Then $Na_2SO_3$ (100 mg) was added, stirred for 5 min. After treatment with HCl (50 ml of a 10% solution) the reaction mixture was extracted with ether (3×75 ml). The combined organic phase was extracted with NaOH (4×75 ml, 1 N). The combined NaOH layers were acidified with HCl to pH 1 and extracted again with $Et_2O$. The combined organic layers were dried over $MgSO_4$ and the volatiles removed in vacuo to afford 52 (2.95 g, quant.) as a colorless oil. The product was used without any further purification.

$^1$H NMR (300 MHz, $CDCl_3$) δ [ppm] 7.36-7.18 (m, 3H, ar), 7.04 (s, 2H, ar), 6.98 (s, 1H, ar), 2.45 (s, 3H, $CH_3$), 2.32 (s, 6H, $CH_3$); $^{13}C\{^1H\}$ NMR (75.4 MHz, $CDCl_3$) δ [ppm] 180.7, 140.6, 140.4, 138.0, 135.4, 132.1, 129.8, 129.4, 129.1, 127.6, 126.3, 21.4, 20.0.

(d) 1,3,8-Trimethylfluoren-9-one (53)

In a 250 ml 1-necked round bottom flask the biphenyl-carboxylic acid 52 (3.0 g, 12.9 mmol) was treated with concentrated sulphuric acid (40 ml) at 0° C. (ice bath). The resulting dark brown solution was stirred for 15 min at 0° C., then for additional 1 h at ambient temperature. The reaction mixture was poured in ice (100 g) whereupon the color changes to a bright yellow. The suspension was neutralized with $K_2CO_3$ and extracted with $Et_2O$ (3×100 ml). The combined organic phases were washed with brine (75 ml), dried over $MgSO_4$, filtered and the volatiles removed in vacuo to afford 53 (2.8 g, 98%) as yellow crystals. $R_f$ 0.52 (cyclohexane:ethylacetate 10:1). The product was used without any further purification.

$^1$H NMR (500 MHz, $CDCl_3$) δ [ppm] 7.30-7.28 (m, 2H, ar), 7.14 (s, 1H, ar), 7.02-7.00 (m, 1H, ar), 6.82 (s, 1H, ar), 2.61 (s, 3H, $CH_3$), 2.57 (s, 3H, $CH_3$), 2.38 (s, 3H, $CH_3$); $^{13}C\{^1H\}$ NMR (125.77 MHz, $CDCl_3$) δ [ppm] 196.3, 144.7, 144.5, 144.2, 138.9, 138.8, 133.4, 132.2, 131.7, 131.5, 128.8, 118.6, 117.4, 21.9, 17.7, 17.6; IR (KBr): ν=3049, 3020, 2919, 1698, 1615, 1595, 1454, 1373, 1296, 1170.

(e) 1,3,8-Trimethylfluorene (54)

1,3,8-Trimethylfluoren-9-one (53) was reduced according to the general procedure of Carruthers et al. (W. Carruthers, D. Whitmarsh, J. Chem. Soc. Perkin Trans, I 1973, 1511). 1,3,8-Trimethylfluoren-9-one (53) (2.74 g, 12.3 mmol) was dissolved in propionic acid (235 ml). Red phosphorus (3.0 g) and concentrated HI (40 ml) were added and the reaction mixture was refluxed for 24 h. Quantitative conversion was shown by TLC. The reaction mixture was diluted with water (250 ml), neutralized with NaOH and extracted with Et$_2$O (4×125 ml). The combined organic layers were washed with brine (2×125 ml), dried over MgSO$_4$, filtered and the volatiles removed in vacuo to afford 2.56 g (quant.) 54 as a white solid.

$^1$H NMR (500 MHz, CDCl$_3$) δ [ppm] 7.60 (d, $^3$J=7.5 Hz, 1H, ar), 7.44 (s, 1H, ar), 7.28 (t, $^3$J=7.5 Hz, 1H, ar), 7.10 (d, $^3$J=7.0 Hz, 1H, ar), 6.95 (s, 1H, ar), 3.63 (s, 2H, CH$_2$), 2.44 (s, 3H, CH$_3$), 2.42 (s, 3H, CH$_3$), 2.40 (s, 3H, CH$_3$); $^{13}$C{$^1$H} NMR (125.77 MHz, CDCl$_3$) δ [ppm] 141.3, 140.9, 140.8, 138.0, 135.6, 133.1, 132.8, 127.6, 126.4, 125.9, 117.1, 116.4, 33.4, 20.4, 17.9, 17.8; IR (KBr): ν=3038, 3012, 2964, 2917, 2874, 1612, 1592, 1455, 1261.

(f) 1,3,8-Trimethyl-9-ethyl-fluorene (55)

The substitution reaction at the 9-position was performed according to the general procedure for the synthesis of 9-substituted fluorenes described above in item IV(i). 1,3,8-Trimethylfluorene (54) (1.2 g, 5.77 mmol) was used instead of fluorene, n-BuLi (3.0 ml, 2.5 M in hexane, 7.5 mmol), RX=1-iodoethane (1.35 g, 8.65 mmol). 55 was isolated to give a white solid (1.36 g, quant.).

$^1$H NMR (300 MHz, CDCl$_3$) δ [ppm] 7.55 (d, $^3$J=7.2 Hz, 1H, ar), 7.40 (s, 1H, ar), 7.27 (t, $^3$J=7.2 Hz, 1H, ar), 7.08 (d, $^3$J=7.5 Hz, 1H, ar), 6.93 (s, 1H, ar), 4.23 (t, $^3$J=4.2 Hz, 1H, 9HFlu), 2.49 (s, 3H, CH$_3$), 2.46 (s, 3H, CH$_3$), 2.43 (s, 3H, CH$_3$), 2.30 (dq, $^3$J=4.2 Hz, 2H, CH$_2$), 0.19 (t, $^3$J=7.8 Hz 3H, CH$_3$); $^{13}$C{$^1$H} NMR (75.4 MHz, CDCl$_3$) δ [ppm] 145.3, 142.1, 136.7, 134.1, 133.7, 129.6, 128.5, 127.0, 118.0, 117.2, 46.7, 21.5, 21.1, 19.2, 19.1, 7.2.

(iv) Preparation of 9-ethyl-2,7-dibromofluorene (56)

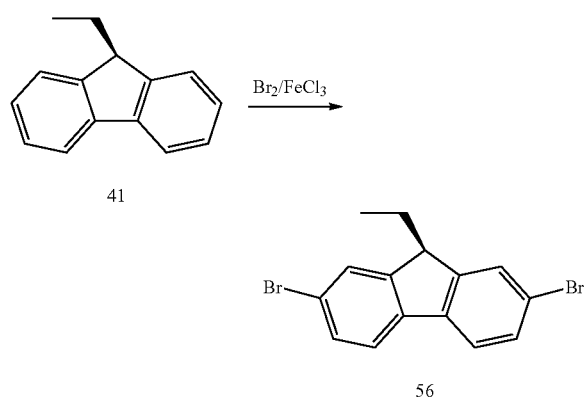

In a 250 ml four-necked round bottom flask (wrapped with Al foil) 9-ethylfluorene (41) (5 g, 25.7 mmol) was dissolved in dry CHCl$_3$ (50 ml). Anhydrous FeCl$_3$ (0.1 g, 0.63 mmol) was added. Under an argon atmosphere bromine (8.64 g, 54.1 mmol, dissolved in 25 ml chloroform) was added dropwise at 0° C. during 20 min while stirring. After completion of the addition the reaction mixture was stirred for 3 h at ambient temperature. Then a solution of Na$_2$S$_2$O$_3$ (20% (w/w) in water) was added and the mixture was transferred to a separation funnel. The aqueous phase was discarded and the organic layer was washed subsequently with a solution of NaHCO$_3$ (saturated, 3×40 ml) and water (1×40 ml). The organic layer was dried over MgSO$_4$, filtered and the volatiles removed in vacuo to afford a yellow solid. Recrystallization from ethanol afforded 56 (6.3 g, 70%) as white crystals.

$^1$H NMR (500 MHz, CDCl$_3$) δ [ppm] 7.61 (s, 2H, ar), 7.56 (d, $^3$J=8.5 Hz, 2H, ar), 7.48 (dd, $^3$J=8.5 Hz, $^4$J=1.5 Hz, 2H, ar), 3.94 (t, $^3$J=5.0 Hz, 1H, 9HFlu), 2.06 (dq, $^3$J=5.5 Hz, $^3$J=7.5 Hz, 2H, CH$_2$), 0.68 (t, $^3$J=7.5 Hz 3H, CH$_3$); $^{13}$C{$^1$H} NMR (125.77 MHz, CDCl$_3$) δ [ppm] 148.9, 139.4, 130.3, 127.7, 121.2, 48.4, 25.3, 9.4; HRMS Calcd. for C$_{15}$H$_{12}$Br$_2$: 349.9305, found 349.9286.

V. Preparation of Fluorenyl Phosphonium Salts (i) Preparation of 9-Substituted Fluorenyl-Phosphonium-Salts General procedure for the synthesis of 9-substituted fluorenyl-phosphonium-salts:

To a solution of a 9-substituted fluorene (31 mmol) in Et$_2$O, abs, (100 ml) n-BuLi (29 mmol, 2.5 M solution in hexane) was added at −60° C. The solution immediately turned red and was stirred for 10 min at −60° C., then for additional 2 h at ambient temperature. After cooling to −60° C. again, a dialkylphosphinous chloride R$_2$PCl (22 mmol) was added. The reaction mixture was stirred for 10 min at −60° C., then overnight at rt. After removing the LiCl by filtration over a short pad of Celite®, the resulting clear filtrate was quenched with HBF$_4$ (31.5 mmol of a diethylether complex). After separation via suction filtration the crude product was dissolved in 20 ml of CHCl$_3$ and added dropwise into Et$_2$O (1 l, vigorously stirred). Filtration and removal of the volatiles in vacuo afforded the pure product as a white solid.

The following 9-substituted fluorenyl-phosphonium-salts were prepared according to the above general procedure:

9-MeFluPCy$_2$.HBF$_4$ (8a)

Fluorene derivative=9-methylfluorene (40) (1.0 g, 5.55 mmol), n-BuLi (2.7 ml of a 2.0 M in hexane, 5.4 mmol), R$_2$PCl=Cy$_2$PCl (0.95 g, 4.08 mmol), HBF$_4$.Et$_2$O (1.4 ml, 5.55 mmol). 8a was isolated to give a white solid (1.35 g, 71%).

$^1$H NMR (300 MHz, CD$_3$CN) δ [ppm] 8.02-7.99 (m, 2H, ar), 7.81-7.78 (m, 2H, ar), 7.66-7.61 (m, 2H, ar), 7.56-7.50 (m, 2H, ar), 6.00 (d, $^1$J=464 Hz 1H, PH), 2.44-2.30 (m, 4H, CH$_2$), 2.03 (d, $^3$J=16.8 Hz, 3H, CH$_3$), 1.96-1.92 (m, 2H, CH), 1.75-1.49 (m, 8H, CH$_2$), 1.31-1.04 (m, 8H, CH$_2$); $^{13}$C{$^1$H} NMR (75.4 MHz, CD$_3$CN) δ [ppm] 140.9 (d, $^{PC}$J=3.1 Hz), 140.1 (d, $^{PC}$J=4.3 Hz), 130.0 (d, $^{PC}$J=2.0 Hz), 128.6 (d, $^{PC}$J=2.0 Hz), 124.6 (d, $^{PC}$J=3.3 Hz), 121.3, 47.6 (d, $^{PC}$J=33.9 Hz), 30.4 (d, $^{PC}$J=35 Hz), 28.5 (d, $^{PC}$J=3.9 Hz), 27.5 (d, $^{PC}$J=3.8 Hz), 25.8 (d, $^{PC}$J=13 Hz), 25.6 (d, $^{PC}$J=13 Hz), 24.4, 21.6; $^{31}$P{$^1$H} NMR (121.4 MHz, CD$_3$CN) δ [ppm] 38.8; $^{31}$P NMR (121.4 MHz, CD$_3$CN) δ [ppm] 38.8 (d, $^{PH}$J=463 Hz).

9-MeFluPiPr$_2$.HBF$_4$ (5a)

Fluorene derivative=9-methylfluorene (40) (1.5 g, 8.31 mmol), nBuLi (4.05 ml, 2.0 M in hexane, 8.1 mmol), R$_2$PCl=iPr$_2$PCl (0.9 ml, 5.67 mmol), HBF$_4$.Et$_2$O (2.4 ml, 9.51 mmol). 5a was isolated to give a white solid (1.37 g, 63%).

$^1$H NMR (300 MHz, CDCl$_3$) δ [ppm] 7.94-7.86 (m, 4H, ar), 7.60-7.49 (m, 4H, ar), 7.27 (d, $^1$J=483 Hz 1H, PH), 2.65-2.50 (m, 2H, CH), 2.15 (d, $^3$J(PH)=16.8 Hz, 3H, CH$_3$), 1.33 (dd, $^3J$=7.2 Hz, $^3$J(PH)=18.3 Hz, 6H, $CH_3$), 1.06 (dd, $^3J$=7.5 Hz, $^3$J(PH)=17.7 Hz, 6H, $CH_3$); $^{13}C\{^1H\}$ NMR (75.4 MHz, $CDCl_3$) δ [ppm] 142.2 (d, $^{PC}J$=2.2 Hz), 140.2 (d, $^{PC}J$=4.3 Hz), 130.3, 129.2 (d, $^{PC}J$=1.7 Hz), 125.2 (d, $^{PC}J$=3.7 Hz), 121.2, 47.9 (d, $^{PC}J$=34 Hz), 22.7, 21.2 (d, $^{PC}J$=36.3 Hz), 19.3 (d, $^{PC}J$=2.9 Hz), 17.8 (d, $^{PC}J$=3.0 Hz); $^{31}P\{^1H\}$ NMR (121.4 MHz, $CDCl_3$) δ [ppm] 39.4; $^{31}$P NMR (121.4 MHz, $CDCl_3$) δ [ppm] 39.4 (d, $^{PH}J$=482 Hz).

9-EtFluPCy$_2$.HBF$_4$ (9a)

Fluorene derivative=9-ethylfluorene (41) (1.65 g, 8.55 mmol), n-BuLi (3.3 ml, 2.5 M in hexane, 8.25 mmol), $R_2$PCl=Cy$_2$PCl (1.26 g, 5.43 mmol), HBF$_4$.Et$_2$O (2.2 ml, 8.7 mmol). 9a was isolated to give a white solid (1.97 g, 76%).

$^1$H NMR (300 MHz, $CDCl_3$) δ [ppm] 7.90-7.87 (m, 2H, ar), 7.79 (d, $^3J$=7.9 Hz, 2H, ar), 7.61-7.49 (m, 4H, ar), 6.54 (d, $^1J$=480 Hz 1H, PH), 2.80-2.71 (m, 2H, $CH_2$ (ethyl)), 2.30-2.18 (m, 2H, CH), 1.91-1.08 (m, 19H, $CH_2$), 0.32 (t, $^3J$=6.9 Hz, 3H, $CH_3$); $^{13}C\{^1H\}$ NMR (75.4 MHz, $CDCl_3$) δ [ppm] 141.6 (d, $^{PC}J$=4.5 Hz), 139.7 (d, $^{PC}J$=3.0 Hz), 130.2, 129.1, 125.1 (d, $^{PC}J$=3.0 Hz), 121.1, 52.9 (d, $^{PC}J$=33 Hz), 31.2 (d, $^{PC}J$=35 Hz), 29.4 (d, $^{PC}J$=2.6 Hz), 28.0 (d, $^{PC}J$=4 Hz), 27.4, 26.7 (d, $^{PC}J$=13 Hz), 26.5 (d, $^{PC}J$=13 Hz), 24.9, 6.7 (d, $^{PC}J$=11 Hz); $^{31}P\{^1H\}$ NMR (121.4 MHz, $CDCl_3$) δ [ppm] 34.4; $^{31}$P NMR (121.4 MHz, $CDCl_3$) δ [ppm] 34.4 (d, $^{PC}J$=480 Hz).

9-EtFluPiPr$_2$.HBF$_4$ (6a)

Fluorene derivative=9-Ethylfluorene (41) (0.54 g, 2.78 mmol), n-BuLi (1.35 ml, 2.0 M in hexane, 2.7 mmol), $R_2$PCl=iPr$_2$PCl (0.269 g, 1.76 mmol), HBF$_4$.Et$_2$O (0.55 ml, 2.7 mmol). 6a was isolated to give a white solid (0.69 g, 99%).

$^1$H NMR (300 MHz, $CDCl_3$) δ [ppm] 7.90-7.82 (m, 4H, ar), 7.61-7.50 (m, 4H, ar), 6.70 (d, $^1J$=480 Hz 1H, PH), 2.79-2.72 (m, 2H, $CH_2$ (ethyl)), 2.64-2.54 (m, 2H, CH), 1.30 (dd, $^3J$=7.2 Hz, $^3$J(PH)=18.3 Hz, 6H, $CH_3$), 1.05 (dd, $^3J$=7.2 Hz, $^3$J(PH)=17.7 Hz, 6H, CHO, 0.33 (t, $^3J$=6.9 Hz, 3H, $CH_3$); $^{13}C\{^1H\}$ NMR (75.4 MHz, $CDCl_3$) δ [ppm] 141.6 (d, $^{PC}J$=4.8 Hz), 139.5 (d, $^{PC}J$=3.0 Hz), 130.3 (d $^{PC}J$=2.1 Hz), 129.2 (d, $^{PC}J$=3.4 Hz), 125.1 (d, $^{PC}J$=3.4 Hz), 121.3, 52.7 (d, $^{PC}J$=34 Hz), 27.6, 21.3 (d, $^{PC}J$=36.7 Hz), 19.5 (d, $^{PC}J$=2.4 Hz), 17.8 (d, $^{PC}J$=3.5 Hz), 6.6 (d, $^{PC}J$=11 Hz);

$^{31}P\{^1H\}$ NMR (121.4 MHz, $CDCl_3$) δ [ppm] 40.8; $^{31}$P NMR (121.4 MHz, $CDCl_3$) δ [ppm] 40.8 (d, $^{PH}J$=478 Hz).

9-iPrFluPCy$_2$.HBF$_4$ (22a)

Fluorene derivative=9-i-propylfluorene(42) (1.15 g, 5.54 mmol), n-BuLi (2.7 ml, 2.0 M in hexane, 5.4 mmol), $R_2$PCl=Cy$_2$PCl (0.9 ml, 4.08 mmol), HBF$_4$.Et$_2$O (1.2 ml, 4.76 mmol). 22a was isolated to give a white solid (1.30 g, 64%).

$^1$H NMR (300 MHz, $CDCl_3$) δ [ppm] 7.89 (d, $^3J$=6.9 Hz, 2H, ar), 7.79 (d, $^3J$=7.5 Hz, 2H, ar), 7.62-7.50 (m, 4H, ar), 6.79 (d, $^1J$=479 Hz 1H, PH), 3.01 (dq, $^3J$=6.6 Hz, $^3J$=4.8 Hz, 1H, CHCH$_3$), 2.21-2.09 (m, 2H, CH), 1.97-1.86 (m, 2H, $CH_2$), 1.81-1.59 (m, 6H, $CH_2$), 1.51-1.37 (m, 4H, $CH_2$), 1.23-1.07 (m, 8H, $CH_2$), 0.93 (d, $^3J$=6.6 Hz, 6H, $CH_3$);

$^{13}C\{^1H\}$ NMR (75.4 MHz, $CDCl_3$) δ [ppm] 141.5 (d, $^{PC}J$=5.1 Hz), 139.6 (d, $^{PC}J$=2.6 Hz), 130.3, 129.0, 125.7 (d $^{PC}J$=2.9 Hz), 121.1, 56.4 (d, $^{PC}J$=33 Hz), 34.4, 29.9 (d, $^{PC}J$=35.6 Hz), 29.2 (d, $^{PC}J$=3.8 Hz), 28.1 (d, $^{PC}J$=3.7 Hz), 26.9 (d, $^{PC}J$=12.9 Hz), 26.6 (d, $^{PC}J$=12.5 Hz), 24.9, 17.8 (d, $^{PC}J$=6.6 Hz); $^{31}P\{^1H\}$ NMR (121.4 MHz, $CDCl_3$) δ [ppm] 25.0; $^{31}$P NMR (121.4 MHz, $CDCl_3$) δ [ppm] 25.0 (d, $^{PH}J$=477 Hz).

9-iPrFluPiPr$_2$.HBF$_4$ (23a)

Fluorene derivative=9-i-propylfluorene (42) (1.16 g, 5.57 mmol), n-BuLi (2.7 ml, 2.0 M in hexane, 5.4 mmol), $R_2$PCl=iPr$_2$PCl (0.66 g, 4.1 mmol), HBF$_4$.Et$_2$O (1.2 ml, 4.76 mmol). 23a was isolated to give a white solid (1.20 g, 71%).

$^1$H NMR (300 MHz, $CDCl_3$) δ [ppm] 7.90-7.82 (m, 4H, ar), 7.62-7.50 (m, 4H, ar), 6.99 (d, $^1J$=477 Hz 1H, PH), 3.09-2.99 (m, 1H, CH), 2.59-2.44 (m, 2H, CH), 1.32 (dd, $^3J$=7.5 Hz, $^3$J(PH)=18.9 Hz, 6H, $CH_3$), 1.03 (dd, $^3J$=7.5 Hz, $^3$J(PH)=17.7 Hz, 6H, $CH_3$), 0.94 (d, $^3J$=6.9 Hz, 6H, $CH_3$); $^{13}C\{^1H\}$ NMR (75.4 MHz, $CDCl_3$) δ [ppm] 141.5 (d, $^{PC}J$=5.1 Hz), 139.4 (d, $^{PC}J$=2.4 Hz), 130.3 (d $^{PC}J$=1.6 Hz), 129.1 (d, $^{PC}J$=1.3 Hz), 125.7 (d, $^{PC}J$=3.6 Hz), 121.2, 56.1 (d, $^{PC}J$=33.2 Hz), 34.4, 21.1 (d, $^{PC}J$=38.5 Hz), 19.5 (d, $^{PC}J$=2.2 Hz), 17.8 (d, $^{PC}J$=2.6 Hz), 6.6 (d, $^{PC}J$=6.5 Hz); $^{31}P\{^1H\}$ NMR (121.4 MHz, $CDCl_3$) δ [ppm] 31.3; $^{31}$P NMR (121.4 MHz, $CDCl_3$) δ [ppm] 31.3 (d, $^{PH}J$=473 Hz).

9-n-PrFluPCy$_2$.HBF$_4$ (24a)

Fluorene derivative=9-n-propylfluorene (43) (3.0 g, 14.4 mmol), n-BuLi (5.6 ml, 2.5 M in hexane, 14.0 mmol), $R_2$PCl=Cy$_2$PCl (2.37 g, 10.2 mmol), HBF$_4$.Et$_2$O (2.0 ml, 14 mmol). 24a was isolated to give a white solid (4.13 g, 73%).

$^1$H NMR (500 MHz, $CDCl_3$) δ [ppm] 7.87 (d, $^3J$=7.5 Hz, 2H, ar), 7.79 (d, $^3J$=7.5 Hz, 2H, ar), 7.59-7.50 (m, 4H, ar), 6.54 (d, $^1J$=480.5 Hz 1H, PH), 2.67-2.63 (m, 2H, $CH_2$ (propyl)), 2.24-2.21 (m, 2H, CH), 1.91-1.10 (m, 19H, $CH_2$), 0.73 (t, $^3J$=7.5 Hz, 3H, $CH_9$), 0.66-0.58 (m, 2H, $CH_2$ (propyl)); $^{13}C\{^1H\}$ NMR (125.75 MHz, $CDCl_3$) δ [ppm] 141.4 (d, $^{PC}J$=4.5 Hz), 140.2 (d, $^{PC}J$=3.8 Hz), 130.2, 129.1, 125.1 (d, $^{PC}J$=2.8 Hz), 121.1, 52.4 (d, $^{PC}J$=33 Hz), 40.0, 31.3 (d, $^{PC}J$=34.6 Hz), 29.4 (d, $^{PC}J$=3.6 Hz), 28.1 (d, $^{PC}J$=3.3 Hz), 26.8 (d, $^{PC}J$=13.8 Hz), 26.5 (d, $^{PC}J$=12.4 Hz), 24.9, 16.0 (d, $^{PC}J$=10.4 Hz), 13.6; $^{31}P\{^1H\}$ NMR (202.45 MHz, $CDCl_3$) δ [ppm] 34.9; $^{31}$P NMR (202.45 MHz, $CDCl_3$) δ [ppm] 34.9 (d, $^{PH}J$=483 Hz).

9-C$_{18}$H$_{37}$FluPCy$_2$.HBF$_4$ (11a)

Fluorene derivative=9-octadecylfluorene (44) (2.48 g, 5.9 mmol), n-BuLi (2.1 ml, 2.5 M in hexane, 5.25 mmol), $R_2$PCl=Cy$_2$PCl (0.92 g, 3.94 mmol), HBF$_4$.Et$_2$O (1.8 ml). In the absence of precipitation water (80 ml, treated with aqueous HBF$_4$ (8 N)) was added, whereupon a white solid precipitated. The solid was removed via suction filtration to afford 11a as a white solid (2.6 g, 94%).

$^1$H NMR (300 MHz, $CDCl_3$) δ [ppm] 7.87 (d, $^3J$=7.2 Hz, 2H, ar), 7.79-7.77 (m, 2H, ar), 7.60-7.50 (m, 4H, ar), 6.59 (d, $^1J$=483 Hz 1H, PH), 2.71-2.59 (m, 2H, $CH_2$), 2.27-2.13 (m, 2H, CH), 1.92-1.02 (m, 50H, $CH_2$), 0.87 (t, $^3J$=6.6 Hz, 3H, $CH_3$), 0.60-0.49 (m, 2H, $CH_2$); $^{13}C\{^1H\}$ NMR (75.4 MHz, $CDCl_3$) δ [ppm] 141.4 (d, $^{PC}J$=4.2 Hz), 140.2, 130.2, 129.1, 125.1, 121.0, 52.4 (d, $^{PC}J$=32.2 Hz), 34.0, 31.9, 31.3 (d, $^{PC}J$=34.5 Hz), 29.7-29.1 ($CH_2$, 14×), 28.1 (d, $^{PC}J$=3.2 Hz), 26.8 (d, $^{PC}J$=13.2 Hz), 26.6 (d, $^{PC}J$=12.6 Hz), 24.9, 22.7, 22.4 (d, $^{PC}J$=9.9 Hz), 14.1; $^{31}P\{^1H\}$ NMR (121.4 MHz, $CDCl_3$) δ [ppm] 34.1; $^{31}$P NMR (121.4 MHz, $CDCl_3$) δ [ppm] 34.1 (d, $^{PH}J$=482 Hz).

9-C$_{18}$H$_{37}$FluPiPr$_2$.HBF$_4$ (7a)

Fluorene derivative=9-octadecylfluorene (44) (2.38 g, 5.7 mmol), n-BuLi (2.0 ml, 2.5 M in hexane, 5.0 mmol), $R_2PCl$=i$Pr_2$PCl (0.575 g, 3.77 mmol), $HBF_4 \cdot Et_2O$ (2.0 ml, 9.8 mmol). In the absence of precipitation, the volatiles were evaporated in vacuo to give a colorless solid, which was dissolved in diethylether (50 ml) and treated with $HBF_4 \cdot Et_2O$ (1 ml). Aqueous $HBF_4$ (50 ml, 4 N) was added, the mixture was stirred vigorously, the aqueous phase separated and kept in an open beaker overnight. The crystals which had formed were separated via suction filtration and dried in vacuo to afford 7a (1.90 g, 81%) as white crystals.

$^1$H NMR (300 MHz, $CDCl_3$) δ [ppm] 7.88 (d, $^3J$=6.9 Hz, 2H, ar), 7.81 (d, $^3J$=6.9 Hz, 2H, ar), 7.59-7.53 (m, 4H, ar), 6.65 (d, $^1J$=481 Hz 1H, PH), 2.71-2.61 (m, 2H, $CH_2$), 2.61-2.49 (m, 2H, CH), 1.31 (dd, $^3J$=7.2 Hz, $^3J(PH)$=12.3 Hz, 6H, $CH_3$), 1.27-1.11 (m, 30H, $CH_2$), 1.05 (dd, $^3J$=7.5 Hz, $^3J(PH)$=17.4 Hz, 6H, $CH_3$), 0.88 (t, $^3J$=6.9 Hz, 3H, $CH_3$), 0.61-0.50 (m, 2H, $CH_2$); $^{13}$C{$^1$H} NMR (75.4 MHz, $CDCl_3$) δ [ppm] 141.4 (d, $^{PC}J$=5.1 Hz), 139.9 (d, $^{PC}J$=2.9 Hz), 130.3, 129.2, 125.0 (d, $^{PC}J$=2.9 Hz), 121.3, 52.3 (d, $^{PC}J$=33.5 Hz), 34.1, 31.9, 29.6 ($CH_2$, 11×), 29.5, 29.4, 29.3, 29.1, 22.7, 22.2 (d, $^{PC}J$=10.5 Hz), 21.3 (d, $^{PC}J$=37 Hz), 19.5 (d, $^{PC}J$=1.8 Hz), 17.8 (d, $^{PC}J$=2.5 Hz), 14.1; $^{31}$P{$^1$H} NMR (121.4 MHz, $CDCl_3$) δ [ppm] 40.8; $^{31}$P NMR (121.4 MHz, $CDCl_3$) δ [ppm] 40.8 (d, $^{PC}J$=480 Hz).

9-BnFluPCy$_2$.HBF$_4$ (10a)

Fluorene derivative=9-benzylfluorene (45) (6.0 g, 23.2 mmol), n-BuLi (8.6 ml, 2.5 M in hexane, 21.5 mmol), $R_2PCl$=$Cy_2$PCl (3.85 g, 16.5 mmol), $HBF_4 \cdot Et_2O$ (3.22 ml, 23.6 mmol). 10a was isolated to give a white solid (5.43 g, 61%).

$^1$H NMR (500 MHz, acetone-$d_6$) δ [ppm] 8.32-8.30 (m, 2H, ar), 7.88-7.86 (m, 2H, ar), 7.60-7.57 (m, 4H, ar), 6.90-6.87 (m, 1H, ar), 6.82-6.79 (m, 2H, ar), 6.70 (d, $^1J$=472.5 Hz, 1H, PH), 6.69-6.67 (m, 2H, ar), 4.25 (d, $^3J$=7 Hz, 2H, $CH_2$), 2.88-2.79 (m, 2H, CH), 1.96-1.94 (m, 2H, $CH_2$), 1.77-1.08 (m, 18H, $CH_2$); $^{13}$C{$^1$H} NMR (125.77 MHz, acetone-$d_6$) δ [ppm] 142.7 (d, $^{PC}J$=4.5 Hz), 140.5 (d, $^{PC}J$=3.5 Hz), 133.8, 133.7, 131.1, 129.3, 128.1, 127.7, 127.3 (d, $^{PC}J$=3.9 Hz), 122.1, 53.8 (d, $^{PC}J$=32.2 Hz), 39.5, 32.0 (d, $^{PC}J$=34.5 Hz), 30.0 (d, $^{PC}J$=3.5), 29.0 (d, $^{PC}J$=3.0), 27.2 (d, $^{PC}J$=12.0), 27.0 (d, $^{PC}J$=13.3), 25.6; $^{31}$P{$^1$H} NMR (202.46 MHz, acetone-$d_6$) δ [ppm] 35.7; $^{31}$P NMR (202.46 MHz, acetone-$d_6$) δ [ppm] 35.7 (d, $^{PH}J$=472.6 Hz).

9-BnFluPiPr$_2$.HBF$_4$ (26a)

Fluorene derivative=9-benzylfluorene (45) (8.1 g, 31.3 mmol), n-BuLi (11.6 ml, 2.5 M in hexane, 29 mmol), $R_2PCl$=i$Pr_2$PCl (3.32 g, 22.3 mmol), $HBF_4 \cdot Et_2O$ (4.35 ml, 31.9 mmol). After separation via suction filtration, the crude product was dissolved in acetonitrile (20 ml), added dropwise into $Et_2O$ (1l, vigorous stirring). Filtration and removal of the volatiles in vacuo afforded the pure product 26a as white solid (9.8 g, 95%).

$^1$H NMR (500 MHz, $CD_3CN$) δ [ppm] 8.04-8.02 (m, 2H, ar), 7.79-7.77 (m, 2H, ar), 7.56-7.54 (m, 4H, ar), 6.92-6.90 (m, 1H, ar), 6.84-6.81 (m, 2H, ar), 6.61-6.60 (m, 2H, ar), 6.35 (d, $^1J$=470 Hz, 1H, PH), 4.00 (d, $^3J$=6.00 Hz, 2H, $CH_2$), 2.83-2.75 (m, 2H, CH), 1.18 (dd, $^3J$=7.5 Hz' $^3J(PH)$=18.5 Hz, 6H, $CH_3$) 1.00 (dd, $^3J$=7.0 Hz, $^3J(PH)$=17.5 Hz, 6H, $CH_3$); $^{13}$C{$^1$H} NMR (125.8 MHz, $CD_3CN$) δ [ppm] 141.2 (d, $^{PC}J$=4.8 Hz), 138.7, 132.2 (d, $^{PC}J$=14.3 Hz), 130.0, 129.9, 128.2, 127.1, 126.7, 125.8 (d, $^{PC}J$=31.8 Hz), 38.5, 21.0 (d, $^{PC}J$=36.2 Hz), 18.3 (d, $^{PC}J$=2.3 Hz), 17.0 (d, $^{PC}J$=1.4 Hz); $^{31}$P{$^1$H} NMR (202.5 MHz, $CD_3CN$) δ [ppm] 43.8; $^{31}$P NMR (202.5 MHz, $CD_3CN$) δ [ppm] 43.8 (d, $^{PH}J$=465.2 Hz).

9-Et-1-MeFluPCy$_2$.HBF$_4$ (12a)

Fluorene derivative=9-ethyl-1-methylfluorene (48) (2.0 g, 9.56 mmol), n-BuLi (3.67 ml, 2.5 M in hexane, 9.18 mmol), $R_2PCl$=$Cy_2$PCl (1.78 g, 7.65 mmol), $HBF_4 \cdot Et_2O$ (1.25 ml, 9.18 mmol). 12a was isolated to give a white solid (3.5 g, 93%).

$^1$H NMR (500 MHz, $CDCl_3$) δ [ppm] 7.86 (d, $^3J$=7.5 Hz, 1H, ar), 7.74 (d, $^3J$=7.5 Hz, 1H, ar), 7.68 (d, $^3J$=7.5 Hz, 1H, ar), 7.59 (t, $^3J$=7.5 Hz, 1H, ar), 7.54-7.47 (m, 2H, ar), 7.24 (d, $^3J$=7.5 Hz, 1H, ar), 6.50 (dd, $^1J$=465.5 Hz, $^3J$=4.0 Hz, 1H, PH), 3.06-2.97 (m, 1H, $CH_2$ (ethyl)), 2.79-2.68 (m, 2H, $CH_2$ (ethyl)+CH(Cy)), 2.66 (s, 3H, $CH_3$), 2.35-2.32 (m, 1H, CH(Cy)), 2.02-1.65 (m, 7H, $CH_2$), 1.56-1.34 (m, 7H, $CH_2$), 1.13-1.08 (m, 1H, $CH_2$), 0.91-0.87 (m, 4H, $CH_2$), 0.68-0.59 (m, 1H, $CH_2$), 0.39 (t, $^3J$=7.0 Hz, 3H, $CH_3$); $^{13}$C{$^1$H} NMR (125.75 MHz, $CDCl_3$) δ [ppm] 142.6 (d, $^{PC}J$=4.0 Hz), 142.3 (d, $^{PC}J$=4.5 Hz), 139.8 (d, $^{PC}J$=4.5 Hz), 137.4 (d, $^{PC}J$=3.3 Hz), 136.8 (d, $^{PC}J$=2.8 Hz), 132.2, 131.0, 130.8, 129.2 (d, $^{PC}J$=2.3 Hz), 124.6 (d, $^{PC}J$=4.1 Hz), 121.4, 119.1, 54.7 (d, $^{PC}J$=31.3 Hz), 32.1 (d, $^{PC}J$=37.3 Hz), 31.8 (d, $^{PC}J$=33.3 Hz), 30.6 (d, $^{PC}J$=3.8 Hz), 28.7 (d, $^{PC}J$=3.6 Hz), 28.5 (d, $^{PC}J$=3.4 Hz), 27.2, 27.2, 27.2, 27.1, 27.1, 27.0, 26.9, 26.8, (d, $^{PC}J$=13.2 Hz), 27.1 (d, $^{PC}J$=13.2 Hz), 25.2, 20.1, 7.4 (d, $^{PC}J$=11 Hz); $^{31}$P{$^1$H} NMR (202.5 MHz, $CDCl_3$) δ [ppm] 27.5; $^{31}$P NMR (202.5 MHz, $CDCl_3$) δ [ppm] 27.5 (d, $^{PH}J$=471 Hz).

9-Et-1,3,8-Me$_3$-FluPCy$_2$.HBF$_4$ (29a)

Fluorene derivative=1,3,8-trimethyl-9-ethyl-fluorene (55) (0.8 g, 3.4 mmol), n-BuLi (1.29 ml, 2.5 M in hexane), $R_2PCl$=$Cy_2$PCl (0.633 g, 2.72 mmol), $HBF_4 \cdot Et_2O$ (0.8 ml, 3.2 mmol). 29a was isolated to give a white solid (1.29 g, 92%).

$^1$H NMR (300 MHz, $CDCl_3$) δ [ppm] 7.89 (d, $^3J$=7.5 Hz, 1H, ar), 7.52 (s, 1H, ar), 7.49-7.43 (m, 1H, ar), 7.22 (d, $^3J$=7.5 Hz, 1H, ar), 7.05 (s, 1H, ar), 6.30 (dt, $^1J$=469 Hz, $^3J$=4.5 Hz, 1H, PH), 2.96 (dg, $^3J(PH)$=5.7 Hz, $^3J$=7.2 Hz, 2H, $CH_2$ (ethyl)), 2.66 (s, 3H, $CH_3$), 2.62 (s, 3H, $CH_3$), 2.44 (s, 3H, $CH_3$), 2.24-2.19 (m, 2H, CH), 2.12-1.04 (m, 20H, $CH_2$), 0.44 (t, $^3J$=7.2 Hz, 3H, $CH_3$); $^{13}$C{$^1$H} NMR (75.4 MHz, $CDCl_3$) δ [ppm] 142.6 (d, $^{PC}J$=4.8 Hz), 142.5 (d, $^{PC}J$=4.5 Hz), 140.8, 137.0 (d, $^{PC}J$=4.4 Hz), 135.4 (d, $^{PC}J$=3.2 Hz), 135.0 (d, $^{PC}J$=3.2 Hz), 133.8 (d, $^{PC}J$=4.1 Hz), 133.3 (d, $^{PC}J$=2.3 Hz), 132.1 (d, $^{PC}J$=2.3 Hz), 130.5 (d, $^{PC}J$=2.4 Hz), 119.3, 118.6, 56.8 (d, $^{PC}J$=28.9 Hz), 32.9 (d, $^{PC}J$=17.3 Hz), 32.5 (d, $^{PC}J$=17.7 Hz), 29.4 (d, $^{PC}J$=3.3 Hz), 27.6 (d, $^{PC}J$=4.8 Hz), 27.5 (d, $^{PC}J$=4.8 Hz), 26.9 (d, $^{PC}J$=13.5 Hz), 26.7 (d, $^{PC}J$=13.1 Hz), 24.8, 23.7, 21.3, 20.3, 20.1, 7.1 (d, $^{PC}J$=11 Hz); $^{31}$P{$^1$H} NMR (121.4 MHz, $CDCl_3$) δ [ppm] 27.7; $^{31}$P NMR (121.4 MHz, $CDCl_3$) δ [ppm] 27.7 (d, $^{PH}J$=469 Hz).

9-PhFluPiPr$_2$.HBF$_4$ (30a)

Fluorene derivative=9-phenylfluorene (prepared according to a standard literature method, e.g. F. Ullman, R. von Wurstemberger, Chem. Ber. 1904, 37, 73-78) (0.72 g, 2.97 mmol), n-BuLi (1.08 ml, 2.5 M solution in hexane), $R_2PCl$=i$Pr_2$PCl (0.33 ml, 2.03 mmol), $HBF_4 \cdot Et_2O$ (0.6 ml, 2.37 mmol). 30a was isolated to give a white solid (0.84 g, 93%).

$^1$H NMR (300 MHz, $CDCl_3$) δ [ppm] 9.49 (d, $^1J$=490 Hz 1H, PH), 7.98-7.91 (m, 4H, ar), 7.85 (d, J=8.1 Hz, 2H, ar), 7.64-7.52 (m, 4H, ar), 7.45 (t, $^3J$=7.2 Hz, 2H, ar), 7.37-7.32 (m, 1H, ar), 2.30-2.21 (m, 2H, CH), 1.14 (dd, $^3J$=7.2 Hz, $^3J(PH)$=18.0 Hz, 6H, CH$_3$), 1.02 (dd, $^3J$=7.5 Hz, $^3J(PH)$=17.7 Hz, 6H, CH$_3$); $^{13}C\{^1H\}$ NMR (75.4 MHz, CDCl$_3$) δ [ppm] 140.6 (d, $^{PC}J$=4.5 Hz), 140.3 (d, $^{PC}J$=2.9 Hz), 135.2, 130.5, 130.0, 129.4, 129.1, 127.3 (d, $^{PC}J$=5.9 Hz), 126.7 (d, $^{PC}J$=3.1 Hz), 121.5, 56.5 (d, $^{PC}J$=33.8 Hz), 21.0 (d, $^{PC}J$=37.3 Hz), 19.6 (d, $^{PC}J$=2.4 Hz), 17.7 (d, $^{PC}J$=2.5 Hz); $^{31}P\{^1H\}$ NMR (121.4 MHz, CDCl$_3$) δ [ppm] 30.6; $^{31}P$ NMR (121.4 MHz, CDCl$_3$) δ [ppm] 30.6 (d, $^{PH}J$=489 Hz).

(ii) Preparation of HFluPtBu$_2$.HBF$_4$ (25a)

Fluorene (0.505 g, 3.04 mmol) dissolved in THF, abs (10 ml) was treated with n-BuLi (1.5 ml, 2.0 M in hexane) at −80° C. The mixture turned orange and was stirred for additional 4 h at ambient temperature. Then tBu$_2$PCl (0.476 g, 2.6 mmol) was added at −80° C., as well as 10 ml heptane, abs. The reaction mixture was refluxed overnight, filtered under Schlenk conditions over a short pad of Celite® and the clear filtrate quenched with HBF$_4$.Et$_2$O (0.7 ml, 2.8 mmol) to afford a white residue, which could be crystallized from ethylacetate. After separation of the solids via suction filtration the crude product was dissolved in 3 ml of CHCl$_3$ and added dropwise into Et$_2$O (200 ml, vigorously stirred). Filtration and removal of the volatiles in vacuo afforded pure 25a (0.54 g, 52%) as a white solid.

$^1H$ NMR (300 MHz, CD$_3$CN) δ [ppm] 8.05-7.98 (m, 2H, ar), 7.86-7.77 (m, 2H, ar), 7.63-7.54 (m, 4H, ar), 6.27 (d, $^1J$=463 Hz 1H, PH), 5.37 (d, $^2J(PH)$=15.6 Hz, 1H, CH), 1.85 (d, $^3J(PH)$=17.1 Hz, 9H, CH$_3$), 0.91 (d, $^3J(PH)$=17.1 Hz, 9H. CH$_3$); $^{13}C\{^1H\}$ NMR (75.4 MHz, CD$_3$CN) δ [ppm] 139.0, 135.1, 129.4 (d, $^{PC}J$=10 Hz), 128.1 (d, $^{PC}J$=32 Hz), 125.7 (d, $^{PC}J$=87 Hz), 121.2 (d, $^{PC}J$=28.0 Hz), 38.4 (d, $^{PC}J$=34 Hz), 36.5 (d, $^{PC}J$=23.7 Hz), 34.5 (d, $^{PC}J$=30.0 Hz), 27.5, 26.6; $^{31}P\{^1H\}$ NMR (121.4 MHz, CD$_3$CN) δ [ppm] 52.1; $^{31}P$ NMR (121.4 MHz, CD$_3$CN) δ [ppm] 52.1 (d, $^{PH}J$=462 Hz).

(iii) Preparation of 9-Et-2,7-Br$_2$FluPiPr$_2$.HBF$_4$ (31a)

In a 100 ml Schlenk flask diisopropylamine (1.03 ml, 7.4 mmol) was dissolved in THF (20 ml), abs. At −60° C. n-BuLi (2.7 ml of a 2.0 molar solution in hexane, 6.8 mmol) was added. The solution was stirred at −60° C. for 10 min, then for additional 30 min at 0° C. The formed LDA-solution was added to a solution of 9-ethyl-2,7-dibromofluorene (56) (2.5 g, 7.08 mmol) in Et$_2$O (40 ml) at −60° C. The red reaction mixture was stirred for 30 min at −60° C., then for 1.5 h at ambient temperature (at lower temperatures a thick reddish precipitate is formed). Then iPr$_2$PCl (0.9 ml, 5.66 mmol) was added at −60° C. The reaction mixture was stirred at ambient temperature for 2 h (color changes from red to yellow) and filtered over a small pad of Celite®. The clear, slightly yellow filtrate was quenched with HBF$_4$.Et$_2$O (1.80 ml, 13.2 mmol) which led to precipitation of the phosphonium salt as a white solid. The solid was separated via suction filtration, slurried in H$_2$O (15 ml, to remove residual ammonium salt) and filtered again. The collected white solid was dissolved in 10 ml chloroform and 1 ml acetonitrile, and the solution added dropwise to vigorously stirred Et$_2$O (400 ml) to obtain a colourless precipitate. Filtration and removal of the volatiles in vacuo afforded 31a as white solid (2.82 g, 90%).

$^1H$ NMR (500 MHz, CD$_3$CN) δ [ppm] 7.98 (t, $^4J$=1.5 Hz, 2H, ar), 7.91 (d, $^3J$=8.0 Hz, 2H, ar), 7.81 (dt, $^3J$=8.0 Hz, $^4J$=1.5 Hz 2H, ar), 6.24 (d, $^1J$=470 Hz 1H, PH), 2.80-2.71 (m, 2H, CH), 2.70-2.64 (m, 2H, CH$_2$), 1.17 (dd, $^3J$=7.5 Hz, $^3J(PH)$=19 Hz, 6H, CH$_3$), 1.01 (dd, $^3J$=7.0 Hz, $^3J(PH)$=18 Hz, 6H, CH$_3$), 0.30 (t, $^3J$=7.0 Hz, 3H, CH$_3$); $^{13}C\{^1H\}$ NMR (125.75 MHz, CD$_3$CN) δ [ppm] 141.3 (d, $^{PC}J$=2.1 Hz), 139.7 (d, $^{PC}J$=4.5 Hz), 133.4, 127.9 (d, $^{PC}J$=3.8 Hz), 123.1, 122.2 (d, $^{PC}J$=2.0 Hz), 52.5 (d, $^{PC}J$=33.9 Hz). 26.9, 20.9 (d, $^{PC}J$=35.1 Hz), 18.3 (d, $^{PC}J$=2.0 Hz), 16.9 (d, $^{PC}J$=1.4 Hz), 18.1 (d, $^{PC}J$=3.4 Hz), 5.4 (d, $^{PC}J$=10.1 Hz); $^{31}P\{^1H\}$ NMR (202.45 MHz, CD$_3$CN) δ [ppm] 42.1; $^{31}P$ NMR (202.45 MHz, CD$_3$CN) δ [ppm] 34.9 (d, $^{PH}J$=470.1 Hz).

(iv) Preparation of BnFluP(nButBu).HBF$_4$ (27a) and EtFluP (nButBu).HBF$_4$ (28a)

BnFluP(nButBu).HBF$_4$ (27a)

To a solution of 9-benzylfluorene (45) (9.24 g, 35.7 mmol) in THF, abs, (75 ml) n-BuLi (13.8 ml, 2.5 M in hexane, 34.7 mmol) was added at −60° C. The solution immediately turned red. After stirring for 1 h at ambient temperature, the reaction mixture was added to a solution of tBuPCl$_2$ (5.2 g 32.7 mmol, dissolved in 50 ml Et$_2$O, abs) at −80° C. At the end of the addition, the red color remained. After stirring over night at ambient temperature, n-BuLi (16.8 ml, 2.5 M in hexane, 41.9 mmol) was added at −60° C. The reaction mixture was stirred for 10 min at −60° C., then for 2 h at ambient temperature. The suspension was filtered over a small pad of Celite® and the clear reddish filtrate was quenched with HBF$_4$.Et$_{20}$ (4.0 ml, 29.3 mmol) to precipitate the phosphonium salt. After separation via suction filtration the crude product was dissolved in acetonitrile (20 ml) and the solution added dropwise to vigorously stirred Et$_2$O (1 l) to obtain a colorless precipitate. Filtration and removal of the volatiles in vacuo afforded 27a as white solid (2.65 g, 17%).

$^1H$ NMR (500 MHz, CD$_3$CN) δ [ppm] 8.19-8.18 (m, 1H, ar), 8.10-8.08 (m, 1H, ar.), 7.78-7.77 (m, 1H, ar), 7.73-7.71 (m, 1H, ar), 7.56-7.50 (m, 4H, ar), 6.93-6.89 (m, 1H, ar), 6.82-6.79 (m, 2H, ar), 6.62-6.60 (m, 2H, ar), 4.09-4.00 (m, 2H, CH$_2$, bn), 2.81-2.77 (m, 1H, CH$_2$, n-Bu), 2.42-2.38 (m, 1H, CH$_2$, n-Bu), 1.95-1.94 (m, 2H, CH$_2$, n-Bu), 1.66-1.59 (m, 2H, CH$_2$, n-Bu), 1.01 (t, $^3J$=7.6 Hz, 3H, CH$_3$, n-Bu), 0.74 (d, $^3J$=17.5 Hz, 9H, CH$_3$, t-Bu); $^{13}C\{^1H\}$ NMR (125.77 MHz, CD$_3$CN) δ [ppm] 141.2 (d, $^{PC}J$=4.5 Hz), 141.0 (d, $^{PC}J$=4.4 Hz), 139.5 (d, $^{PC}J$=2.5 Hz), 138.4 (d, $^{PC}J$=1.9 Hz), 132.0 (d, $^{PC}J$=13.8), 132.1, 131.9, 130.0, 130.0, 129.8, 128.0 (d, $^{PC}J$=6.5 Hz), 127.0, 126.7, 126.4 (d, $^{PC}J$=3.4 Hz), 125.7 (d, $^{PC}J$=2.8 Hz), 121.1, 120.9, 52.1 (d, $^{PC}J$=32.8 Hz), 38.9, 33.5 (d, $^{PC}J$=34.0 Hz), 29.1 (d, $^{PC}J$=7.5 Hz), 25.2, 23.2 (d, $^{PC}J$=14.5 Hz), 14.5 (d, $^{PC}J$=37.7 Hz), 12.3; $^{31}P\{^1H\}$ NMR (202.5 MHz, CD$_3$CN) δ [ppm] 39.8.

EtFluP(nButBu).HBF$_4$ (28a)

9-Ethylfluorene (41) (5.85 g, 30.0 mmol) was dissolved in THF, abs (50 ml), treated with n-BuLi (11.5 ml, 2.5 M in hexane, 29.0 mmol) at −30° C. and stirred for 1 h at ambient temperature. Then tBuPCl$_2$ (4.36 g, 27.4 mmol) dissolved in THF, abs (50 ml) was added at −80° C. to the red solution. The reaction mixture was stirred at ambient temperature for 14 h and the color turned slightly greenish. Completeness of the conversion was checked by $^{31}P$ NMR which showed one single signal at 162.91 ppm (in benzene) for EtFluPtBuCl. At −30° C. n-BuLi (14.0 ml, 2.5 M in hexane, 35.0 mmol) was added and the reaction mixture stirred at ambient temperature overnight. The suspension was filtered over a small pad of Celite® using Schlenk technique. The clear reddish filtrate was treated with $HBF_4.Et_2O$ (5.2 ml, 38 mmol). The volatiles were removed in vacuo to give a yellow residue, which was extracted with chloroform (6 ml), filtered and the clear filtrate added dropwise into $Et_2O$ (200 ml, vigorously stirred) to precipitate the product. Filtration and removal of the volatiles in vacuo afforded 28a (5.3 g, 45%) as a white solid.

$^1H$ NMR (500 MHz, $CDCl_3$) δ [ppm] 7.95 (d, $^3J$=6.5 Hz, 1H, ar), 7.89-7.84 (m, 2H, ar), 7.72 (d, $^3J$=8 Hz, 1H, ar), 7.60-7.49 (m, 4H, ar), 6.77 (d, $^1J$=481 Hz 1H, PH), 2.81-2.73 (m, 1H, $CH_2$ (ethyl)), 2.69-2.61 (m, 1H, $CH_2$ (ethyl)), 2.42-2.32 (m, 1H, $CH_2$ (butyl)), 2.18-2.08 (m, 1H, $CH_2$ (butyl)), 1.88-1.77 (m, 2H, $CH_2$ (butyl)), 1.57-1.43 (m, 2H, $CH_2$ (butyl)), 0.97 (t, $^3J$=7.5 Hz, 3H, (butyl)), 0.85 (d, $^3J(PH)$=17 Hz, 9H, $CH_3$), 0.32 (t, $^3J$=7.5 Hz, 3H, (ethyl)); $^{13}C\{^1H\}$ NMR (125.75 MHz, $CDCl_3$) δ [ppm] 141.7 (d, $^{PC}J$=4.4 Hz), 141.3 (d, $^{PC}J$=4.5 Hz), 139.9, 139.0 (d, $^{PC}J$=2.8 Hz), 130.4, 130.2, 129.3, 128.9, 125.9 (d, $^{PC}J$=3.3 Hz), 124.7 (d, $^{PC}J$=2.3 Hz), 121.4, 121.0, 52.2 (d, $^{PC}J$=34 Hz), 33.7 (d, $^{PC}J$=36.3 Hz), 28.8 (d, $^{PC}J$=5.5 Hz), 28.1, 26.5, 24.1 (d, $^{PC}J$=13.1 Hz), 15.0 (d, $^{PC}J$=37.7 Hz), 13.2, 6.3 (d, $^{PC}J$=9.3 Hz); $^{31}P\{^1H\}$ NMR (202.45 MHz, $CDCl_3$) δ [ppm] 39.4; $^{31}P$ NMR (202.45 MHz, $CDCl_3$) δ [ppm] 39.4 (d, $^{PC}J$=480 Hz).

(v) Preparation of a Monosulfonated Fluorenylphosphine 9-Et-2-$SO_3$H-FluP$Cy_2$.$HBF_4$ (13a)

To a solution of EtFluP$Cy_2$ $HBF_4$ (9a) (2.35 g, 4.92 mmol) in 1 ml of $CH_2Cl_2$, abs, 2.3 ml of concentrated sulfuric acid were added at 0° C. After stirring the solution at 40° C. overnight, 5 g of ice were added. The reaction mixture was extracted with chloroform (3×10 ml). The combined organic layers were dried over $MgSO_4$. After filtration the clear filtrate was reduced to a final volume of 5 ml in vacuo. The concentrate was added dropwise to diethylether (500 ml, vigorously stirred) to precipitate the product. Filtration and removal of the volatiles in vacuo afforded the pure product 13a (1.8 g, 67%) as a white solid.

$^1H$ NMR (500 MHz, methanol-$d_4$) δ [ppm] 8.22 (s, 1H, ar), 8.10 (s, 2H, ar), 8.09 (s, 1H, ar), 7.86 (d, $^3J$=10 Hz, 1H, ar), 7.68 (t, $^3J$=7.5 Hz, 1H, ar), 7.60 (t, $^3J$=7.5 Hz, 1H, ar), 2.87-2.81 (m, 1H, $CH_2$), 2.79-2.74 (m, 1H, $CH_2$), 2.69-2.61 (m, 1H, CH), 2.51-2.46 (m, 1H, CH), 2.05-1.05 (m, 20H, $CH_2$), 0.34 (t, 3J=6.5 Hz, 3H, $CH_3$). $^{13}C\{^1H\}$ NMR (125.75 MHz, methanol-$d_4$) δ [ppm] 147.5, 144.8 (d, $^{PC}J$=4.8 Hz), 142.5 (d, $^{PC}J$=4.5 Hz), 141.8 (d, $^{PC}J$=2.9 Hz), 141.0 (d, $^{PC}J$=2.0 Hz), 131.8, 130.6, 129.4, 126.4 (d, $^{PC}J$=4.0 Hz), 124.0 (d, $^{PC}J$=3.9 Hz), 123.2, 122.4, 53.9 (d, $^{PC}J$=33.7 Hz), 32.4 (d, $^{PC}J$=9.2 Hz), 32.1 (d, $^{PC}J$=8.7 Hz), 30.8 (d, $^{PC}J$=3.8 Hz), 30.4 (d, $^{PC}J$=3.4 Hz), 29.6 (d, $^{PC}J$=4.0 Hz), 29.5 (d, $^{PC}J$=5.4 Hz), 28.9 (d, $^{PC}J$=3.8 Hz), 28.5, 27.7 (d, $^{PC}J$=4.9 Hz), 27.6 (d, $^{PC}J$=4.3 Hz), 27.4 (d, $^{PC}J$=11.3 Hz), 27.2 (d, $^{PC}J$=11.9 Hz), 26.0 (d, $^{PC}J$=2.8 Hz), 6.9 (d, $^{PC}J$=11.7 Hz). $^{31}P\{^1H\}$ NMR (202.46 MHz, methanol-$d_4$) δ [ppm] 34.9.

B. USE OF PHOSPHINE COMPOUNDS IN CROSS COUPLING REACTIONS

Some of the synthesized phosphine compounds were used as ligands in Pd complexes performing as catalysts in various cross-coupling reactions. All cross-coupling reaction were carried out under an argon atmosphere in degassed solvents (freeze and thaw). TON means catalytic turnover number and is defined as the ratio of the number of moles of product to the number of moles of catalyst.

I. Sonogoshira Coupling Reactions (i) Sonogashira Coupling of Aryl Bromides (in Diisopropylamine)

Dry diisopropylamine (10 ml), arylbromide (10 mmol) and acetylene (11 mmol) were placed in a Schlenk tube. Then the catalyst was added in the given concentration as a ready-made mixture of $Na_2PdCl_4$/ligand (phosphonium salt)/CuI (4:8:3) under argon. Unless otherwise noted the reaction mixture was stirred at 50° C. in an aluminum block. After cooling to room temperature the reaction mixture was diluted with ether (15 ml), washed with water (10 ml), the organic phase dried over $MgSO_4$, filtered and concentrated in vacuo. The product was isolated by column chromatography (silica, cyclohexane/ethylacetate (100:2). Alternatively the yield was either determined via gas chromatography with hexadecane or diethylene glycol di-n-butylether as an internal standard or by determination of the mass of the isolated $iPr_2NH_2^+Br^-$.

TABLE 1

Primary Sonogashira screen for the reaction of phenylacetylene and 4-bromotoluene utilizing various phosphine compounds

| Ligand | TON[a] |
| --- | --- |
| $C_{18}H_{37}$FluP$Cy_2$ (11) | 5900 |
| EtFluP$Cy_2$ (9a) | 5600 |
| MeFluP$Cy_2$ (8a) | 5600 |
| $C_{18}H_{37}$FluP$iPr_2$ (7a) | 5500 |
| $Ad_2$PBn* | 3600 |
| MeFluP$iPr_2$ (5a) | 3500 |
| EtFluP$iPr_2$ (6a) | 3200 |
| 9-Et-1-MeFluP$Cy_2$ (12a) | 2600 |
| iPrFluP$Cy_2$ (22a) | 906 |
| Et-1,3,8-$Me_3$FluP$Cy_2$ (29a) | 850 |
| iPrFluP$iPr_2$ (23a) | 500 |
| HFluP$tBu_2$ (25a) | 330 |
| PhFluP$iPr_2$ (30a) | 250 |

Reagents and conditions: 10 mmol 4-bromotoluene, 11 mmol phenylacetylene, 10 ml $iPr_2$NH, 50° C., 24 h. Catalyst: $Na_2PdCl_4$/ligand/CuI (4:8:3), catalyst mixture in $iPr_2NH_2Br$, max. TON=15000.
[a] Average of two runs. Determined by the mass of the isolated ammonia salt.

Comparative Example $Ad_2$PBn is an adamantly-substituted phosphine and is available under the trademark Catacxium® A from Degussa AG.

TABLE 2

Sonogashira coupling of various aryl bromides with phenylacetylene using EtFluPCy$_2$·HBF$_4$

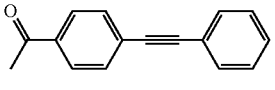

| Run | Aryl bromide | Product | t (h) | Yield[a] |
|---|---|---|---|---|
| 1 | 4-bromoacetophenone | 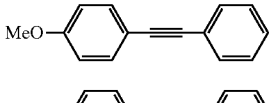 | 3 | ≥99 |
| 2 | 4-bromoanisol | 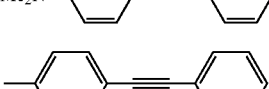 | 24 | ≥99 |
| 3 | 4-bromo-dimethylaniline | 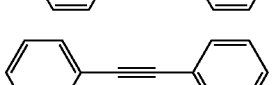 | 24 | ≥99 |
| 4 | 4-bromotoluene | 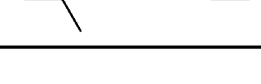 | 24 | ≥99 |
| 5 | 2-bromotoluene |  | 24 | 95 |

Reagents and conditions: 10 mmol aryl bromide, 11 mmol phenylacetylene, 10 ml iPr$_2$NH, 50° C., 24 h. Catalyst: 0.02 mol % Na$_2$PdCl$_4$, 0.04 mol % EtFluPCy$_2$·HBF$_4$ (9a), 0.015 mol % CuI, catalyst mixture in iPr$_2$NH$_2$Br.

[a] Average of two runs, determined by GC (hexadecane as internal standard) and by the mass of the isolated ammonium salt. Both analytical methods gave similar results.

TABLE 3

Sonogashira-coupling of aryl bromides. Determination of TON using various phosphine ligands

| Run | Aryl bromide | Acetylene | Ligand[a] | mol % Pd | t (h) | Yield[b] | TON |
|---|---|---|---|---|---|---|---|
| 1 | bromobenzene | phenylacetylene | 5 | 0.0033 | 16 | 81% | 24300 |
| 2 | bromobenzene | phenylacetylene | 6 | 0.0033 | 16 | 88% | 26400 |
| 3 | 2-bromotoluene | phenylacetylene | 5 | 0.0033 | 16 | 83% | 24900 |
| 4 | 2-bromo-m-xylene | phenylacetylene | 5 | 0.0067 | 16 | 57% | 8550 |
| 5 | 2-bromobenzotrifluoride | phenylacetylene | 6 | 0.0033 | 16 | 51% | 15300 |
| 6 | 4-bromoanisol | phenylacetylene | 5 | 0.0033 | 20 | 41% | 23300 |
| 7 | 4-bromoanisol | phenylacetylene | 6 | 0.0033 | 20 | 84% | 25200 |

Reagents and conditions: 10 mmol aryl bromide, 11 mmol acetylene, 10 ml HNiPr$_2$, 80° C., 24 h. Catalyst: Na$_2$PdCl$_4$/phosphonium salt/CuI (4:8:3), catalyst mixture in iPr$_2$NH·HBr.
[a] 5: MeFluPiPr$_2$; 6: EtFluPiPr$_2$
[b] Average of 2 runs.

(ii) Sonogashira Coupling of Aryl Chlorides (in DMSO)

Dry DMSO (5 ml, crown cap), aryl chloride (1.5 mmol), acetylene (2.1 mmol) and Na$_2$CO$_3$ (3 mmol) were placed in a Schlenk tube. Then the catalyst was added in the given concentration, Na$_2$PdCl$_4$/ligand (phosphonium salt)/CuI (4:8:3) under argon. The reaction mixture was stirred at 100-120° C. in an aluminum block for 12 to 20 h. After cooling to room temperature the reaction mixture was diluted with ether (15 ml), washed with water (10 ml), the organic phase dried over MgSO$_4$, filtered and concentrated in vacuo. The product was isolated by column chromatography (silica, cyclohexane/ethylacetate (100:2). Alternatively the yield was determined via gaschromatography with hexadecane or diethylene glycol di-n-butylether as an internal standard.

TABLE 4

Sonogashira reactions with aryl chlorides

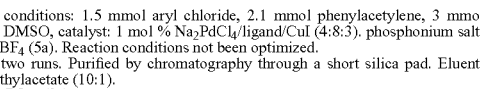

| Run | Aryl chloride | T (° C.) | t (h) | yield[a] |
|---|---|---|---|---|
| 1 | 4-chloroanisol | 110 | 16 h | 43% 44%[b] 47%[c] 23%[d] |
| 2 | 4-nitrochlorobenzene | 100 | 12 | 88% |
| 3 | 4-chloroacetophenone | 100 | 12 | 94% |
| 4 | 4-CF$_3$-chlorobenzene | 100 | 12 | 92% |
| 5 | chlorobenzene | 120 | 16 | 87% |
| 6 | 4-chlorotoluene | 120 | 16 | 91% |
| 7 | 4-chloroanisol | 120 | 20 | 73% |

Reagents and conditions: 1.5 mmol aryl chloride, 2.1 mmol phenylacetylene, 3 mmol Na$_2$CO$_3$, 5 ml DMSO, catalyst: 1 mol % Na$_2$PdCl$_4$/ligand/CuI (4:8:3). phosphonium salt: MeFluPiPr$_2$·HBF$_4$ (5a). Reaction conditions not been optimized.
[a] Average of two runs. Purified by chromatography through a short silica pad. Eluent: cyclohexane:ethylacetate (10:1).
[b] ligand: EtFluPCy$_2$ (9a).
[c] ligand: BnFluPCy$_2$ (10a).
[d] ligand: Ad$_2$PBn (comparative example).

(iii) Sonogashira Coupling of Aryl Bromides (in Water)

Preparation of the catalyst stock solution: $Na_2PdCl_4$ (0.05 mmol), 9-Et-2-$SO_3$HFlu-$PCy_2 \cdot HBF_4$ (13a) (0.1 mmol) and $Cs_2CO_3$ (0.4 mmol) were placed in a Schlenk tube under argon. Degassed water (5.0 ml) was added and the mixture was stirred at 45° C. for 2 h until the solution turns off white. The stock solution has a concentration of 1 mol %/(ml mmol aryl halide).

Cross-coupling reaction: The arylbromide (1 mmol), acetylene (1.1 mmol) and $Cs_2CO_3$ (2 mmol) were charged into a in Schlenk tube and water (2 ml) and isopropanol (2 ml) as well as the catalyst stock solution were added. The reaction mixture was stirred at 100° C. in an aluminum block for 1.5 to 4 h. After cooling to room temperature the reaction mixture was diluted with ether (15 ml), washed with water (10 ml), the organic phase was dried over $MgSO_4$, filtered and concentrated in vacuo. The product was isolated by column chromatography (silica, cyclohexane/ethylacetate (100:2). Alternatively the yield was determined via gaschromatography with hexadecane or diethylene glycol di-n-butylether as an internal standard.

II. Suzuki Coupling Reactions

(i) Suzuki Reaction of Aryl Halides (in Dioxane)

Preparation of the catalyst stock solution: $Na_2PdCl_4$ (0.05 mmol), phosphonium salt (0.1 mmol) and $Cs_2CO_3$ (0.2 mmol) were placed in a Schlenk tube. Dioxane (5.0 ml) was added and the mixture was stirred at 45° C. for 2 h until the solution turns off white. The so prepared stock solution has a concentration of 1 mol %/(ml*mmol aryl halide). Cross-coupling reaction: Dioxane (5 ml) and the catalyst stock solution were added to the aryl halide (1 mmol), boronic acid (1.5 mmol) and $Cs_2CO_3$ (2 mmol). The reaction mixture was stirred at 100° C. in an aluminum block. After cooling to room temperature the reaction mixture was diluted with ether (15 ml), washed with water (10 ml), the organic phase was dried over $MgSO_4$, filtered and concentrated in vacuo. The product was isolated by column chromatography (silica, cyclohexane/ethylacetate (100:2). Alternatively the yield was determined via gaschromatography with hexadecane or diethylene glycol di-n-butylether as an internal standard.

TABLE 5

Sonogashira reaction of aryl bromides in an aqueous system

| Run | Aryl bromide | Acetylene | Product | t (h) | Conversion[a] | Yield[b] |
|---|---|---|---|---|---|---|
| 1 | 4-acetylphenyl bromide | phenylacetylene | 4-acetyl-diphenylacetylene | 1 h | ≥99% | 97% |
| 2 | bromobenzene | phenylacetylene | diphenylacetylene | 1.5 h | ≥99% | 98% |
| 3 | 4-methoxyphenyl bromide | phenylacetylene | 4-methoxy-diphenylacetylene | 2 h | ≥99% | 95% |
| 4 | 2,6-dimethylphenyl bromide | phenylacetylene | 2,6-dimethyl-diphenylacetylene | 4 h | ≥99% | 95% |
| 5 | 2,6-dimethylphenyl bromide | tert-butylacetylene | 2,6-dimethylphenyl-tert-butylacetylene | 4 h | ≥99% | 94% |
| 6 | 4-acetylphenyl bromide | tert-butylacetylene | 4-acetylphenyl-tert-butylacetylene | 4 h | ≥99% | 95% |

Reagents and conditions: 1 mmol aryl bromide, 1.2 mmol acetylene, 1.5 mmol $Cs_2CO_3$, 1 mol % $Na_2PdCl_4$, 2 mol % ligand ((9-ethyl-2-sulfofluorenyl)dicyclohexyl-phosphonium-tetrafluoroborate; 9-Et-2-$SO_3$HFluP$Cy_2$ (13)), H2O/i-propanol (4 ml, 1:1), 100° C. Reaction times and temperatures were not optimized.
[a] Average of 2 runs, determined by GC using hexadecane as internal standard.
[b] Average of 2 runs. Purified by chromatography, eluents: cyclohexane:ethylacetate (10:1).

TABLE 6

Suzuki reaction with aryl chlorides, ligand-screening

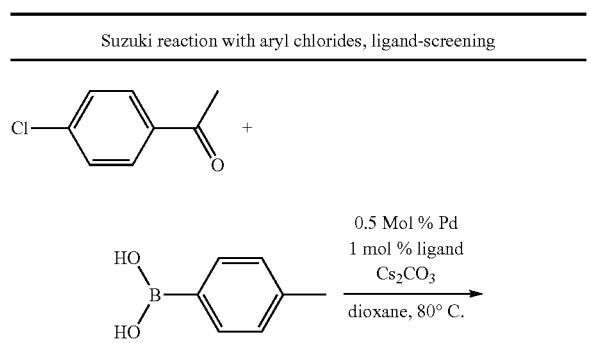

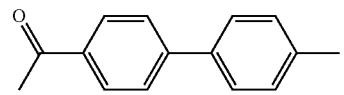 [SMILES: CC(=O)c1ccc(-c2ccc(C)cc2)cc1]

| Run | Ligand | mol % catalyst[a] | Conversion[b] |
|-----|--------|-------------------|---------------|
| 1 | EtFluPCy$_2$ (9) | 0.5 | 77% |
| 2 | BnFluPCy$_2$ (10) | 0.5 | 13% |
| 3 | iPrFluPCy$_2$ (22) | 0.5 | 5% |
| 4 | MeFluPiPr$_2$ (5) | 0.5 | 21% |

Reagents and conditions: 1 mmol aryl chloride, 1.5 boronic acid, 2.0 mmol Cs$_2$CO$_3$, dioxane (5 ml), 80° C., 12 h.
[a]Na$_2$PdCl$_4$/ligand (1:2)
[b]Average of 2 runs, determined by GC using hexadecane as internal standard.

TABLE 7

Suzuki reaction with aryl chlorides using EtFluPCy$_2$ · HBF$_4$ (9a) and BnFluPiPr$_2$ · HBF$_4$ (26a)

| Run | Aryl chloride | Boronic acid | Product | Ligand[a] | mol % catalyst[b] | t(h) | Conversion[c] |
|-----|---------------|--------------|---------|-----------|-------------------|------|---------------|
| 1 | 2-Cl acetophenone | 4-Me-C$_6$H$_4$-B(OH)$_2$ | 2-acetyl-4'-methylbiphenyl | 9 | 0.5 / 0.05 | 2 h / 24 h | ≥99% / ≥99% |
| 2 | 2-Cl fluorobenzene | 4-Me-C$_6$H$_4$-B(OH)$_2$ | 2-fluoro-4'-methylbiphenyl | 9 | 0.5 / 0.05 | 2 h / 24 h | ≥99% / ≥99% |
| 3 | 2-Cl benzophenone | 4-Me-C$_6$H$_4$-B(OH)$_2$ | 2-benzoyl-4'-methylbiphenyl | 9 | 0.5 / 0.05 | 2 h / 24 h | ≥99% / ≥99% |
| 4 | 4-Cl anisole | 4-Me-C$_6$H$_4$-B(OH)$_2$ | 4-methoxy-4'-methylbiphenyl | 9 | 0.5 / 0.1 / 0.05 | 5 h / 20 h / 24 h | ≥99% / ≥99% / 65% |
| 5 | 2-Cl toluene | 1-naphthyl-B(OH)$_2$ | 1-(2-methylphenyl)naphthalene | 9 | 0.5 / 0.05 | 5 h / 24 h | ≥99% / ≥99% |

TABLE 7-continued

Suzuki reaction with aryl chlorides using EtFluPCy$_2$ · HBF$_4$ (9a) and BnFluPiPr$_2$ · HBF$_4$ (26a)

| Run | Aryl chloride | Boronic acid | Product | Ligand[a] | mol % catalyst[b] | t(h) | Conversion[c] |
|---|---|---|---|---|---|---|---|
| 6 | 2-Cl-acetophenone | 4-methylphenylboronic acid | 2'-acetyl-4-methylbiphenyl | 26 | 1<br>0.1 | 1 h<br>12 h | ≥99%<br>≥99% |
| 7 | 3-chlorotoluene | 4-methylphenylboronic acid | 3-methyl-4'-methylbiphenyl | 26 | 1<br>0.1 | 1.5 h<br>12 h | ≥99%<br>≥99% |
| 8 | 2-chlorobenzophenone | 4-methylphenylboronic acid | product | 26 | 1<br>0.1 | 1.5 h<br>12 h | ≥99%<br>≥99% |
| 9 | 4-chloroanisole | 4-methylphenylboronic acid | 4-methoxy-4'-methylbiphenyl | 26 | 1<br>0.3<br>0.1 | 4 h<br>12 h<br>12 h | ≥99%<br>≥99%<br>81% |
| 10 | 2-chlorotoluene | 1-naphthylboronic acid | product | 26 | 1<br>0.2 | 4<br>12 | ≥99%<br>≥99% |

Reagents and conditions: 1 mmol aryl chloride, 1.5 boronic acid, 2.0 mmol Cs$_2$CO$_3$, dioxane (5 ml), 100° C., reaction conditions and the amount of catalyst have not been optimized.
[a]ligand: 9: EtFluPCy$_2$; 26: BnFluPiPr$_2$
[b]catalyst: Na$_2$PdCl$_4$/ligand (1:2)
[c]Average of two runs, determined by GC using hexadecane as internal standard.

(ii) Suzuki Reaction of Aryl Halides (in Water)

Preparation of the catalyst-stock-solution: The catalyst stock solution was prepared as described for the aqueous Sonogshira reaction using 9-Et-2-SO$_3$HFlu-PCy$_2$.HBF$_4$ (13a). Cross-coupling reaction: Aryl halide (1 mmol), boronic acid (1.2 mmol) and K$_2$CO$_3$ (3.2 mmol) were first added to water (4 ml), then the catalyst stock solution and two drops of Labrasol® (caprylocaproyl macrogol-8 glyceride blend, saturated polyglycolized glycerides consisting of mono-, di- and triglycerides of mono- and di-fatty acids of polyethylene glycol (PEG)) were added. The reaction mixture was stirred at the respective temperatures (see Table 8) for 0.5-20 h (see Table 8). After cooling to room temperature the reaction mixture was diluted with ether (15 ml), washed with water (10 ml), the organic phase was dried over MgSO$_4$, filtered and concentrated in vacuo. The product was isolated by column chromatography (silica, cyclohexane/ethylacetate (100:2). Alternatively the yield was determined via gas chromatography with hexadecane or diethylene glycol di-n-butylether as an internal standard.

TABLE 8

Suzuki coupling of aryl bromides and aryl chlorides in water

| Run | Halide | Boronic acid | Product | Pd [mol %] | Conditions | Yield [%][/] |
|-----|--------|--------------|---------|------------|------------|--------------|
| 1 | Br–C6H4–NO2 | 4-MeC6H4–B(OH)2 | O2N–C6H4–C6H4–Me | 0.1 / 0.01 / 0.005 | RT, 20 h / 100° C., 2 h / 100° C., 3.5 h | ≥99% / ≥99% / ≥99% |
| 2 | 2-bromoacetophenone | 4-MeC6H4–B(OH)2 | 3-acetyl-4'-methylbiphenyl | 0.5 / 0.5 | 90° C., 45 min / 90° C., 30 min[a] | ≥99% / ≥99% |
| 3 | 2-ethylbromobenzene | 4-MeC6H4–B(OH)2 | 2-ethyl-4'-methylbiphenyl | 0.5 | 50° C., 1.5 h | ≥99% |
| 4 | 2-isopropylbromobenzene | 4-MeC6H4–B(OH)2 | 2-isopropyl-4'-methylbiphenyl | 0.5 | 50° C., 4 h | ≥99% |
| 5 | 3-bromo-N,N-dimethylaniline | 4-MeC6H4–B(OH)2 | 3-(dimethylamino)-4'-methylbiphenyl | 0.5 | 50° C., 1.5 h | ≥99% |
| 6 | 2,6-dimethylbromobenzene | 4-MeC6H4–B(OH)2 | 2,6-dimethyl-4'-methylbiphenyl | 1 | RT, 20 h | ≥99% |
| 7 | 4-bromoaniline | 4-MeC6H4–B(OH)2 | 4-amino-4'-methylbiphenyl | 0.25 / 0.1 / 0.1 | RT, 3 h / RT, 2.5 h / RT, 2.5 h[a] | ≥99% / 50% / 66% |
| 8 | 2-isopropylbromobenzene | 1-naphthylboronic acid | 1-(2-isopropylphenyl)naphthalene | 1 | 100° C., 20 h | ≥99% |
| 9 | 4-bromoaniline | 1-naphthylboronic acid | 4-(1-naphthyl)aniline | 0.5 | 65° C., 20 h | ≥99% |

TABLE 8-continued

Suzuki coupling of aryl bromides and aryl chlorides in water

| Run | Halide | Boronic acid | Product | Pd [mol %] | Conditions | Yield [%][f] |
|---|---|---|---|---|---|---|
| 10 | 2,6-dimethylbromobenzene | 1-naphthaleneboronic acid | 2,6-dimethyl-1-(naphthalen-1-yl)benzene | 1 | 90° C., 20 h | ≥99% |
| 11 | 4-chlorobenzonitrile | 4-methylphenylboronic acid | 4'-methyl-[1,1'-biphenyl]-4-carbonitrile | 0.05 | 100° C., 2 h | ≥99% |
| | | | | 0.1 | 100° C., 30 min | ≥99% |
| | | | | 1 | 40° C., 10 h | ≥99% |
| | | | | 1 | RT, 20 h[a] | ≥99% |
| | | | | 0.1 | 100° C., 45 min[b] | ≥99% |
| | | | | 0.1 | 100° C., 1 h[c] | ≥99% |
| | | | | 0.1 | 100° C., 1 h[d] | ≥99% |
| | | | | 0.1 | 100° C., 25 min[e] | ≥99% |
| 12 | 2-chlorobenzophenone | 4-methylphenylboronic acid | (4'-methyl-[1,1'-biphenyl]-2-yl)(phenyl)methanone | 0.5 | 90° C., 4 h | 92% |
| | | | | 0.5 | 90° C., 4 h[a] | 98% |
| 13 | chlorobenzene | 4-methylphenylboronic acid | 4-methylbiphenyl | 0.5 | 100° C., 2 h | ≥99% |
| | | | | 1 | RT, 20 h[a] | ≥99% |
| 14 | 3-chlorobenzamide | 4-methylphenylboronic acid | 4'-methyl-[1,1'-biphenyl]-3-carboxamide | 0.5 | 100° C., 2.5 h[a] | ≥99% |
| | | | | 1 | RT, 20 h[a] | ≥99% |
| 15 | 4-chlorotoluene | 4-methylphenylboronic acid | 4,4'-dimethylbiphenyl | 0.5 | 100° C., 90 min | ≥99% |
| 16 | 4-chlorobenzenesulfonamide | 4-methylphenylboronic acid | 4'-methyl-[1,1'-biphenyl]-4-sulfonamide | 1 | 100° C., 24 h | ≥99% |

TABLE 8-continued

Suzuki coupling of aryl bromides and aryl chlorides in water

| Run | Halide | Boronic acid | Product | Pd [mol %] | Conditions | Yield [%][/] |
|---|---|---|---|---|---|---|
| 7 | 2-chlorobenzaldehyde | 4-methylphenylboronic acid | 4'-methyl-2-biphenylcarbaldehyde | 1 / 0.5 | 90° C., 30 min / RT, 4 h | ≥99% / ≥99% |
| 18 | 4-chloroaniline | 4-methylphenylboronic acid | 4'-methyl-4-aminobiphenyl | 0.5 | 90° C., 20 h | 74% |
| 19 | 4-chlorobenzonitrile | 1-naphthylboronic acid | 4-(naphthalen-1-yl)benzonitrile | 0.5 | 65° C., 20 h | 80% |
| 20 | 4-chlorobenzenesulfonamide | 1-naphthylboronic acid | 4-(naphthalen-1-yl)benzenesulfonamide | 0.5 | 90° C., 20 h | ≥99% |
| 21 | 2-chloropyridine | 4-methylphenylboronic acid | 2-(4-methylphenyl)pyridine | 0.5 | 100° C., 12 h[a] | ≥99% |
| 22 | 4-amino-2-chloropyridine | 4-methylphenylboronic acid | 4-amino-2-(4-methylphenyl)pyridine | 0.5 | 100° C., 12 h[a] | ≥99% |
| 23 | 4-amino-2-chloropyridine | 1-naphthylboronic acid | 4-amino-2-(naphthalen-1-yl)pyridine | 0.5 | 100° C., 12 h[a] | ≥99% |
| 24 | bromobenzene | 3-pyridylboronic acid | 3-phenylpyridine | 0.1 | 100° C., 12 h[a] | ≥99% |
| 25 | chlorobenzene | 3-pyridylboronic acid | 3-phenylpyridine | 0.5 | 100° C., 12 h[a] | ≥99% |
| 26 | 2-chlorobenzotrifluoride | 3-pyridylboronic acid | 3-(2-trifluoromethylphenyl)pyridine | 0.1 | 100° C., 12 h[a] | ≥99% |

TABLE 8-continued

Suzuki coupling of aryl bromides and aryl chlorides in water

| Run | Halide | Boronic acid | Product | Pd [mol %] | Conditions | Yield [%][f] |
|---|---|---|---|---|---|---|
| 27 | 2-chloropyridine | pyridin-3-ylboronic acid | 2,3'-bipyridine | 0.5 | 100° C., 12 h[a] | ≥99% |
| 28 | 4-amino-2-chloropyridine | pyridin-3-ylboronic acid | 4-amino-2,3'-bipyridine | 0.5 | 100° C., 20 h[a] | ≥99% |
|  |  |  |  | 0.1 | 100° C., 20 h[a] | 43% |
| 29 | 2-chloro-1,3-dimethylbenzene | (4-methylphenyl)boronic acid | 2,6-dimethyl-4'-methylbiphenyl | 1 | 100° C., 24 h[a] | 97 |
| 30 | 2-chloro-1,3-dimethylbenzene | naphthalen-1-ylboronic acid | 1-(2,6-dimethylphenyl)naphthalene | 1 | 100° C., 24 h[a] | 96 |
| 31 | 2-chloro-1,3-dimethylbenzene | naphthalen-1-ylboronic acid | 1-(2,6-dimethylphenyl)naphthalene | 0.5 | 100° C., 24 h[a] | 90 |

General reaction conditions: 1.0 equiv. aryl halide, 1.2 equiv. boronic acid, 3.2 equiv. $K_2CO_3$, degassed water (4 ml mmol$^{-1}$), catalyst: $Na_2PdCl_4$/ligand (1:2), ligand: 9-Et-2-$SO_3$HFluPCy$_2$ (13). Reaction times and temperatures were not optimized.
[a] Additive: Labrasol (0.05 ml).
[b] 1 equiv. aryl halide, 1.2 equiv. boronic acid, 3.2 equiv. $CsCO_3$.
[c] 1 equiv. aryl halide, 1.2 equiv. boronic acid, 3.2 equiv. KF.
[d] 1 equiv. aryl halide, 1.2 equiv. boronic acid, 3.2 equiv. NaOH.
[e] 1 equiv. aryl halide, 1.2 equiv. boronic acid, 3.2 equiv. $K_3PO_4$.
[f] Average of two runs, determined by GC using hexadecane as internal standard.

III. Buchwald-Hartwig Amination of Aryl Halides 5 ml dry toluene, 5 mmol aryl halide, 6 mmol amine and 6 mmol NaOtBu were placed in a Schlenk tube. Next the catalyst $Na_2PdCl_4$/EtFluPCy$_2$ (9) (as phosphonium salt (9a)) (1:2) was added in the given concentration. The reaction mixture was stirred at 120° C. in an aluminum block. After cooling to room temperature the reaction mixture was diluted with ether (15 ml), washed with water (10 ml), the organic phase dried over $MgSO_4$, filtered and concentrated in vacuo. The product was isolated by column chromatography (silica, cyclohexane/ethylacetate (90:10). Alternatively the yield was determined via gaschromatography with hexadecane or diethylene glycol di-n-butylether as an internal standard.

TABLE 9

Buchwald-Hartwig amination of aryl bromides and chlorides.

$$\text{R}\!-\!\!\bigcirc\!\!-\!\text{X} + \text{HNR}_1\text{R}_2 \xrightarrow[\text{toluene, 120° C.}]{\substack{0.5\% \text{ Pd(OAc)}_2, \\ 1.0\% \text{ Ligand} \\ \text{NaOtBu}}} \text{R}\!-\!\!\bigcirc\!\!-\!\text{NR}_1\text{R}_2$$

| Entry | Aryl halide | Amine | Product | mol % catalyst | t (h) | Conversion[a] |
|-------|-------------|-------|---------|----------------|-------|---------------|
| 1 | 4-chlorotoluene | 3,5-dimethylaniline | N-(3,5-dimethylphenyl)-4-methylaniline | 0.5 | 12 | 16% |
| 2 | 3-bromoacetophenone | aniline | 4-(phenylamino)acetophenone | 0.1 | 3 | ≥99% |
| 3 | 4-bromotoluene | 3,5-dimethylaniline | N-(3,5-dimethylphenyl)-4-methylaniline | 0.5 | 2 | ≥99% |
| 4 | 4-bromotoluene | morpholine | 4-(4-methylphenyl)morpholine | 0.5 | 2 | ≥99% |
| 5 | 2-bromo-1,3-dimethylbenzene | morpholine | 4-(2,6-dimethylphenyl)morpholine | 0.5 | 6 | 91% |
| 6 | 4-bromobenzotrifluoride | α-methylbenzylamine | N-(1-phenylethyl)-4-(trifluoromethyl)aniline | 0.25 | 2 | ≥99% |
| 7 | 4-bromotoluene | α-methylbenzylamine | 4-methyl-N-(1-phenylethyl)aniline | 0.5 | 2 | ≥99% |
| 8 | 4'-chloroacetophenone | aniline | 4'-(phenylamino)acetophenone | 0.5 | 12 | ≥99% |

TABLE 9-continued

Buchwald-Hartwig amination of aryl bromides and chlorides.

$$R\text{-}C_6H_4\text{-}X + HNR_1R_2 \xrightarrow[\text{toluene, 120° C.}]{\substack{0.5\% \text{ Pd(OAc)}_2, \\ 1.0\% \text{ Ligand} \\ \text{NaOtBu}}} R\text{-}C_6H_4\text{-}NR_1R_2$$

| Entry | Aryl halide | Amine | Product | mol % catalyst | t (h) | Conversion[a] |
|---|---|---|---|---|---|---|
| 9 | PhCl | 3,5-dimethylaniline | 3,5-Me₂C₆H₃-NH-Ph | 0.5 | 12 | ≥99% |
| 10 | 2-Cl-benzonitrile | morpholine | 2-(morpholino)benzonitrile | 0.5 | 12 | 48% |

Reagents and conditions: 5 ml toluene, 5 mmol aryl halide, 6 mmol amine, 6 mmol NaOtBu, Pd(OAc)₂/ligand (1:2), phosphonium salt: EtFluPCy₂.HBF₄ (9a), 120° C., reaction conditions have not been optimized.
[a] Average of two runs, determined by GC using hexadecane as internal standard.

IV. Carbonylation Reactions

(i) Alkoxycarbonylation Reactions of Different Aryl Bromides Using Different Phosphonium Salts 0.0025 mmol Pd(OAc)₂, 0.0075 mmol ligand (phosphonium salt) and 0.385 mmol TMEDA were diluted with n-butanol to a total volume of 10 ml. 0.5 mmol of each substrate was introduced directly in the autoclaves, and then 1 ml of the catalyst solution was added to the autoclave. After purging with carbon monoxide the pressure was set to 25 bar CO and the autoclave was stirred while warming up to 115° C. The reactions were hold at 115° C. for 20 h. After cooling down and releasing the pressure the raw mixtures were filtered through a short path of Al₂O₃ and the conversion was determined via GC.

TABLE 10

Carbonylation reactions of aryl bromides in n-butanol $$R\text{-}C_6H_4\text{-}Br \xrightarrow[\substack{\text{n-Butanol, TMEDA} \\ 0.5\% \text{ Pd(OAc)}_2, \\ 1.5\% \text{ Ligand}}]{\substack{25 \text{ bar CO,} \\ 115° \text{ C., 20 h}}} R\text{-}C_6H_4\text{-}C(O)O\text{-}nBu$$

| Run | Ligand | Substrate | Conversion (%) |
|---|---|---|---|
| 1 | MeFluPCy₂ (8) | Ethyl 4-bromobenzoate | 95 |
| 2 | MeFluPiPr₂ (5) | Ethyl 4-bromobenzoate | 97 |
| 3 | EtFluPiPr₂ (6) | Ethyl 4-bromobenzoate | 95 |
| 4 | EtFluPCy₂ (9) | Ethyl 4-bromobenzoate | 97 |
| 5 | iPrFluPiPr₂ (23) | Ethyl 4-bromobenzoate | 80 |
| 6 | iPrFluPCy₂ (22) | Ethyl 4-bromobenzoate | 92 |
| 7 | Cp*PCy₂ (14) | Ethyl 4-bromobenzoate | 14 |
| 8 | C₁₈H₂₇FluPCy₂ (11) | Ethyl 4-bromobenzoate | 34 |
| 9 | EtFluP(nButBu) (28) | Ethyl 4-bromobenzoate | 31 |
| 10 | EtMeFluPCy₂ (12) | Ethyl 4-bromobenzoate | 18 |
| 11 | Me₃InPCy₂ (16) | 3-Br-Acetophenone | 66 |
| 12 | Me₃InPCy₂ (16) | 4-Br-Acetophenone | 85 |
| 13 | Me₃InPCy₂ (16) | 2-Br-Benzonitrile | 94 |
| 14 | Me₃InPCy₂ (16) | 2-Br-Pyridine | 99 |
| 15 | Me₃InPCy₂ (16) | 2-Br-Thiophene | 82 |
| 16 | BnFluPCy₂ (10) | 4-Br-2Cl-Toluene | 75 |
| 17 | BnFluPCy₂ (10) | 3-Br-Anisol | 65 |
| 18 | BnFluPCy₂ (10) | 3-Br-Acetophenone | 95 |
| 19 | BnFluPCy₂ (10) | 4-Br-Acetophenone | 95 |
| 20 | BnFluPCy₂ (10) | 2-Br-Benzonitrile | 98 |
| 21 | BnFluPCy₂ (10) | 3-Br-Pyridine | 98 |
| 22 | BnFluPCy₂ (10) | 2-Br-Pyridine | 100 |
| 23 | BnFluPCy₂ (10) | 2-Br-Thiophene | 62 |
| 24 | BnFluPCy₂ (10) | 3-Br-Thianaphtene | 78 |
| 25 | Me₃InPiPr₂ (17) | 2-Br-Benzonitrile | 90 |
| 26 | Me₃InPiPr₂ (17) | 2-Br-Pyridine | 98 |
| 27 | Me₃InPiPr₂ (17) | 2-Br-Thiophene | 82 |
| 28 | Me₅InPiPr₂ (19) | 2-Br-Pyridine | 67 |

TABLE 10-continued

Carbonylation reactions of aryl bromides in n-butanol

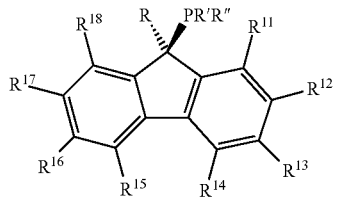

| Run | Ligand | Substrate | Conversion (%) |
|---|---|---|---|
| 29 | Me₅InPCy₂ (18) | 2-Br-Pyridine | 74 |
| 30 | Cp*PiPr₂ (15) | 2-Br-Pyridine | 60 |

(ii) Reductive Carbonylation of Ethyl 4-Bromobenzoate Using Different Phosphonium Salts 0.0025 mmol Pd(OAc)₂, 0.0075 mmol ligand (phosphonium salts) and 0.385 mmol TMEDA were diluted in toluene to a total volume of 10 ml. 0.5 mmol of ethyl 4-bromobenzoate was introduced directly in the autoclaves, and then 1 ml of the catalyst solution was added to the autoclave. After purging with synthesis gas (CO/H₂ 1:1), the pressure was set to 25 bar CO/H₂ and the autoclave was stirred while warming up to 115° C. The reactions were hold at 115° C. for 20 h. After cooling down and releasing the pressure the raw mixtures were filtered through a short path of Al₂O₃ and the conversion was determined via GC.

TABLE 11

Reductive carbonylation reactions of ethyl 4-bromobenzoate.

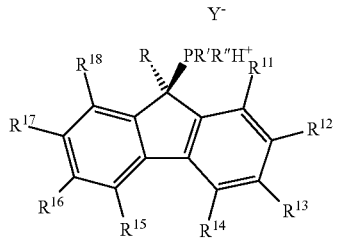

| Run | Ligand | Conversion (%) |
|---|---|---|
| 1 | MeFluPCy₂ (8) | 83 |
| 2 | MeFluPiPr₂ (5) | 18 |
| 3 | EtFluPiPr₂ (6) | 30 |
| 4 | EtFluPCy₂ (9) | 34 |
| 5 | iPrFluPCy₂ (22) | 16 |
| 6 | Cp*PCy₂ (14) | 30 |
| 7 | C₁₈H₃₇FluPCy₂ (11) | 38 |
| 8 | EtFluP (nButBu) (28) | 38 |
| 9 | EtMeFluPCy₂ (12) | 13 |

The invention claimed is:

1. A phosphine compound represented by the general formula (4):

(4)

$$\text{[Structure with } R^{18}, R, PR'R'', R^{11}, R^{17}, R^{12}, R^{16}, R^{15}, R^{14}, R^{13}\text{]}$$

or its corresponding phosphonium salt represented by the general formula (4a):

(4a)

$$Y^-$$

$$\text{[Structure with } R^{18}, R, PR'R''H^+, R^{11}, R^{17}, R^{12}, R^{16}, R^{15}, R^{14}, R^{13}\text{]}$$

wherein
R' and R" are each independently selected from alkyl, cycloalkyl and 2-furyl radicals, or R' and R" are joined together to form with the phosphorous atom a carbon-phosphorous monocycle comprising at least 3 carbon atoms or a carbon-phosphorous bicycle; the alkyl radicals, cycloalkyl radicals, and carbon-phosphorous monocycle being unsubstituted or substituted by at least one radical selected from the group consisting of alkyl, cycloalkyl, aryl, alkoxy, and aryloxy radicals;
R is selected from the group consisting of methyl, ethyl, n-propyl, isopropyl, n-octadecyl, benzyl, and phenyl radicals that are unsubstituted;
$R^{11}$, $R^{12}$, $R^{13}$, $R^{14}$, $R^{15}$, $R^{16}$, $R^{17}$, and $R^{18}$ are each independently selected from the group consisting of H; aliphatic, heteroaliphatic, aromatic, alicyclic, heterocyclic radicals, heteroatom-containing radicals comprising an aromatic, alicyclic, or heterocyclic radical and an additional heteroatom linking the aromatic, alicyclic, or heterocyclic radical atom with the carbon atom of the fluorenyl group, all the foregoing radicals being unsubstituted or substituted by further carbon and/or heteroatoms; halogens; and heteroatom-containing groups; or adjacent groups selected from $R^{11}$, $R^{12}$, $R^{13}$, $R^{14}$, $R^{15}$, $R^{16}$, $R^{17}$, and $R^{18}$ together form a divalent radical thereby forming a fused ring system;
and Y⁻ represents an anion.

2. The phosphine compound or its corresponding phosphonium salt according to claim 1, wherein
$R^{11}$, $R^{12}$, $R^{13}$, $R^{14}$, $R^{15}$, $R^{16}$, $R^{17}$, and $R^{18}$ independently are selected from the group consisting of H, alkyl, cycloalkyl, aryl, and alkoxy radicals that are unsubstituted or substituted; halogens, and heteroatom-containing groups imparting water-solubility.

3. The phosphine compound or its corresponding phosphonium salt according to claim 2, wherein
$R^{11}$, $R^{12}$, $R^{13}$, $R^{14}$, $R^{15}$, $R^{16}$, $R^{17}$, and $R^{18}$ independently are selected from the group consisting of H, a methyl radical, a methoxy radical, and —SO₃H.

4. The phosphine compound or its corresponding phosphonium salt according to claim 2, wherein $R^{11}$, $R^{12}$, $R^{13}$, $R^{14}$, $R^{15}$, $R^{16}$, $R^{17}$ and $R^{18}$ are hydrogen.

5. The phosphine compound or its corresponding phosphonium salt according to claim 1, wherein R is
   (a) an unbranched alkyl radical or a benzyl radical, or
   (b) a methyl or ethyl radical.

6. The phosphine compound or its corresponding phosphonium salt according to claim 1, wherein R' and R" are
   (a) each independently selected from the group consisting of isopropyl, n-butyl, t-butyl, neopentyl, cyclohexyl, and adamantyl radicals,
   (b) each independently selected from the group consisting of isopropyl and cyclohexyl radicals
   (c) joined together to form a [3.3.1]- or [4.2.1]-phobyl radical with the phosphorous atom, or
   (d) the same radicals.

7. The phosphine compound or its corresponding phosphonium salt according to claim 1 which is selected from the group consisting of:

(9-methylfluoren-9-yl)diisopropylphosphine (9-MeFluPiPr$_2$) (5),

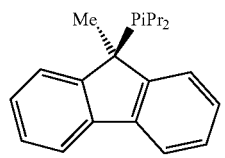
(5)

(9-ethylfluoren-9-yl)diisopropylphosphine (9-EtFluPiPr$_2$) (6),

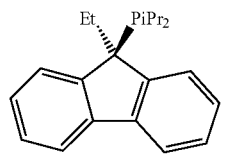
(6)

(9-benzylfluoren-9-yl)diisopropylphosphine (9-BnFluPiPr$_2$) (26),

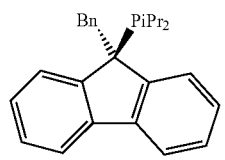
(26)

(9-octadecylfluoren-9-yl)diisopropylphosphine (9-C$_{18}$H$_{37}$FluPiPr$_2$) (7),

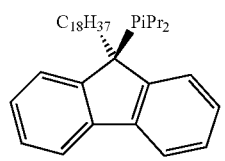
(7)

(9-methylfluoren-9-yl)dicyclohexylphosphine (9-MeFluPCy$_2$) (8),

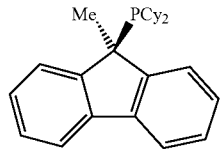
(8)

(9-ethylfluoren-9-yl)dicyclohexylphosphine (9-EtFluPCy$_2$) (9),

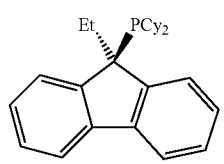
(9)

(9-benzylfluoren-9-yl)dicyclohexylphosphine (9-BnFluPCy$_2$) (10),

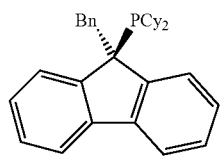
(10)

(9-octadecylfluoren-9-yl)dicyclohexylphosphine (9-C$_{18}$H$_{37}$FluPCy$_2$) (11),

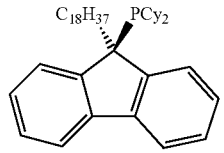
(11)

(1-methyl-9-ethylfluoren-9-yl)dicyclohexylphosphine (9-Et-1-MeFluPCy$_2$) (12),

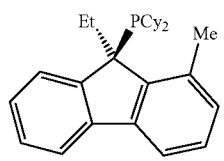
(12)

(9-ethyl-2-sulfofluoren-9-yl)dicyclohexylphosphine (2-SO$_3$H-9-EtFluPCy$_2$) (13),

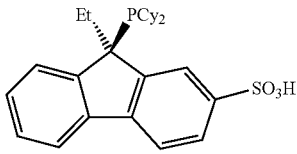

and their corresponding phosphonium salts
9-MeFluPiPr$_2$.H$^+$Y$^-$ (5a),
9-EtFluPiPr$_2$.H$^+$Y$^-$ (6a),
9-BnFluPiPr$_2$.H$^+$Y$^-$ (26a),
9-C$_{18}$H$_{37}$FluPiPr$_2$.H$^+$Y$^-$ (7a),
9-MeFluPCy$_2$.H$^+$Y$^-$ (8a),
9-EtFluPCy$_2$.H$^+$Y$^-$ (9a),
9-BnFluPCy$_2$.H$^+$Y$^-$ (10a),
9-C$_{18}$H$_{37}$FluPCy$_2$.H$^+$Y$^-$ (11a),
9-Et-1-MeFluPCy$_2$.H$^+$Y$^-$ (12a), and
9-Et-2-SO$_3$HFluPCy$_2$.H$^+$Y$^-$ (13a),
wherein Flu represents a fluoren-9-yl radical, Me represents a methyl radical, Et represents an ethyl radical, Bn represents a benzyl radical, iPr represents an isopropyl radical, and Cy represents a cyclohexyl radical.

8. The phosphonium salt according to claim 1, wherein Y$^-$ is BF$_4^-$.

9. A coordination compound comprising
(i) a phosphine compound according to claim 1; and
(ii) a transition metal selected from Groups 8, 9, 10, and 11 of the Periodic Table of the Elements.

10. The coordination compound according to claim 9, wherein the transition metal is selected from the group consisting of Pd, Ni, Pt, Rh, Ir, Ru, Co, Fe, Cu, and Au.

11. The coordination compound according to claim 9, wherein the transition metal is Pd or Ni.

12. A process for the preparation of a phosphine compound according to claim 1, which comprises
(a) deprotonating a substituted or unsubstituted fluorene by the use of a strong base, and
(b) reacting the resulting anion with (1) a phosphinous halide according to the formula R'R"PX, wherein X is Cl or Br, or (2) a phosphonous dihalide according to the formula R'PX$_2$, wherein X is Cl or Br, to form the phosphinous halide, and alkylating the phosphinous halide with an appropriate organometallic alkylation agent to introduce the R" group,
to form the phosphine compound.

13. A process for the preparation of a phosphonium salt according to claim 1, which comprises
preparing a phosphine compound as described in claim 1 and converting the phosphine compound to its corresponding phosphonium salt by reacting with H$^+$Y$^-$.

* * * * *